US009636359B2

(12) United States Patent
Kenyon et al.

(10) Patent No.: US 9,636,359 B2
(45) Date of Patent: May 2, 2017

(54) PHARMACEUTICAL COMPOSITION FOR TREATING CANCER COMPRISING TRYPSINOGEN AND/OR CHYMOTRYPSINOGEN AND AN ACTIVE AGENT SELECTED FROM A SELENIUM COMPOUND, A VANILLOID COMPOUND AND A CYTOPLASMIC GLYCOLYSIS REDUCTION AGENT

(75) Inventors: Julian Norman Kenyon, Hampshire (GB); Paul Rodney Clayton, Surrey (GB); David Tosh, Bath and North East Somerset (GB); Fernando Felquer, Glenside (AU); Ralf Brandt, Greenwith (AU)

(73) Assignee: The University of Sydney, New South Wales (AU)

( * ) Notice: Subject to any disclaimer, the term of this patent is extended or adjusted under 35 U.S.C. 154(b) by 0 days.

(21) Appl. No.: 13/502,917

(22) PCT Filed: Oct. 22, 2010

(86) PCT No.: PCT/AU2010/001403
§ 371 (c)(1),
(2), (4) Date: Jun. 22, 2012

(87) PCT Pub. No.: WO2011/047434
PCT Pub. Date: Apr. 28, 2011

(65) Prior Publication Data
US 2012/0251516 A1    Oct. 4, 2012

(30) Foreign Application Priority Data

Oct. 22, 2009   (AU) ................................ 2009905147
Jun. 17, 2010   (AU) ................................ 2010902655

(51) Int. Cl.
*A61K 33/04*        (2006.01)
*A61K 31/095*       (2006.01)
(Continued)

(52) U.S. Cl.
CPC ............ *A61K 33/04* (2013.01); *A61K 31/095* (2013.01); *A61K 31/21* (2013.01); *A61K 38/47* (2013.01); *A61K 38/4826* (2013.01); *A61K 45/06* (2013.01)

(58) Field of Classification Search
None
See application file for complete search history.

(56) References Cited

U.S. PATENT DOCUMENTS 4,514,388 A * 4/1985 Psaledakis ................... 424/94.1
4,978,332 A * 12/1990 Luck ....................... A61K 33/24
514/930
(Continued)

FOREIGN PATENT DOCUMENTS

KR    2007/0012040       1/2007
WO    WO 2009/061051   * 5/2009

OTHER PUBLICATIONS

Novak JF et al, Proenzyme Therapy of Cancer, Anticanc Res 25: 1157-1178, 2005).*
(Continued)

*Primary Examiner* — Erin M Bowers
(74) *Attorney, Agent, or Firm* — Carol L. Francis; Khin K. Chin; Bozicevic, Field & Francis LLP

(57) ABSTRACT

The present invention generally relates to pharmaceutical compositions containing a protease proenzyme and use thereof for treating cancer. The pharmaceutical compositions are directed to compositions comprising a protease proenzyme and an active agent, the composition being capable of providing a multi-functional approach for treating cancer. The pharmaceutical compositions are also directed to compositions comprising a first and a second protease proenzyme capable of activation at or near a surface of a tumor cell to enhance cell-to-cell adhesion of tumor cells, effect proteolysis of tumor cells, or induce tumor cell
(Continued)

Caco2 cell standard curve

HEK293 cell standard curve apoptosis, differentiation or immunorecognition, wherein the first protease proenzyme is chymotrypsinogen and the second protease proenzyme is trypsinogen. The pharmaceutical compositions are also directed to compositions comprising a first and second active agent each capable of inducing intracellular activity in tumor cells.

21 Claims, 47 Drawing Sheets

(51) Int. Cl.
A61K 31/21 (2006.01)
A61K 38/48 (2006.01)
A61K 45/06 (2006.01)
A61K 38/47 (2006.01)

(56) References Cited

U.S. PATENT DOCUMENTS

| | | | | |
|---|---|---|---|---|
| 5,595,756 | A * | 1/1997 | Bally et al. | 424/450 |
| 5,858,357 | A | 1/1999 | Trnka et al. | |
| 6,670,330 | B1 * | 12/2003 | Lampidis et al. | 514/23 |
| 2004/0018987 | A1 * | 1/2004 | Hoffman et al. | 514/19 |
| 2004/0167079 | A1 * | 8/2004 | Tidmarsh | A61K 31/70 514/23 |
| 2005/0026852 | A1 * | 2/2005 | Rustum | A61K 31/095 514/34 |
| 2007/0031398 | A1 * | 2/2007 | Miller | A23L 1/034 424/94.63 |

OTHER PUBLICATIONS

Dreyer et al., J. Biol. Chem. 217: 527-540 (1955).*
Wald et al., Cancer Chemother. Pharmacol. 47(Suppl.): S16-S22 (2001).*
Chabner et al., Nature Rev. 5: 65-72 (2005).*
Gura, Science 278(5340): 1041-1042 (1997).*
Novak et al., Anticancer Res. 25: 1157-1178 (2005).*
Extended European Search Report EP10824316.3, mailed Mar. 6, 2013 (11 pages).
International Preliminary Report on Patentability, mailed May 3, 2012 (8 pages).
Novak, J.F. and Trnka, F. Proenzyme therapy of cancer. *Anticancer Res*. Mar.-Apr. 2005; 25(2A):1157-77.
European Patent Office Communication App No. 10 824 316.3-1464, mailed Nov. 11, 2013 (7 pages).
Beuth et al. (2001) "Impact of complementary oral enzyme application on the postoperative treatment results of breast cancer patients—results of an epidemiological multicentre retrolective cohort study" Cancer Chemother Pharmacol, 47:S45-S54.
Cohen et al. (1999) "Oral Enzyme Therapy and Experimental Rat Mammary Tumor Metastasis" Life Sciences, 65(24):2603-1614.
Gonzalez and Isaacs (1999) "Evaluation of Pancreatic Proteolytic Enzyme Treatment of Adenocarcinoma of the Pancreas, With Nutrition and Detoxification Support" Nutrition and Cancer, 33(2):117-124.
Gurkoff and McCabe (1974) "Preliminary study on the effects of combined hydrolytic enzyme agents on mouse Krebs-2 carcinoma" Journal AOA, 672-673.
Leipner and Saller (2000) "Systemic Enzyme Therapy in Oncology; Effect and Mode of Action" Drugs, 59(4):769-780.
Popiela et al. (2001) "Influence of a complementary treatment with oral enzymes on patients with colorectal cancers—an epidemiological retrolective cohort study" Cancer Chemother Pharmacol, 47:S55-S63.
Saruc et al. (2004) "Pancreatic Enzyme Extract Improves Survival in Murine Pancreatic Cancer" Pancreas, 28:401-412.
Wald et al. (1998) "Proteinases Reduce Metastatic Dissemination and Increase Survival Time in C57BI6 Mice with the Lewis Lung Carcinoma" Life Sciences, 63(17):237-243.
Wald et al. (1998) "Polyenzyme preparation Wobe-Mugos® inhibits growth of solid tumors and development of experimental metastases in mice" Life Sciences, 62(3):43-48.

* cited by examiner

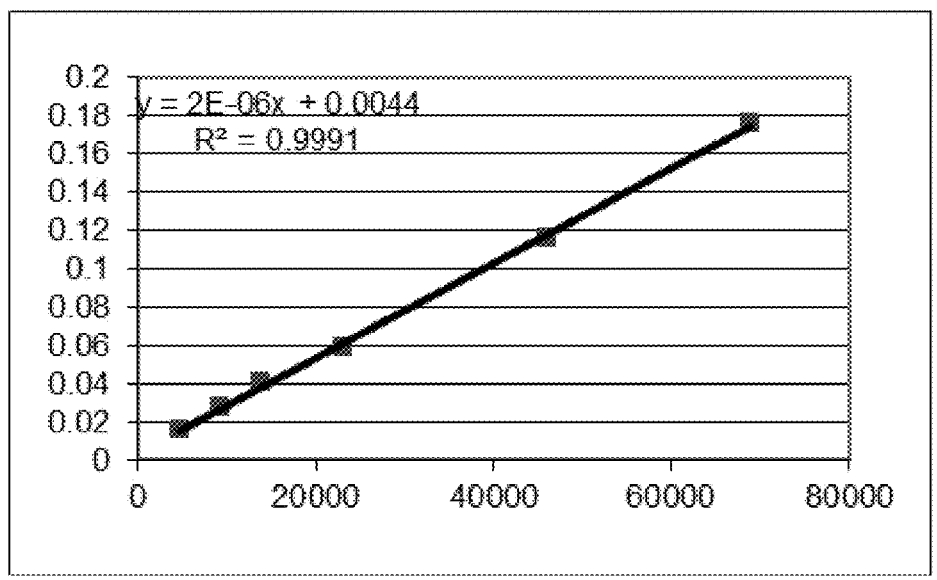
Figure 1A: Caco2 cell standard curve
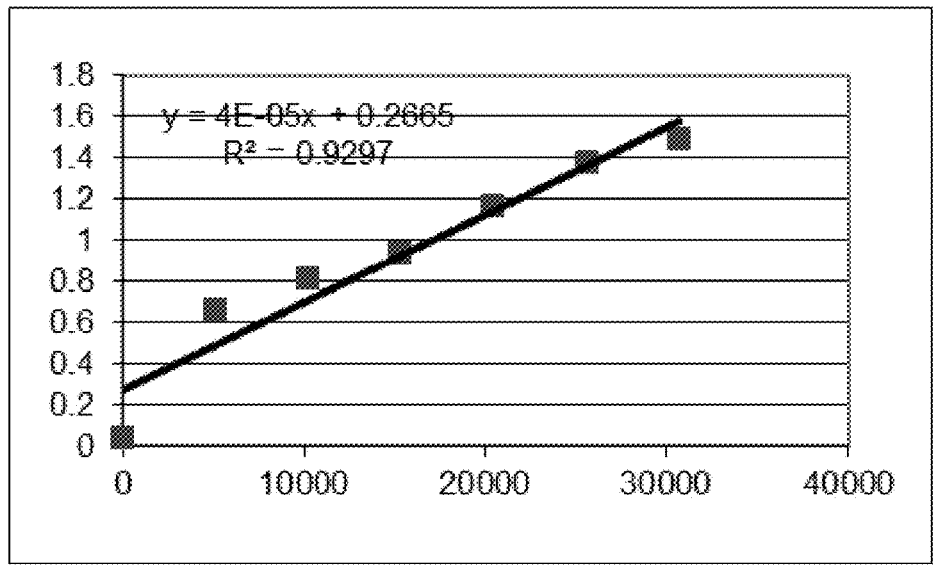
Figure 1B: HEK293 cell standard curve

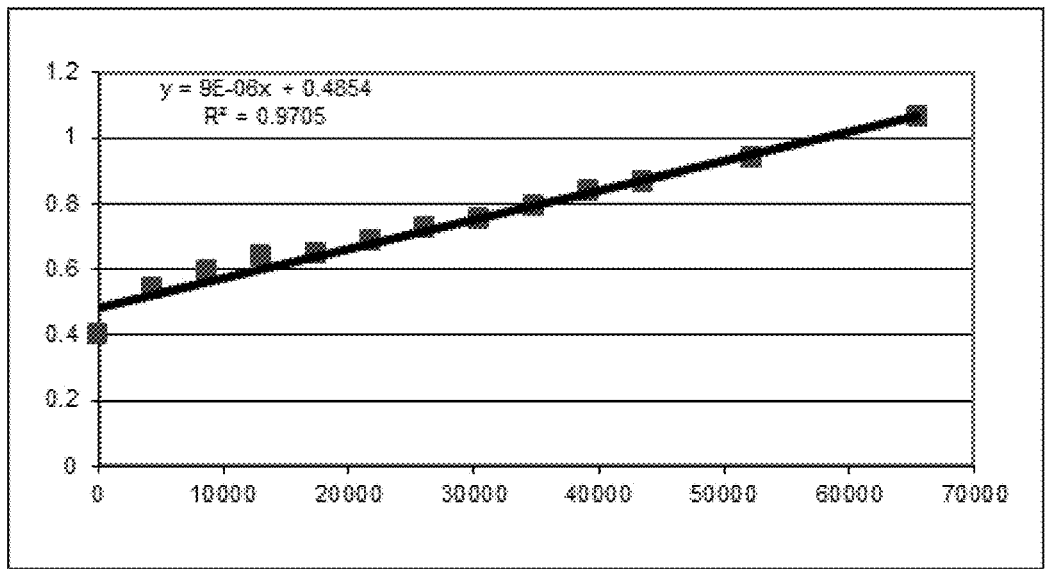
Figure 1C: OE33 cell standard curve
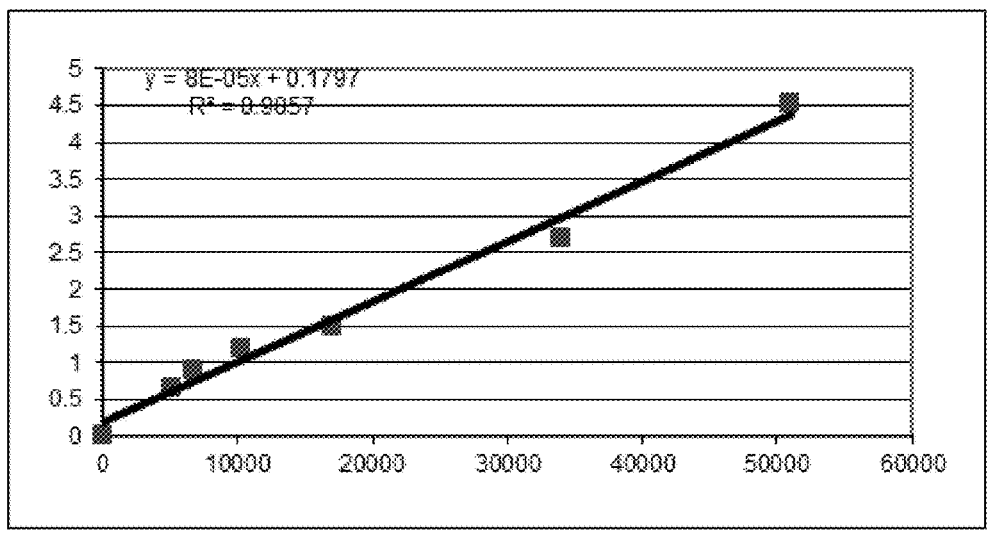
Figure 1D: Panc1 cell standard curve

OE 33 TREATMENT B

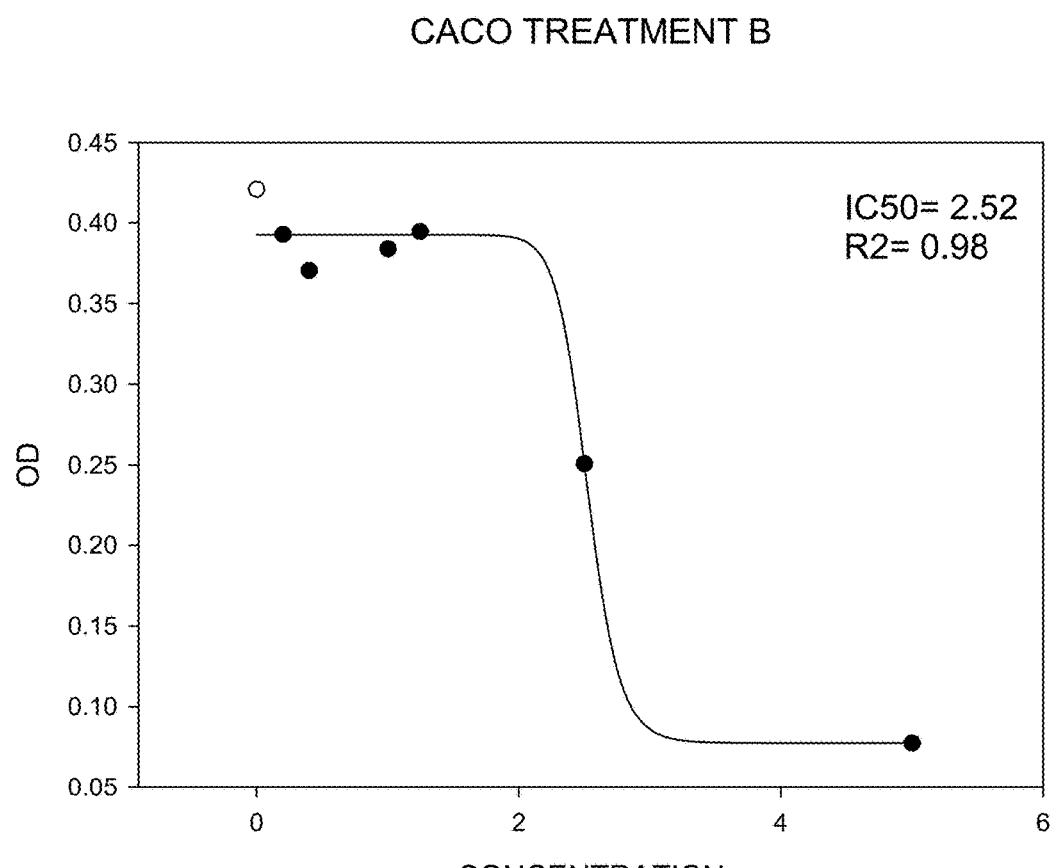
Fig 5A: Treatment B

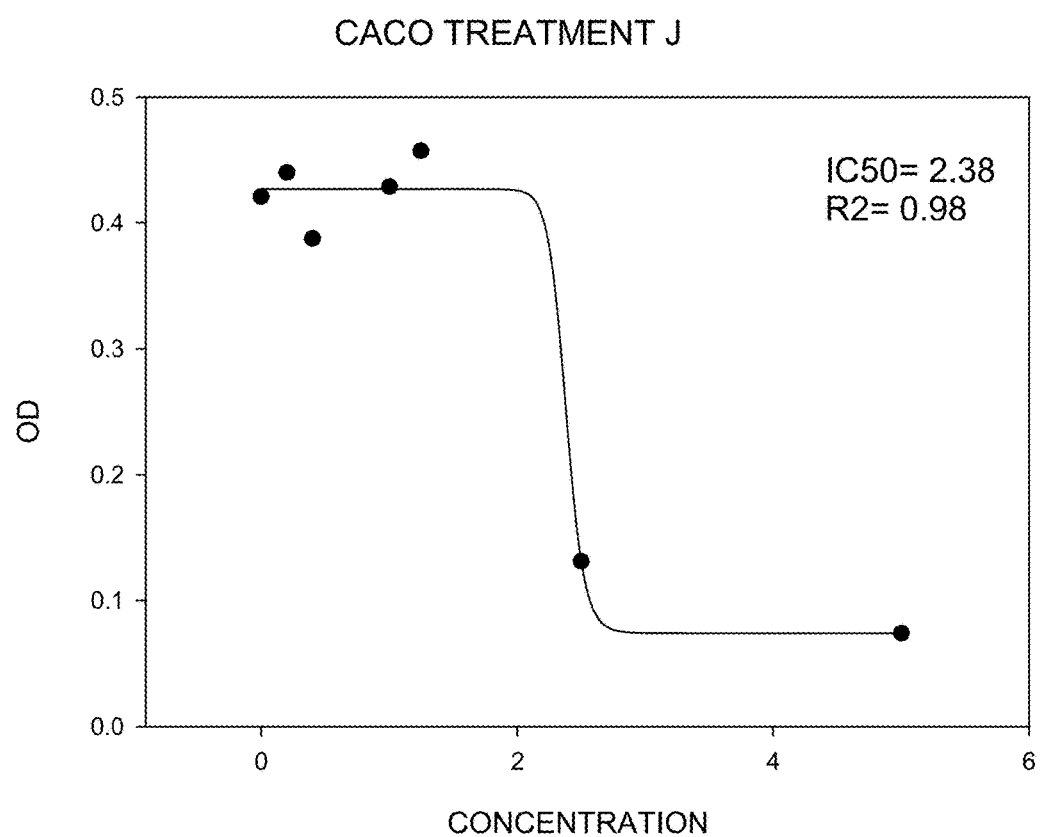
Fig 5B: Treatment J

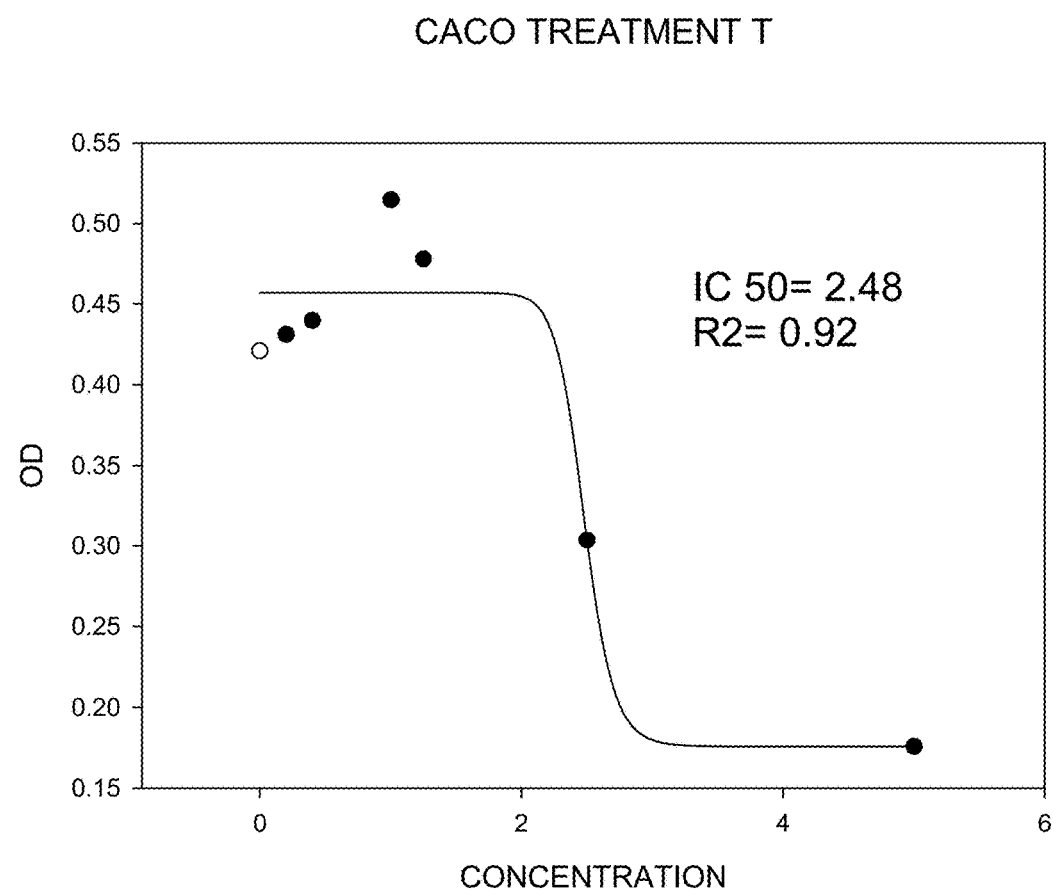
Fig 5C: Treatment T

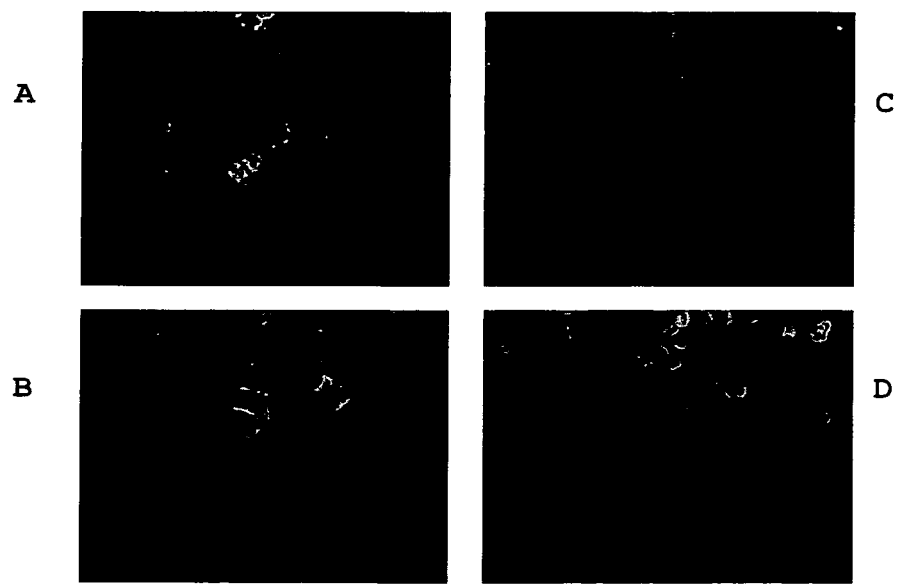
FIGUE 8A
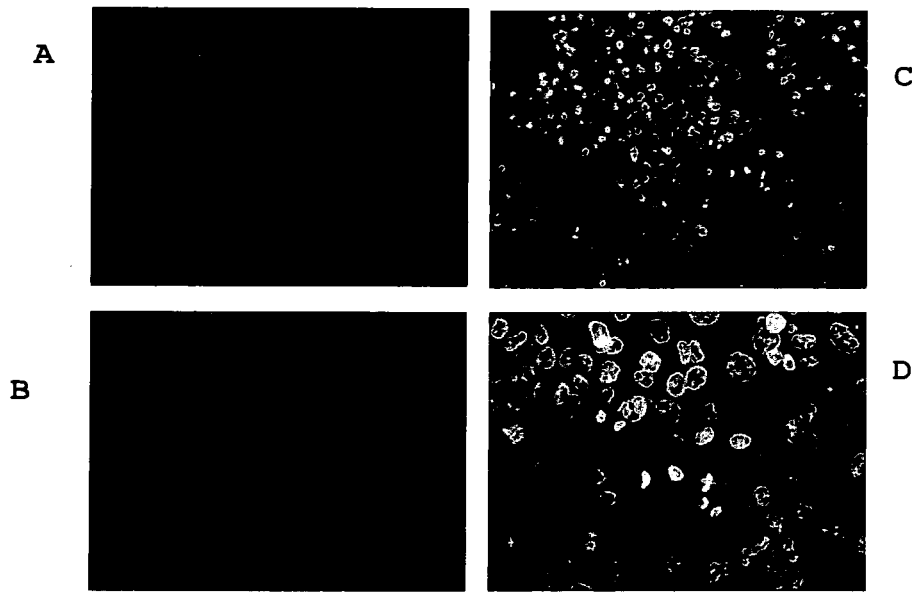
FIGURE 8B

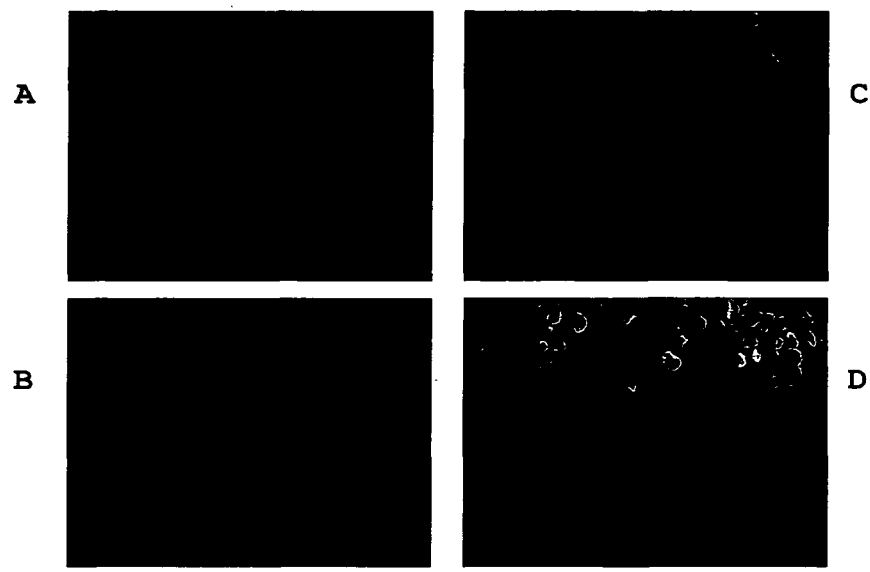
FIGUER 9A
FIGURE 9B

A-549

HCT-15

MIAPaCa-2

A-549

HCT-15

MIAPaCa-2

A-549

HCT-15

MIAPaCa-2

A-549

HCT-15

MiAPaCa-2

A-549

HCT-15

MiAPaCa-2

A-549

HCT-15

MIAPaCa-2

A-549

HCT-15

MiAPaCa-2

PHARMACEUTICAL COMPOSITION FOR TREATING CANCER COMPRISING TRYPSINOGEN AND/OR CHYMOTRYPSINOGEN AND AN ACTIVE AGENT SELECTED FROM A SELENIUM COMPOUND, A VANILLOID COMPOUND AND A CYTOPLASMIC GLYCOLYSIS REDUCTION AGENT

PRIORITY CLAIM

This application is a National Phase of PCT/AU2010/001403 filed Oct. 22, 2010, which claims priority to Australian Patent Application No. 2009905147 filed Oct. 22, 2009 and Australian Patent Application No. 2010902655 filed Jun. 17, 2010.

FIELD

The present invention generally relates to pharmaceutical compositions containing a protease proenzyme and use thereof for treating cancer.

BACKGROUND

The idea of using proteases in treating cancer has been around for more than a 100 years. In 1905, John Beard proposed the use of fresh pancreatic enzyme extracts as a possible cancer therapy and conducted successful experiments with Jersen's mouse sarcoma model. After injecting the mouse with the protease enzyme trypsin, a regression of tumours was observed. The results obtained by Beard produced great interest at that time, and crude enzyme extracts prepared from sheep pancreas were used to treat human cancer patients to reduce tumour progression and prolong survival time.

More recently, oral administration of enzymes has been shown to be well tolerated by patients with good survival rates across a range of cancers including pancreatic, bowel, colorectal and late stage myelomas. The use of high dosages of enzymes has been required because of loss and inactivation through digestion and from other enzyme inactivators in blood plasma such as serpins.

The use of proenzymes (inactive precursor form of enzymes) has been used to overcome problems encountered with the oral administration of enzymes. A proenzyme mixture including trypsinogen, which is the proenzyme form of the serine protease inhibitor trypsin, has been shown to be useful in treating carcinomas and believed to be selectively activated at the surface of tumour cells (Novak J and Trnka F, Proenzyme Therapy of Cancer, Anticancer Research, 25: 1157-1178, 2005; U.S. Pat. No. 5,858,357). The mechanism of action of trypsin is believed to occur by way of proteolysis of the tumour cells.

A need exists to identify and provide enhanced proenzyme compositions that are effective for treating cancers.

SUMMARY

A first aspect provides a pharmaceutical composition comprising a protease proenzyme and an active agent, the composition being capable of providing a multi-functional approach for treating cancer.

A second aspect provides a pharmaceutical composition comprising:
 a protease proenzyme capable of activation at or near a surface of a tumour cell to enhance cell-to-cell adhesion of tumour cells, effect proteolysis of tumour cells, or induce tumour cell apoptosis, differentiation or immunorecognition; and
 an active agent capable of inducing intracellular activity in tumour cells.

In an embodiment of the second aspect, the intracellular activity is tumour cell apoptosis, immunorecognition or differentiation.

In an embodiment of the first or second aspect, the pharmaceutical composition comprises a protease proenzyme and an active agent, the composition being capable of providing a multi-functional approach for treating cancer, wherein the protease proenzyme is selected from at least one of trypsinogen and chymotrypsinogen, and the active agent is selected from at least one of a selenium compound, a vanilloid compound and a cytoplasmic glycolysis reduction agent, and optionally a glycoside hydrolase. In a further embodiment, the protease proenzyme is trypsinogen and chymotrypsinogen.

A third aspect provides an agent or composition for treating cancer, wherein the agent comprises a protease proenzyme and an active agent, which together are capable of providing a multi-functional approach for treating cancer.

A fourth aspect provides an agent or composition for treating cancer, wherein the agent comprises:
 a protease proenzyme capable of activation at or near a surface of a tumour cell to enhance cell-to-cell adhesion of tumour cells, effect proteolysis of tumour cells, or induce tumour cell apoptosis, differentiation or immunorecognition; and
 an active agent capable of inducing intracellular activity in tumour cells.

A fifth aspect provides use of a protease proenzyme in the manufacture of a medicament comprising an active agent for treating cancer.

A sixth aspect provides use of an active agent in the manufacture of a medicament comprising a protease proenzyme for treating cancer.

A seventh aspect provides use of a protease proenzyme and an active agent in the manufacture of a medicament for treating cancer.

An eighth aspect provides use of a protease proenzyme in the manufacture of a medicament for treating cancer in a subject being treated with an active agent, wherein the active agent and protease proenzyme together are capable of effecting tumour cells, and optionally wherein the active agent is capable of inducing intracellular activity to enhance the effect of the protease proenzyme.

A ninth aspect provides use of an active agent in the manufacture of a medicament for treating cancer in a subject being treated with a protease proenzyme, wherein the active agent and protease proenzyme together are capable of effecting tumour cells, and optionally wherein the active agent is capable of inducing intracellular activity to enhance the effect of the protease proenzyme.

A tenth aspect provides a method of treating cancer comprising administering to a subject a therapeutically effective amount of a protease proenzyme and an active agent.

In an embodiment of the tenth aspect, the method comprises co-administration or sequential administration of the protease proenzyme and the active agent, and optionally additional active agent. The co-administration may comprise administration of a single medicament comprising the pharmaceutical composition of the first and second aspect, or co-administration of separate medicaments each comprising a protease proenzyme and the active agent, and optionally additional active agent. Sequential administration may involve any order of administering the protease proenzyme, active agent, or additional active agent. Sequential and co-administration may involve different routes of administration of the protease proenzyme, active agent, or additional active agent.

The method according to the tenth aspect may include administration of the protease proenzyme or the active agent to a subject already being separately treated with the active agent or the protease proenzyme, respectively.

An eleventh aspect provides a method of preparing the pharmaceutical composition of the first and second aspects, or preparation or formulation thereof, by admixing the protease proenzyme with the active agent.

In a further embodiment of the eleventh aspect, the method may further comprise the admixing of an additional active agent according to an embodiment of the first and second aspects with the protease proenzymes and/or active agent.

In an embodiment of the above aspects, the protease proenzyme is a serine protease proenzyme. The serine protease proenzyme may be trypsinogen, chymotrypsinogen or a mixture thereof. In another embodiment, the protease proenzyme comprises a first and a second protease proenzyme, wherein the first protease proenzyme is chymotrypsinogen and the second protease proenzyme is trypsinogen, and the weight ratio of chymotrypsinogen:trypsinogen is in the range of between 4:1 to 8:1. In a further embodiment, the weight ratio of chymotrypsinogen:trypsinogen is in the range of between 5:1 to 7:1. In a further embodiment, the weight ratio of chymotrypsinogen:trypsinogen is 6:1.

In an embodiment of the above aspects, the active agent is selected from at least one of the group consisting of a selenium compound, a vanilloid compound and a cytoplasmic glycolysis reduction agent, and optionally a glycoside hydrolase. For example, the active agent can be a selenium compound, or a combination consisting of a selenium compound, a vanilloid compound, a glycoside hydrolase and cytoplasmic glycolysis reduction agent.

In an embodiment of the above aspects, the pharmaceutical composition comprises a protease proenzyme and an active agent, the composition being capable of providing a multi-functional approach for treating cancer, wherein the protease proenzyme is selected from at least one of trypsinogen and chymotrypsinogen, and the active agent is selected from at least one of a selenium compound, a vanilloid compound and a cytoplasmic glycolysis reduction agent, and optionally a glycoside hydrolase.

In a further embodiment of the above aspects, the selenium compound is capable of providing a bioavailable source of selenium that can be absorbed by the body into blood plasma or inter-cellular fluids. In one particular embodiment, the selenium containing compound is methylselenocysteine or a pharmaceutically acceptable salt thereof.

In one embodiment of the above aspects, the glycoside hydrolase is an amylase, for example α-amylase.

In another embodiment of the above aspects, the cytoplasmic glycolysis reduction agent is 2-deoxy-D-glucose.

In another embodiment of the above aspects, the vanilloid compound is selected from capsiate, namely 4-hydroxy-3-methoxybenzyl (E)-8-methyl-6-nonenoate, dihydrocapsiate, namely 4-hydroxy-3-methoxybenzyl 8-methylnonanoate, and nordihydrocapsiate, namely 4-hydroxy-3-methoxybenzyl 7-methyloctanoate. Preferably, the vanilloid compound is capsiate.

In one embodiment of the above aspects, the active agent is selected from at least one of the group consisting of methylselenocysteine, capsiate, α-amylase, and 2-deoxy-D-glucose. In a particular embodiment, the active agent(s) consists of methylselenocysteine, capsiate, α-amylase, and 2-deoxy-D-glucose.

A twelfth aspect provides a pharmaceutical composition comprising a first and a second protease proenzyme capable of activation at or near a surface of a tumour cell to enhance cell-to-cell adhesion of tumour cells, effect proteolysis of tumour cells, or induce tumour cell apoptosis, differentiation or immunorecognition, wherein the first protease proenzyme is chymotrypsinogen and the second protease proenzyme is trypsinogen, and the weight ratio of chymotrypsinogen:trypsinogen is in the range of between 4:1 to 8:1.

In one embodiment of the twelfth aspect, the weight ratio of chymotrypsinogen:trypsinogen is in the range of between 5:1 to 7:1. In another embodiment, the weight ratio of chymotrypsinogen:trypsinogen is 6:1

In another embodiment of the twelfth aspect, the pharmaceutical composition further comprises an active agent as defined in any one of the embodiments described above.

A thirteenth aspect provides a pharmaceutical composition comprising a first and second active agent each capable of inducing intracellular activity in tumour cells, wherein the first active agent is a selenium compound and the second active agent is a cytoplasmic glycolysis reduction agent.

In an embodiment of the thirteenth aspect, the intracellular activity is tumour cell apoptosis, immunorecognition or differentiation. In one embodiment, the selenium compound is defined according to any one the embodiments described above. In a preferred embodiment, the selenium compound is methylselenocysteine. In another embodiment, the cytoplasmic glycolysis reduction agent is 2-Deoxy-D-glucose.

In another embodiment of the thirteenth aspect, the pharmaceutical composition further comprises a protease proenzyme as defined in any one of the embodiments described above. In another embodiment, the pharmaceutical composition further comprises an active agent selected from a vanilloid compound and a glycoside hydrolase as defined in any one of the embodiments described above.

A forteenth aspect provides a use of the pharmaceutical composition according to the twelfth or thirteenth aspects in the manufacture of a medicament for treating cancer.

A fifthteenth aspect provides a method of treating cancer comprising administering to a subject a therapeutically effective amount of the pharmaceutical composition according to the twelfth or thirteenth aspects.

The pharmaceutical compositions, protease proenzyme or active agent, of the above aspects may be provided in a pharmaceutically acceptable vehicle, carrier or diluent, and may include one or more pharmaceutically acceptable excipients.

In a further embodiment of the above aspects, the pharmaceutical compositions, agents, use, or methods, may comprise one or more additional active agents capable of enhancing the efficacy of the protease proenzyme, active agent or pharmaceutical compositions, or reducing undesirable side effects.

In a further embodiment of the above aspects, the pharmaceutical composition, protease proenzyme, active agent, and optionally additional active agent, may together, separately, or in any combination, be provided in the form of a suppository.

BRIEF DESCRIPTION OF THE DRAWINGS

FIGS. 1A-D each show a graph of cell number standard curves for Caco2, HEK293, OE33 and Panc1 cells, respectively, with optical density 492 nm;

FIGS. 5A-C each show a graph of Caco2 cells treated with proenzyme reference formulations B, J and T, respectively;

FIGS. 8A and 8B each provide photomicrographs showing the up-regulation of β-catenin in Panc1 cells following treatment with proenzyme reference formulation J;

FIGS. 9A and 9B each provide photomicrographs showing the up-regulation of E-Cadherin in Panc1 cells following treatment with proenzyme reference formulation J;

DESCRIPTION OF THE ABBREVIATIONS

Figure 2:
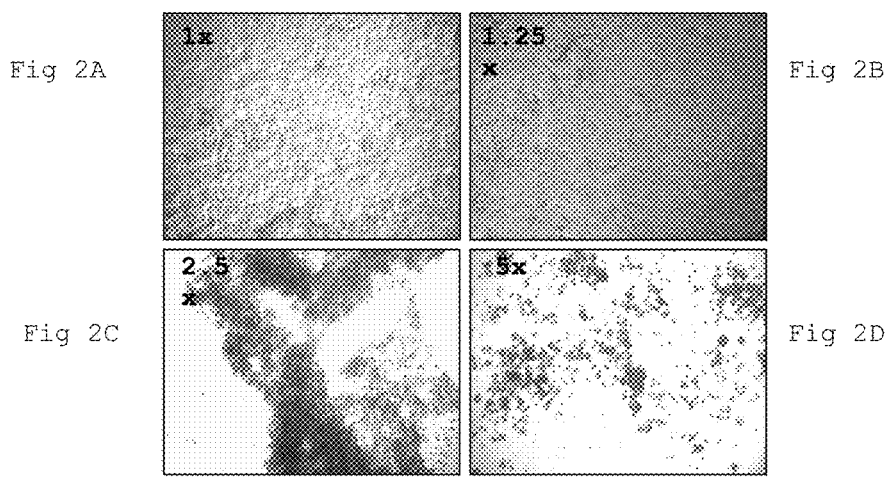
FIG. 2 shows a photomicrograph of OE33 cells treated with a proenzyme reference formulation B.

In the Examples, reference will be made to the following abbreviations in which:

α-Amylase A
ANOVA Analysis of Variance
Avg Average
bFGF Basic Fibroblast Growth Factor
BSA Bovine Serum Albumin
BW Body Weight
° C. Degrees Celsius
C Capsiate
Caco2 Human colon adenocarcinoma cell line
Chymotrypsinogen pC
DAvg Change in average body weight
DCM 2-Deoxyglucose, Capsiate and Methylselenocysteine
D 2-Deoxy-D-glucose
F Fahrenheit
h Hour
Hb Haemoglobin
i.p. Intraperitoneal
IU International Units
JBp1 Proenzyme formulation comprising trypsinogen, chymotrypsinogen and α-amylase
JBp1vP Proenzyme formulation comprising trypsinogen, chymotrypsinogen and α-amylase (pC:pT:A) in 6:1:0.25 by weight ratio
JBp1-DCM Proenzyme formulation comprising trypsinogen, chymotrypsinogen, α-amylase, 2-deoxyglucose, capsiate and methylselenocysteine
Mn Number average molecular weight
Mw Weight average molecular weight
MW Molecular weight
M Methylselenocysteine
MSeA Methylselenic acid
MTD Maximum tolerable dose
NMP N-methyl-2-Pyrrolidone
OE33 Oesophageal adenocarcinoma cell line
Panc1 Human pancreatic ductal carcinoma cell line
PBS Phosphate Buffered Saline
PEG300 Polyethylene Glycol 300
p.o. Per os, (oral gavage)
RD Recommended dose
SeMeT Selenomethionine
SEM Standard Error of the Mean
SRB Sulforhodamine B protein-staining assay
Trypsinogen pT
Wt % Weight percentage
v/v Volume for volume

DETAILED DESCRIPTION

Although protease proenzyme formulations have been shown to provide therapeutic benefits in treating cancer, the mechanism of action of protease proenzymes on cancer cells and malignant tumours is not completely understood in the art. The applicant therefore undertook an investigation of the effects and mechanisms involved with treating cancer cell lines with serine protease proenzyme formulations comprising trypsinogen and chymotrypsinogen, which involved investigations on three different cancer cell lines (Panc1, Caco2 and OE33). Of particular note was the surprising finding that the protease proenzymes were involved in differentiation of CaCo2 tumour cells (possible conversion of malignant cells to non-malignant cells) and in the up-regulation of the expression of E-cadherin and β-catenin in all three cell lines.

The applicant believes that a reduction in metastasis by serine protease proenzyme formulations arises through the up-regulation of the expression and formation of E-caderin/β-catenin complexes, which are involved in cell-to-cell adhesion. The corollary of increased cell-to-cell adhesion is a reduction in metastasis because malignant cells are less likely to leak or escape from the primary tumour.

With the availability of this new information, the present inventors investigated formulations comprising a protease proenzyme in combination with one or more active agents that are capable of providing a working interrelationship in treating cancer. For example, the active agent may provide improved cancer treating activity to the pro-enzyme alone by operating on a different function of the tumour cell in respect to the expression of E-cadherin and β-catenin, but where the overall result is to provide an enhanced treatment, which may include a reduction in metastasis and/or an increase in apoptosis, immunorecognition or differentiation of the tumour cell. In other words, the pharmaceutical compositions of the first and second aspects provide a protease proenzyme in combination with an active agent, the combination enabling a multi-cellular or multi-functional approach to targeting or treating a cancer cell or cells. For example, the proenzymes are activated at or near the surface of the tumour cell to promote expression of cell-to-cell adhesion molecules and thereby reduce metastasis, while a separate active agent, such as methylselenocysteine, may operate at an intracellular level to assist with the reduction in metastasis, differentiation or death of the tumour cell (e.g. necrosis, apoptosis, immunorecognition).

Protease Proenzymes

A proenzyme (also known as zymogen) is a precursor form of an enzyme not having the specific activity of the enzyme, and therefore typically referred to as an inactive form of the enzyme. Proenzymes are maintained in their inactive state until required so that non-specific effects of enzyme activity at undesirable sites are prevented or reduced. Proenzymes can be activated into corresponding active enzymes by other enzymes resulting in a cascade of activation, which includes the action of multiple enzymes and auto-activation. Proenzymes are considered to be selectively activated by cancer cells, which in turn are subjected to proteolysis by the active enzyme.

The term "protease proenzyme" as used herein means a precursor form of a protease enzyme that can be activated in situ into the active protease enzyme. The protease proenzymes may be of human or animal original. The protease enzyme may act to provide one or more cellular effects including proteolysis, up-regulation of the expression of E-cadherin and/or β-catenin, apoptosis, enhanced immunorecognition, and tumour cell differentiation. Protease enzymes include serine proteases, threonine proteases, cysteine proteases, aspartate proteases, metalloproteases, or glutamic acid proteases. The proteases may be endopeptidases or exopeptidases. Endopeptidase (or endoproteinase) are proteolytic peptidases that break peptide bonds of nonterminal amino acids (i.e. within the molecule), in contrast to exopeptidases, which break peptide bonds at the ends of the molecule.

In one embodiment, the protease proenzyme is a precursor of an enzyme from peptidases of enzyme class 3.4, particularly serine endopeptidases of enzyme class 3.4.21, and more particularly chymotrypsin from enzyme class 3.4.21.1, chymotrypsin C from enzyme 3.4.21.2 or trypsin from enzyme class 3.4.21.4 (classes grouped according to the classification of the Nomenclature Committee of the International Union of Biochemistry and Molecular Biology).

In an embodiment, the protease proenzyme is a serine protease proenzyme. Serine protease enzyme(s) include trypsin or chymotrypsin type forms, subtilisin-type, alpha/beta hydrolase, and signal peptidases. Serine proteases may include the following serine endopeptidases: chymotrypsin, metridin, trypsin, thrombin, coagulation factor Xa, plasmin, enteropeptidase, acrosin, α-Lytic endopeptidase, glutamyl endopeptidase, cathepsin G, coagulation factor VIIa, coagulation factor IXa, cucumisin, prolyl oligopeptidase, coagulation factor Xia, brachyuran, plasma kallikrein, tissue kallikrein, pancreatic elastase, leukocyte elastase, coagulation factor XIIa, Chymase, activated complement C1r, activated complement C1s, classical-complement-pathway C3/C5 convertase, complement factor I, complement factor D, alternative-complement-pathway C3/C5 convertase, cerevisin, hypodermin C, lysyl endopeptidase, endopeptidase La, γ-renin, venombin AB, leucyl endopeptidase, tryptase, scutelarin, kexin, subtilising, oryzin, peptidase K, thermomycolin, thermitase, endopeptidase So, t-plasminogen activator, protein C (activated), pancreatic endopeptidase E, pancreatic elastase II, IgA-specific serine endopeptidase, u-plasminogen activator, venombin A, furin, myeloblastin, semenogelase, granzyme A, granzyme B, streptogrisin A, streptogrisin B, glutamyl endopeptidase II, oligopeptidase B, limulus clotting factor C, limulus clotting factor B, limulus clotting enzyme, repressor LexA, signal peptidase I, togavirin, flavivirin, endopeptidase C1p, proprotein convertase 1, proprotein convertase 2, snake venom factor V activator, lactocepin, assembling, hepacivirin, spermosin, sedolisin, xanthomonalisin, C-terminal processing peptidase, physarolisin, mannan-binding lectin-associated serine protease-2, rhomboid protease, hepsin, peptidase Do, HtrA2 peptidase, matriptase, C5a peptidase, aqualysin 1, site-1 protease, pestivirus NS3 polyprotein peptidase, equine arterivirus serine peptidase, infectious pancreatic necrosis birnavirus Vp4 peptidase, SpoIVB peptidase, stratum corneum chymotryptic enzyme, kallikrein 8, kallikrein 13, oviductin.

In a particular embodiment, the serine protease proenzyme is trypsinogen, chymotrypsinogen or a mixture thereof. The proenzymes trypsinogen and chymotrypsinogen may be precursors of the enzymes selected from chymotrypsin classes 3.4.21.1 or 3.4.21.2 or trypsin from class 3.4.21.4, or selected from any other suitable source. These enzymes are commercially available and may be of bovine or porcine origin.

Chymotrypsinogen is a proenzyme form of the enzyme chymotrypsin, which preferentially cleaves proteins at the following amino acids: tyrosine, tryptophan, phenylalanine and leucine. Chymotrypsin may be referred to or include chymotrypsin A, chymotrypsin B (including B1 and B2 forms), chymotrypsin C, α-chymarophth, avazyme, chymar, chymotest, enzeon, quimar, quimotrase, α-chymar, α-chymotrypsin A, α-chymotrypsin. Chymotrypsin C can be formed from pig chymotrypsinogen C or from cattle subunit II of procarboxypeptidase A, and preferentially cleaves proteins at the following amino acids: tyrosine, tryptophan, phenylalanine, leucine, methionine, glutamine, and asparagine. Chymotrypsinogen includes chymotrypsinogen B1 and chymotrypsinogen B2.

Trypsinogen is a proenzyme form of trypsin, which preferentially cleaves proteins at arginine and lycine. Trypsin may be referred to or include α-trypsin, β-trypsin, cocoonase, parenzyme, parenzymol, tryptar, trypure, pseudotrypsin, tryptase, tripcellim, sperm receptor hydrolase β-trypsin can be formed from trypsinogen by cleavage of one peptide bond. Further peptide bond cleavages produce a and other iso-forms. Multiple cationic and anionic trypsins can be isolated from the pancreas of many vertebrates and from lower species including crayfish, insects (cocoonase) and microorganisms (*Streptomyces griseus*). In normal processes during digestion, inactive trypsinogen is activated by enteropeptidase present in intestinal mucosa to form the enzyme trypsin, which being a serine protease then acts to cleave the peptide bonds on the carboxyl side of basic amino acids/proteins.

As mentioned, the proenzyme form essentially provides an inactivated form of the enzyme that becomes activated in situ (e.g in vivo or in vitro activation). For example, activation of the proenzyme (conversion of proenzyme to active enzyme) may occur on contact with the surface of the tumour cell. It is believed that the proenzymes trypsinogen and chymotrypsinogen are selectively activated into the enzymes trypsin and chymotrypsin on contact with tumour cells and not on contact with healthy cells. The use of proenzymes reduces problems associated with providing, in situ, an active enzyme, such as undesirable reactions or inactivation of the enzyme before reaching an intended target of a tumour cell.

In relation to tumour cells, protease enzymes can act to break down the cell wall of malignant cells by cleaving the amide bonds present in peptide chains of the cell walls (proteolysis). It is also understood that protease inhibitors, which are present in non-malignant cells and inhibit or reduce the effect of enzymes in breaking down cell walls, are absent in malignant tumour cells. In addition to providing proteolytic activity, the protease proenzymes can upregulate the expression of β-catenin and E-cadherin in tumour cells. Cell-to-cell adhesion is facilitated by complex formation or bonding between β-catenin and E-cadherin at the cell surface, and therefore increased expression of β-catenin and E-cadherin leads to enhanced cell-to-cell adhesion and thereby reducing metastasis of tumour cells. The protease proenzymes may also provide other cellular activity such as increased immunorecognition or differentiation.

Active Agents

The active agents of the first aspect, second aspect, twelfth aspect and thirteenth aspect, are for treating cancer or inducing intracellular activity to enhance treatment of a tumour cell.

In an embodiment, the intracellular activity is tumour cell apoptosis, necrosis, immunorecognition or differentiation.

In relation to the multi-functional approach, in one embodiment the active agents are capable of providing a working interrelationship with the protease proenzymes in treating cancer. For example, the active agent may provide improved cancer treating activity that may or may not be related to the expression of E-cadherin and β-catenin, but where the overall result is to provide an enhanced treatment, such as a reduction in metastasis and/or an increase in apoptosis, immunorecognition or differentiation of the tumour cell. The active agent may operate at an intracellular level to assist with the reduction in metastasis, differentiation or death of the tumour cell (e.g. necrosis, apoptosis, immunorecognition).

In an embodiment, the active agent is selected from at least one of the group consisting of a selenium compound, a vanilloid compound and a cytoplasmic glycolysis reduction agent, and optionally a glycoside hydrolase. For example, the active agent may consist of a selenium compound, or may be a combination of active agents consisting of a selenium compound, a vanilloid compound, a glycoside hydrolase, and a cytoplasmic glycolysis reduction agent.

Selenium Compound

In one embodiment, the term "selenium compound" means any compound containing selenium that is capable of providing a bioavailable source of selenium. The selenium compound may include inorganic compounds, such as minerals containing selenites and selenates, and organic compounds, such as methylselenocysteine. The selenium compound may be sourced as a plant extract or from commercial synthesis. In a particular embodiment, the selenium compound provides a bioavailable source of selenium that can be readily absorbed by the body into blood plasma or intercellular fluids.

In an embodiment, the term "selenium compound" means an amino acid containing a divalent or tetravalent selenium compound. The amino acid may be selected from isoleucine, alanine leucine, asparagine, lysine, aspartate, methionine, cysteine, phenylalanine, glutamate, threonine, glutamine, tryptophan, glycine, valine, proline, serine, tyrosine, arginine, histidine. The divalent or tetravalent selenium may also be present in the amino acid in replacement to sulphur or other divalent species that may naturally occur in these amino acids.

In an embodiment, the term "selenium compound" means a compound containing a divalent selenium compound of formula I or tetravalent selenium compound of formula II:

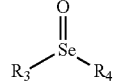

Formula I

Formula II or a pharmaceutically acceptable salt thereof, wherein:

$R_1$ and $R_3$ are each independently selected from H, OH, —C(O)H, —C(O)OH, —C(O)—OR$_5$, $C_{1-4}$alkyl and $C_{2-6}$alkenyl, wherein $C_{1-4}$alkyl and $C_{2-6}$alkenyl are optionally substituted with 0-3 substituents independently selected from halogen, OH, —NH$_2$, —C(O)OH, —C(O)—OR$_5$;

$R_2$ and $R_4$ are each independently selected from H, OH, —C(O)H, —C(O)OH, —C(O)—OR$_5$, $C_{1-12}$alkyl and $C_{2-12}$alkenyl, wherein $C_{1-12}$alkyl and $C_{2-12}$alkenyl are optionally interrupted with one or more groups selected from —NH—, —N(C$_{1-4}$alkyl)-, —NH(CO)—, —C(O)—, —C(O)O—, —O— and —C(NH$_2$)H—C(O)O—, and optionally substituted with 0-3 substituents independently selected from halogen, —NH$_2$, —OH, —C$_{1-4}$alkyl, —C(O)OH, —C(O)H, —C(O)—OR$_5$, —N(C$_{1-4}$alkyl)H, —N(C$_{1-4}$alkyl)$_2$, —C(NH$_2$)H—C(O)OH, cycloalkyl, cycloalkenyl and aryl; and wherein $R_5$ is selected from alkyl, alkenyl, cycloalkyl and cycloalkenyl, particularly $C_{1-12}$alkyl.

In the above embodiment it will be appreciated that:

$C_{1-4}$alkyl and $C_{1-12}$alkyl mean a straight, branched or cyclo alkyl chain, or combination thereof; and $C_{2-6}$alkenyl and $C_{2-12}$alkenyl mean a straight, branched or cyclo alkenyl chain, or combination thereof.

In a particular embodiment, $R_1$ and $R_3$ are each independently selected from H, OH and $C_{1-4}$alkyl, and more particularly are methyl.

In another particular embodiment, $R_2$ and $R_4$ are each independently selected from H, OH and —C$_{1-6}$alkyl-C(NH$_2$)H—C(O)OH, and more particularly —C$_{1-3}$alkyl-C(NH$_2$)H—C(O)OH.

In another embodiment, the selenium compound is selected from methylselenocysteine, methylselenol and methylseleninic acid, or a pharmaceutically acceptable salt or mixture thereof. In a particular embodiment, the selenium compound is methylselenocysteine or a pharmaceutically acceptable salt thereof.

The selenium compounds are selected to enhance the efficacy of treatment of the protease proenzymes by providing a working interrelationship or multifunctional approach to treating cancer. For example, the selenium compound may induce intracellular activity to enhance treatment of the tumour cell by way of tumour cell apoptosis, immunorecognition and/or differentiation.

A connection between selenium intake and cancer has been known for decades.

Selenium is an essential trace mineral having a Recommended Dietary Allowance (RDA) of 55 micrograms. Selenium is essential for activating various key enzymes, such as the antioxidant glutathione peroxidase, the metabolic enzyme thioredoxin reductase, and the thyroid-hormone-activating enzyme iodothyronine deiodinase. Selenium has been considered to provide anticancer protection through the enhancing of cell and liver antioxidant activity (glutathione peroxidase) or through promoting removal of environmental carcinogens (glutathione S-transferase). Organic forms of selenium, such as selenomethionine, can be toxic at levels of about 3500 micrograms daily, while inorganic forms of selenium, such as sodium selenite/selenate, may be toxic at about 1500 micrograms. Selenium is safe over long term dosing at about 400 mcg/day levels, although cancer treatment protocols may treat at ranges of about 900 to 2,000 mcg selenium daily.

Some selenium anticancer effects have been shown to occur at doses close to potentially toxic dose levels, yet selenoprotein enzymes are typically saturated (activity maximized) at dietary intakes of only 90 mcg selenium per day, far below optimal anticancer doses.

Inorganic forms, such as selenite/selenate, have been shown to be more effective at treating cancer than typical organic forms, such as selenomethionine. Selenite/selenate forms can be metabolized to hydrogen selenide, which is toxic to both cancer cells and healthy cells and operates through a less selective and more invasive mechanism of necrosis (as opposed to apoptosis). Selenomethionine is less toxic but gets largely incorporated into general body proteins that have no anticancer activity.

Methylselenocysteine (also known as Se-methylselenocysteine) is a chemopreventive agent that blocks cell cycle progression and proliferation of premalignant mammary lesions, and induces apoptosis of cancer cell lines, with very low toxicity and body accumulation. Methylselenocysteine is formed naturally in various plants, including garlic, wild leeks, onions and broccoli grown on high selenium soil, and methylselenocysteine rich foods have shown good anticancer activity, without excess tissue accumulation or toxicity. Methylselenocysteine is converted to methylselenol by the beta-lyase enzyme. In regards to activity against tumour cells, methylselenol is known to inhibit angiogenesis and cause apoptosis but has low toxicity and is easily removed by the body.

The following chemical structures for various selenium compounds are:

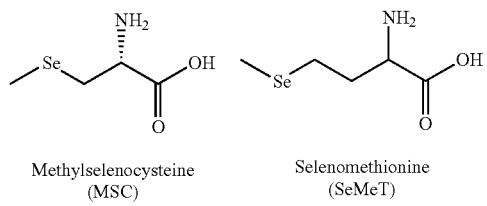

Methylselenocysteine (MSC)   Selenomethionine (SeMeT)

-continued

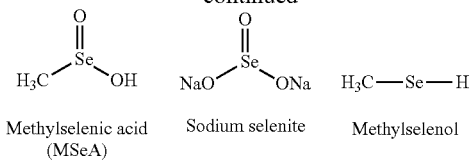

Methylselenic acid (MSeA)   Sodium selenite   Methylselenol

The selenium compounds according to the above embodiments may include all pharmaceutically acceptable salts, hydrates, solvates, crystal forms, diastereomers, conformational isomers (eg. cis and trans isomers), tautomers, prodrugs, metabolites, and enantiomeric forms thereof.

Vanilloid Compound

In one embodiment, the term "vanilloid compound" means any compound containing a vanillyl or vanilloyl type moiety or pharmacore. The vanilloid compounds include known chemical classes of naturally occurring vanilloids such as resiniferanoids, capsaicinoids, unsaturated dialdehydes, and triprenyl phenols. For example, compounds from these known chemical classes include resiniferatoxin, capsaicin, isovelleral, and scutigeral, respectively. Examples of other vanilloid compounds include vanillin, vanillic acid, nonivamide, olvanil, dihydrocapsaicin and vanillyl mandelic acid. The vanilloid compounds may include naturally sourced compounds such as capsaicin or semi-synthetic or synthetic vanilloids such as capsazepine.

In another embodiment, the term "vanilloid compound" means a compound of general formula III:

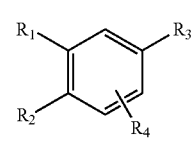

Formula III or a pharmaceutically acceptable salt thereof, wherein:

$R_1$ and $R_2$ are each independently selected from H, OH, $OCH_3$, C(O)H, $OC_{2-6}$alkyl, $OC_{2-6}$alkenyl, SH, $SC_{1-6}$alkyl, $NH_2$, $NHC_{1-6}$alkyl and $N(C_{1-6}$alkyl$)_2$;

$R_3$ and $R_4$ are each independently selected from H, $C_{1-20}$alkyl, $C_{2-20}$alkenyl and $C_{2-20}$alkynyl, wherein the $C_{1-20}$alkyl, $C_{2-20}$alkenyl and $C_{2-20}$alkynyl, are optionally interrupted with one or more groups selected from —$NR_6$—, —NH(CO)—, —C(O)—, —C(O)O—, —O—, —C($NR_6R_6$)H—C(O)O—, —C(S)—, —C(S)$NR_6$— and —$NR_6$—C(S)—$NR_6$, and optionally substituted with 0-3 substituents independently selected from halogen, —$NH_2$, —OH, —$C_{1-4}$alkyl, —C(O)OH, —C(O)$OR_5$, —C(O)H, —N($C_{1-4}$alkyl)H, —N($C_{1-4}$alkyl$)_2$, —C($NH_2$)H—C(O)OH, —C(S)—, optionally substituted cycloalkyl, optionally substituted cycloalkenyl and optionally substituted aryl; and wherein $R_5$ is selected from alkyl, alkenyl, cycloalkyl, cycloalkenyl, particularly $C_{1-12}$alkyl; and $R_6$ is selected from H, $C_{1-6}$alkyl; and $R_3$ and $R_4$ may be joined to form an optionally substituted unsaturated or saturated ring having from 3 to 8 carbon atoms in the ring including from 0 to 3 heteroatoms selected from O, S and N.

In the above embodiment it will be appreciated that:

$C_{2-6}$alkyl and $C_{1-20}$alkyl mean a straight, branched or cyclo alkyl chain, or combination thereof;

$C_{2-6}$alkenyl and $C_{2-20}$alkenyl mean a straight, branched or cyclo alkenyl chain, or combination thereof;

$C_{2-20}$alkynyl means a straight, branched or cyclo alkynyl chain, or combination thereof;

Optionally substituted cycloalkyl, optionally substituted alkylcycloalkenyl and optional substituted aryl mean optional substitution with one or more groups selected from halogen, —$NH_2$, —OH, —$C_{1-4}$alkyl, —C(O), —C(O)OH, —C(O)O$R_5$, —C(O)H, —N($C_{1-4}$alkyl)H, —N($C_{1-4}$alkyl)$_2$, —C($NH_2$)H—C(O)OH, cycloalkyl, cycloalkenyl and aryl, and for example would include resiniferatoxin.

In a particular embodiment, $R_1$ and $R_2$ are each independently selected from OH, C(O)H and $OCH_3$, and more particularly OH and $OCH_3$.

In another particular embodiment, $R_3$ is selected from —$C_{1-4}$alkyl-NH—C(O)—$C_{1-12}$alkenyl, —$C_{1-4}$alkyl-NH—C(O)—$C_{1-12}$alkyl, and more particularly —$CH_2$—NH—C(O)—$C_4H_8$—CH=CH—CH($CH_3$)$CH_3$. It will be appreciated in this embodiment that the alkyl or alkenyl chain may be straight or branched.

In another particular embodiment, $R_3$ is selected from —$C_{1-4}$alkyl-O—C(O)—$C_{1-12}$alkenyl, —$C_{1-4}$alkyl-O—C(O)—$C_{1-12}$alkyl, and more particularly —$CH_2$—O—C(O)—$C_4H_8$—CH=CH—CH($CH_3$)$CH_3$. It will be appreciated in this embodiment that the alkyl or alkenyl chain may be straight or branched.

In another particular embodiment, $R_4$ is H.

The vanilloid compound can be selected from capsaicin, dihyrdocapsaicin and nordihydrocapsaicin.

Preferably, the vanilloid compound is selected from capsiate, dihyrdocapsiate and nordihydrocapsiate. In an embodiment, the vanilloid compound is capsiate. Capsiate, dihyrdocapsiate and nordihydrocapsiate, are preferably provided in a form that is substantially free of capsaicins, for example having a purity of at least 80%, 85%, 90%, 95%, 98%, 99% or 99.9%. It will be appreciated that capsiates, which are typically obtained as extracts from chillies, usually contain small amounts of capsaicins and other structurally similar compounds. Capsaicins can present an undesirable inflammatory response (by triggering large localised histamine release), and therefore particular types of administration regimes may be less desirable for particular compounds, or for particular amounts or purities of those compounds, which can be tailored to suit the specific requirements. One source of high purity capsiate is provided by "CH-19" sweet peppers sourced by Ajinomoto Co.

In another embodiment, the vanilloid compound is selected from 8-methyl-N-vanillyl-6-non-enamide; N-vanillylnonanamide; N-(9-decenyl)-4-hydroxy-3-methoxy-phenylacetamide; N-(9Z-dodecenyl)-4-hydroxy-3-methoxy-phenylacetamide; N-(9Z-tetradecenyl)-4-hydroxy-3-methoxyphenylacetamide; N-((4-hydroxy-3-methoxyphenyl)-methyl)-9-decenamide; N-((4-hydroxy-3-methoxyphenyl)-methyl)-9Z-dodecenamide; N-((4-hydroxy-3-methoxyphenyl)-methyl)-9Z-tetradecenamide and N-((4-(3-phenyl-2(S)-2-amino-1-propoxy)-3-methoxy-phenyl)-methyl)-nonanamide.

In another embodiment, the vanilloid compound is capsazepine, namely N-[2-(4-chlorophenyl)ethyl]-7,8-dihydroxy-1,3,4,5-tetrahydro-2-benzazepine-2-carbothiomide.

A number of vanilloids, notably capsaicin, bind to the transient receptor potential vanilloid type 1 (TRPV1) receptor, an ion channel which naturally responds to noxious stimuli such as high temperatures and acidic pH. Other vanilloids which act at TRPV1 include resiniferatoxin and olvanil.

Vanilloid compounds include capsaicin and capsiate, which is also known as a capsinoid. Capsinoids, which include capsiate, dihydrocapsiate, and nordihydrocapsiate, are substances naturally present in chilli peppers. Although they are structurally similar to capsaicin, which is the compound that causes pungency in hot peppers, capsinoids largely lack this characteristic and have an estimated "hot taste threshold" of about 1/1000th that of capsaicin.

Capsaicin is (E)-N-[(4-hydroxy-3-methoxyphenyl)methyl]-8-methyl-6-nonenamide, and analogues thereof include dihydrocapsaicin, which is a 6,7-dihydro derivative of capsaicin. As mentioned above, capsinoids include capsiate, namely 4-hydroxy-3-methoxybenzyl (E)-8-methyl-6-nonenoate, dihydrocapsiate, namely 4-hydroxy-3-methoxybenzyl 8-methylnonanoate, and nordihydrocapsiate, namely 4-hydroxy-3-methoxybenzyl 7-methyloctanoate. The chemical structure of some of these compounds are as follows:

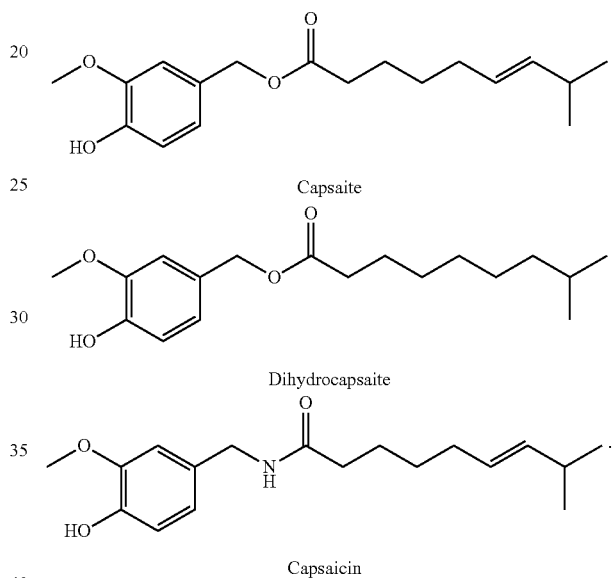

Capsiates can provide apoptosis and reduced tumour incidence. Capsiates are believed to induce apoptosis by affecting the redox state of the cells via cell mitochondria.

The vanilloid compounds are selected to enhance the efficacy of treatment of the protease proenzymes by providing a working interrelationship or multifunctional approach to treating cancer. For example, the vanilloid compound may induce intracellular activity to enhance treatment of the tumour cell by way of tumour cell apoptosis, immunorecognition and/or differentiation.

The following chemical structures for vanillin, vanillic acid and resiniferatoxin are:

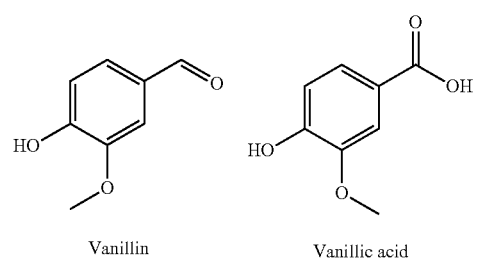

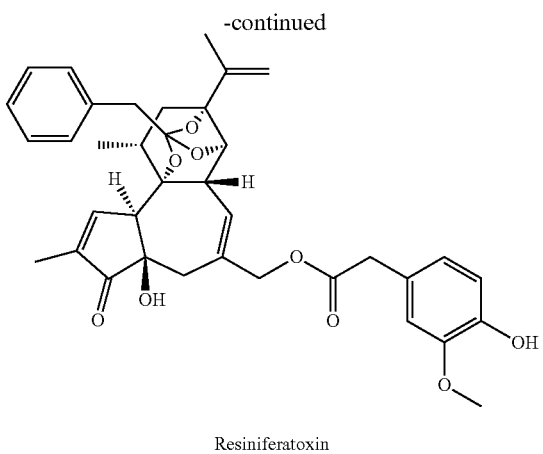

Resiniferatoxin

The vanilloid compounds according to the above embodiments may include all pharmaceutically acceptable salts, hydrates, solvates, crystal forms, diastereomers, conformational isomers (eg. cis and trans isomers), tautomers, prodrugs, metabolites, and enantiomeric forms thereof.

Glycoside Hydrolase

In one embodiment, the term "glycoside hydrolase" means any enzyme that can hydrolyse the glycosidic bond between two or more carbohydrates, or between a carbohydrate and a non-carbohydrate moiety. The glycoside hydrolase can be an enzyme from class 3.2.1, particularly an enzyme from classes 3.2.1.1 to 3.2.1.3. In one embodiment, the glycoside hydrolase is an amylase. The amylase may be selected from α-amylase, β-amylase and 7-amylase, more particularly amylase 2, amylase alpha 1A, amylase alpha 1B, amylase alpha 1C, amylase alpha 2A, amylase alpha 2B. In one embodiment, the amylase is α-amylase.

Amylases are glycoside hydrolases and act on α-1,4-glycosidic bonds. Amylases break down carbohydrates present on the surface glycoproteins of tumour cells. The amylase is selected to enhance the efficacy of treatment of the protease proenzymes by providing a working interrelationship or multifunctional approach to treating cancer. The amylase may be of human, animal, bacterial or plant origin. For example, α-Amylase can be sourced from any one of *Aspergillus oryzae, Bacillus licheniformis*, barley malt, hog pancreas, human pancreas, porcine pancreas, and *Triticum aestivum*.

Cytoplasmic Glycolysis Reduction Agent

In one embodiment, the term "cytoplasmic glycolysis reduction agent" means an agent capable of reducing cytoplasmic glycolysis. In another embodiment, the cytoplasmic glycolysis reduction agent is 2-deoxy-D-glucose, or a pharmaceutically acceptable salt, ester, or prodrug thereof.

The cytoplasmic glycolysis reduction agent is selected to enhance the efficacy of treatment of the protease proenzymes by providing a working interrelationship or multifunctional approach to treating cancer.

The cytoplasmic glycolysis reduction agent may be a blocker or inhibitor of glycolysis, for example oxamate, which is more specific for anaerobically metabolizing cells and can inhibit lactic dehydrogenase, or iodoacetate, which can inhibit glycolysis at glyceraldehyde 3-phosphate dehydrogenase.

The glycolytic inhibitors may include lipophilic analogs or prodrugs of 2-deoxy-D-glucose. Lipophilic analogs include derivatives of hydroxyl groups like esters, ethers, phosphoesters. Others include the removal of the hydroxyl group and replacement with halogens like fluorine or iodine, or with thiol or thioalkyl groups. Liposome formulated 2-deoxy-glucose and its analogs may be provided or enzymatically cleavable derivatives of 2-deoxyglucose. Examples include glucoronides with glycosides at the C-1 position. Lipophilic analogs of 2-deoxy-D-glucose, which may act as prodrugs of 2-deoxy-D-glucose, such as mono and diesters of 2-deoxy-D-glucose, may include examples such as valerate, myristate and palmitate.

The glycolytic inhibitors may also include 6-deoxy-D-glucose, 6-fluoro-D-glucose, 6-O-methyl-D-glucose, 6-thio-D-glucose, 2-deoxy-D-glucose itself and its analogs, 2-deoxy-2-halo-D-glucose, for example 2-bromo-, 2-fluoro- or 2-iodo-D-glucose, 3-deoxy or 3-fluoro-D-glucose or 4-deoxy or 4-fluoro-D-glucose, 2-fluoro or 3-fluoro-glyceraldehydes or glycerates, for example, 3-fluoro-2-phosphoglycerate, 2-fluoro-propionic acid or it salts, 2,2-difluoro-propionic acid, 3-halo-pyruvate, 3-hahlopropionic acid, 2,2-thiomethylacetic acid, 1-deoxy-D-glucose, 5-thio-D-glucose, 3-fluoro-D-glucose and 4-fluoro-D-glucose, 2-fluoro-, 2-iodo-, 2-thio, or 2-methoxy-glyceraldehydes or glycerates, 3-fluoro-, 3,3-difluoro-, enolase 3-iodo-, 3-carboxylo- and 3-thioglycerates.

In an embodiment, the term "cytoplasmic glycolysis reduction agent" means a compound of Formula IV:

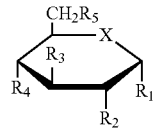

Formula IV or a pharmaceutically acceptable salt, prodrug or ester thereof, wherein:

X is selected from O and S;

$R_1$ is selected from H, halogen, OH, —OC(O)$R_6$;

$R_2$ to $R_4$ are each independently selected from H, halogen, OH, —OC(O)$R_6$;

$R_5$ is selected from halogen, OH, SH, —OC(O)$R_6$; and $R_6$ is $C_{1-20}$alkyl.

Halogen preferably means F, Br or I, more preferably F. Each of the following various embodiments may be taken individually or in any combination thereof. X is O. $R_1$ is OH. $R_2$ is H or F. $R_3$ is OH or F. $R_4$ is OH or F. $R_5$ is OH, F or SH.

In another embodiment, X is O, $R_1$ is selected from OH, $R_2$ is selected from H, Br, F, I, OH, —C(O)—O$R_6$, wherein $R_6$ is selected from $C_{1-20}$alkyl, and $R_3$ to $R_5$ is OH. Preferably, $R_2$ is H.

Additional Active Agents

The pharmaceutical compositions of the first aspect, second aspect, twelfth aspect and thirteenth aspect, may further comprise other active agents. The addition of these active agents may enhance the treatment of cancer. Using this approach, one may be able to achieve therapeutic efficacy with lower dosages of each agent, thus reducing the potential for adverse side effects. One may also be able to reduce undesirable side effects and allow use of higher dosages of each agent. The additional active agents may provide supplemental, additional, or enhanced therapeutic functions.

The pharmaceutical compositions of the first aspect, second aspect, twelfth aspect and thirteenth aspect, may therefore contain one or more of the following additional active agents providing supplemental, additional, or enhanced therapeutic functions:

Antioxidants including vitamin C (ascorbic acid), vitamin E (tocopherols, tocotrienols), polyphenolic antioxidants (resveratrol, flavonoids), carotenoids (lycopene, carotenes, lutein). Resveratrol has shown antitumour and chemopreventive capacity, particularly trans-resveratrol for treating human breast cancer cells.

L-threanine, namely gamma-glutamylethylamide or 5-N-ethyl-glutamine, being a glutamic acid analog or amino acid derivative.

Curcuminoids, curcumin or derivatives thereof.

Beta glucans (1-3, 1-6 beta glucans).

Hydrogen cyanide (HCN)—e.g. LPO generated OSCN ions may accelerate proteolysis.

Phytonutrient extracts including flavanols, xanthophylls, liminoids.

Protease enzyme inhibitors, e.g. aprotinin also known as bovine pancreatic trypsin inhibitor. The use of enzyme inhibitors in combination with the pharmaceutical compositions may facilitate inhibiting any protease enzymes which may be present in the system/body away from the tumour cell and thereby reduce any undesirable effects of such active enzymes.

Growth factors (e.g., BMPs, TGF-P, FGF, IGF).

Cytokines (e.g., interleukins and CDFs).

Antibiotics.

Tumour necrosis factor (TNF), an antibody capable of inhibiting or neutralizing the angiogenic activity of acidic or basic fibroblast growth factor (FGF) or hepatocyte growth factor (HGF), an antibody capable of inhibiting or neutralizing the coagulant activities of tissue factor, protein C, or protein S, an antibody capable of binding to HER2 receptor.

Any other active agent beneficial for treating cancer.

When other additional therapeutic agents are used in combination with the protease proenzyme or active agent of the first and second aspects they may be used in amounts as noted in the Physician Desk Reference (PDR) or as otherwise determined by one of ordinary skill in the art.

Terms

"Activation" in relation to protease proenzymes means the in situ (e.g. in vitro or in vivo) conversion of the protease proenzyme into a form capable of enhancing cell-to-cell adhesion of tumour cells, effect proteolysis of tumour cells, or induce tumour cell apoptosis, differentiation or immunorecognition.

"Apoptosis" is a generally controlled, orderly, careful process of cellular self-destruction that can be triggered by various stimuli. Apoptosis is less invasive than necrosis, which may damage surrounding tissue and cause inflammation.

"Angiogenesis" refers to formation of blood vessels, particularly the proliferation of new capillaries from pre-existing blood vessels. Angiogenesis is necessary for cancer cells to grow into tumours because cancer cells need a significantly greater blood supply than normal cells to survive. Angiogenesis or angiogenic events are involved in a number of pathological processes, notably tumour growth and metastasis, and other conditions in which blood vessel proliferation, especially of the microvascular system, is increased, such as diabetic retinopathy, psoriasis and arthropathies.

The term "pericellular" means at, near, on or within the tissues surrounding a cell. More particularly, the term means at or within the tissues surrounding a tumour cell.

The term "intracellular" means within the cell.

The terms "differentiation", "differentiate" or similar variations thereof mean the ability of cells to become more specialized for different functions. At one level, malignant tumour cells are considered to be cells that have dedifferentiated, which means that they were more specialised cells that have become less specialised, and in the process, the body's ability to limit growth of these malignant cells has become compromised. Differentiation of tumour cells therefore involves a transformation of malignant cells, at least in part, towards a healthy or normal cell type, which means a transformation of the malignant cell in a manner that reduces properties of uncontrolled grow, invasion and/or metastasis.

The term "immunorecognition" means recognition by the immune system and subsequent removal or elimination by the immune system. One role of the immune system is to identify and eliminate tumours. The transformed cells of tumours express antigens that are not found on normal cells. To the immune system, these antigens appear foreign, and their presence causes immune cells to attack the transformed tumour cells. Some forms of cancer cells also have the capability to prevent or reduce immunorecognition.

The term "metastasis", "metastasized" or similar variations thereof refer to the spread of a disease from one organ or part of the body to another non-adjacent organ or part of the body. Malignant tumour cells and infections have the capacity to metastasize. For example, cancer cells can break away or escape from a primary tumour, enter lymphatic and blood vessels, circulate through the bloodstream, and become redeposited elsewhere in the body. A new tumour formed from a primary tumour following metastasis is called a secondary or metastatic tumour, and is comprised of the same cells as the primary or original tumour. For example, breast cancer metastasizing to the lungs forms a secondary tumour comprising abnormal breast cells, not abnormal lung cells, and is called metastatic breast cancer, not lung cancer.

The term "malignancy", "malignant" or similar variations thereof refers to the tendency of cancer cells and tumours to continue to grow and develop, which involves characteristic properties of anaplasia, invasiveness, and metastasis. For example, a malignant tumour may be contrasted with a non-cancerous benign tumour in that a malignancy is not self-limited in its growth, is capable of invading into adjacent tissues, and may be capable of spreading to distant tissues (metastasizing), while a benign tumour has none of those properties.

"Anaplasia" refers to a reversion of differentiation in cells, which is characteristic of malignant tumours. This term covers an increased capacity for multiplication. Anaplasia involves lack of differentiation, increased dedifferentiation or increased loss of structural and functional differentiation present in normal cells.

"Proteolysis" is the directed degradation (digestion) of proteins by cellular enzymes called proteases or by intramolecular digestion. More particularly, proteolysis is the breaking down of proteins by protease enzymes cleaving, by hydrolysis, the amide/peptide bond in the proteins.

The terms "cell-to-cell adhesion", "cell adhesion molecules" or similar terms thereof refer to a range of known cell-to-cell adhesion molecules that are generally located at the outer surface of a cell and are involved in binding of one cell with another cell or cells, E-cadherin and β-catenin being examples thereof. Different cell types may have alternative forms of these molecules. These molecules may additionally be involved in adhesion with the extracellular matrix. Other cell-to-cell adhesion molecules may be selected from cadherin, integrin, selectin, and immunoglubulin cell adhesion protein families.

The terms "homologue" and "functional equivalent" shall be taken to include other proteins or variants such as known molecules within the same protein family, in addition to recombinant molecules.

By "up-regulating" it will be understood that this includes increasing the level of expression or activity of the molecule in relation to a pre-determined reference level. This may be an increase of at least 5% above the reference level. Particularly preferred, however, would be up-regulation by at least 10%, 20% 30%, 40% or 50% or more in relation to the reference level. The reference level may be determined by a variety of means, such as according to the expression or activity of the molecule prior to treatment, or according to the normal or expected level for a given cell type.

Methods and Uses

The use of the fifth to ninth aspects or forteenth aspect, or method of the tenth aspect or fifthteenth aspect, may involve one or more of the following effects: reduction in the reoccurrence of malignant tumours, reduction in metastasis of malignant tumours, reduction in number or size of tumours, differentiation of tumour cells, expression of β-catenin and E-cadherin in malignant tumours to facilitate cell-to-cell adhesion and reduction in metastasis, reduction in tumour cells ability to prevent immunorecognition.

An embodiment provides a method of differentiating a cancer cell in a subject comprising administering to the subject a therapeutically effective amount of a protease proenzyme and an active agent of the first and second aspects for a time and under conditions sufficient to induce differentiation in the cancer cell. The use of the fifth and sixth aspect and the method of the seventh aspect may involve differentiation of a cancer cell. In one particular embodiment, the differentiation of cancer cells is differentiation of colon carcinoma cells.

In one embodiment, the use of the fifth to ninth aspects or forteenth aspect, or method of the tenth aspect or fifthteenth aspect, is beneficial when used for the treatment of metastatic cancer. Metastasis is the stage of cancer wherein the disease spreads to other parts of the body. The prevention or delay of metastasis is therefore particularly important as this stage is accompanied by a marked reduction in the success of other treatments and a reduction in survival of the subject. In another embodiment there is provided a safe and effective means of preventing, delaying or otherwise ameliorating cancer metastasis by up-regulating cell-cell adhesion molecules in a cancer cell through the administration to the subject an effective amount of a protease proenzyme and an active agent of the first and second aspects.

"Treating" or "treatment" refers to both therapeutic treatment and prophylactic or preventative measures, wherein the aim is to prevent, ameliorate, reduce or slow down (lessen) cancer or the spread (metastasis) thereof.

"Preventing", "prevention", "preventative" or "prophylactic" refers to keeping from occurring, or to hinder, defend from, or protect from the occurrence of a condition, disease, disorder, or phenotype, including an abnormality or symptom. A subject in need of prevention may be prone to develop the condition.

The term "ameliorate" or "amelioration" refers to a decrease, reduction or elimination of a condition, disease, disorder, or phenotype, including an abnormality or symptom. A subject in need of treatment may already have the condition, or may be prone to have the condition or may be one in whom the condition is to be prevented.

The "subject" includes a mammal. The mammal may be a human, or may be a domestic, zoo, or companion animal. While it is particularly contemplated that the methods of the invention are suitable for medical treatment of humans, they are also applicable to veterinary treatment, including treatment of companion animals such as dogs and cats, and domestic animals such as horses, cattle and sheep, or zoo animals such as felids, canids, bovids, and ungulates. A subject may be afflicted with cancer or other disorder, or may not be afflicted with cancer or other disorder (i.e., free of detectable disease).

The term "therapeutically effective amount" refers to an amount of composition, or agent or compound in the composition, capable of treating, preventing or ameliorating cancer or the spread (metastasis) thereof. A therapeutically effective amount may be determined empirically and in a routine manner in relation to treating cancer, and will result in increased life expectancy.

The use of the fifth to ninth aspects or forteenth aspect, or method of the tenth aspect or fifthteenth aspect, may involve the treatment of neoplasms and related conditions, cancers, tumours, malignant and metastatic conditions. Tissues and organs associated with solid tumours and metastases which can be treated with a protease proenzyme and an active agent of the first and second aspects include, but are not limited to, biliary tract, bladder, blood, brain, breast, cervix, colon, endometrium, esophagus, head, neck, kidney, larynx, liver, lung, medulla, melanin, ovarian, pancreas, prostate, rectum, renal, retina, skin, stomach, testes, thyroid, urinary tract, and uterus.

The use of the fifth to ninth aspects or forteenth aspect, or method of the tenth aspect or fifthteenth aspect, are particularly suited to treating cancers and metastatic carcinomas of the following types: pancreatic cancer, oesophageal cancer, colon cancer, bowel cancer, prostate cancer, ovarian cancer, stomach cancer, breast cancer, malignant melanoma or lung cancer.

The use of the fifth to ninth aspects or forteenth aspect, or method of the tenth aspect or fifthteenth aspect, may provide a multiple effect approach to treating cancer, for example by increasing in tumour cells apoptosis, cell-to-cell adhesion, differentiation and immunogenicity (targeting and removal by immune system). It is therefore beneficial to conduct treatment in the absence of any other treatments that may suppress or harm the immune system.

In one embodiment, the use of the fifth to ninth aspects or forteenth aspect, or method of the tenth aspect or fifthteenth aspect, involve treatment of subjects having low levels of expression of E-cadherin and β-catenin. Further patient groups may also be identified that are particularly suited to treatment according to the method or use of the above aspects.

The use of the fifth to ninth aspects or forteenth aspect, or method of the tenth aspect or fifthteenth aspect, can be supplemented by other conventional anti-cancer therapeutic approaches directed to treatment or prevention of proliferative disorders (e.g., tumour). For example, such methods can be used in prophylactic cancer prevention, prevention of cancer recurrence and metastases after surgery, and as an adjuvant of other conventional cancer therapy.

Pharmaceutical Compositions, Formulations and Routes of Administration

The pharmaceutical compositions of the first and second aspects, or twelfth or thirteenth aspects, may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The pharmaceutical compositions of the of the first and second aspects, or twelfth or thirteenth aspects, may be administered by any suitable means, for example, orally, such as in the form of tablets, capsules, granules or powders; sublingually; buccally; parenterally, such as by subcutaneous, intravenous, intramuscular, or intracisternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. They may, for example, be administered in a form suitable for immediate release or extended release, for example, by the use of devices such as subcutaneous implants, encapsulated spheroids or osmotic pumps.

In addition to primates, such as humans, a variety of other mammals can be treated according to the methods of the tenth aspect. For instance, mammals including, but not limited to, cows, sheep, goats, horses, dogs, cats, guinea pigs, rats or other bovine, ovine, equine, canine, feline, rodent or murine species can be treated.

The term "composition" as used herein is intended to encompass a product comprising the protease proenzyme and one or more active agents, and optionally one ore more additional active agents, as well as any product which results, directly or indirectly therefrom.

The term "pharmaceutically acceptable" as used herein means the carrier, diluent or excipient is not deleterious to the recipient thereof.

The terms "administration of" and or "administering" should be understood to mean providing to an individual in need of treatment.

The pharmaceutical compositions of the first and second aspects, or twelfth or thirteenth aspects, and preparations or formulations thereof may be prepared by admixing together the components of the composition, namely the protease proenzymes with one or more active agents, which include a selenium compound and/or a vanilloid compound. In a further embodiment, the components may include an additional active agent as described herein. The admixing may be performed sequentially or simultaneously.

The pharmaceutical compositions of the first and second aspects, or twelfth or thirteenth aspects, may conveniently be presented in dosage unit form and may be prepared by any of the methods well known in the art of pharmacy. All methods include the step of bringing the active agents and protease proenzyme into association with the carrier which constitutes one or more accessory ingredients. In general, the pharmaceutical compositions are prepared by uniformly and intimately bringing the active agents and protease proenzymes into association with a liquid carrier or a finely divided solid carrier or both, and then, if necessary, shaping the product into the desired formulation. The active agents and protease proenzymes are provided in a dosage unit form in an amount sufficient to produce the desired effect upon the process or condition of diseases after single or repeated administration.

The pharmaceutical compositions of the first and second aspects, or twelfth or thirteenth aspects, may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the protease proenzyme and active agent of the first and second aspects in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the protease proenzyme and active agent of the first and second aspects are mixed with an inert solid diluent, for example, calcium carbonate, calcium phosphate or kaolin, or as soft gelatin capsules wherein the protease proenzyme and active agent of the first and second aspects are mixed with water or an oil medium, for example peanut oil, liquid paraffin, or olive oil.

Aqueous suspensions contain the active agent and protease proenzyme in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active agent and protease proenzyme in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These may be preserved by the addition of an anti-oxidant such as ascorbic acid.

Dispersible powders and granules suitable for preparation of an aqueous suspension by the addition of water provide the protease proenzyme and active agent of the first and second aspects in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the first and second aspects, or twelfth or thirteenth aspects, may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. They may also contain a demulcent, a preservative and flavoring and coloring agents.

The pharmaceutical compositions of the first and second aspects, or twelfth or thirteenth aspects, may be in the form of a sterile injectable aqueous or oleagenous suspension. This suspension may be formulated according to the known art using those suitable dispersing or wetting agents and suspending agents which have been mentioned above. The pharmaceutical compositions of the first and second aspects may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

In a particular embodiment, the pharmaceutical compositions of the first and second aspects, or twelfth or thirteenth aspects, are formulated as suppositories for rectal administration of the drug. These formulations can be prepared by mixing the protease proenzyme and active agent of the first and second aspects with a suitable non-irritating excipient which is solid at ordinary temperatures but liquid at the rectal temperature and will therefore melt in the rectum to release the drug. Such materials include cocoa butter and polyethylene glycols. Rectal administration may be used to elimate entero-hepatic first pass effect in the gastro-intestinal tract related to oral administration of enzymes.

The pharmaceutical compositions of the first and second aspects, or twelfth or thirteenth aspects, may also be formulated in liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolisable lipid capable of forming liposomes can be used. The liposome formulation may contain stabilisers, preservatives, excipients and the like. The preferred lipids are the phospholipids and phosphatidyl cholines, both natural and synthetic. Methods to form liposomes are known in the art.

The pharmaceutical compositions of the first and second aspects, or twelfth or thirteenth aspects, may be included in a container, pack, or dispenser together with instructions for administration. The protease proenzymes and active agents, and optionally additional active agent, of the pharmaceutical composition may be provided as separated components in the container, pack, or dispenser, to be taken separately or together at the same or different time in the use of the fifth to ninth aspects or method of the tenth aspect.

Dosages and Therapeutically Effective Amounts

An appropriate dosage level for the pharmaceutical compositions of the first and second aspects, or twelfth or thirteenth aspects, will generally be about 0.01 to 500 mg per kg patient body weight per day which can be administered in single or multiple doses. It may be about 0.1 to about 250 mg/kg per day; or about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05-0.5, 0.5-5 or 5-50 mg/kg per day. For oral administration, the pharmaceutical compositions of the first and second aspects may be provided in the form of tablets containing 1.0-4000 milligrams of the protease proenzyme and active agent, particularly 1.0, 5.0, 10.0, 15.0. 20.0, 25.0, 50.0, 75.0, 100.0, 150.0, 200.0, 250.0, 300.0, 400.0, 500.0, 750.0, 1000, 1500, 2000, 2500, 3000, 3500, and 4000 milligrams of the protease proenzyme and active agent for the symptomatic adjustment of the dosage to the patient to be treated. The pharmaceutical compositions as described herein may be administered on a regimen of 1 to 4 times per day, once or twice per day, or once daily, with reduced requirements of administration generally leading to greater compliance.

The dosage may vary widely depending on whether a single administration form of the composition is given and whether the vanilloid compound is included as an active agent in the composition or tablet (or other administration form). Typically, vanilloid compounds such as a capsiate or capsaicin may be provided in relatively large dosages of between 0.1 to 5 g, and more particularly about 1-2 g per administration.

A suitable single administration for an embodiment of the pharmaceutical compositions as described herein may comprise:

Trypsinogen in an amount of between 1-100 mg, particularly 2-50 mg, more particularly (in mg) 1.0, 2.5, 5.0, 7.5, 10.0, 15.0. 20.0, 25.0, 30.0, 40.0, 50.0;

Chymotrypsinogen in an amount of between 1-100 mg, particularly 2-50 mg, more particularly (in mg) 1.0, 2.5, 5.0, 7.5, 10.0, 15.0. 20.0, 25.0, 30.0, 40.0, 50.0;

Selenium compound in an amount of between 0.01-3 mg, particularly 0.1-1 mg, more particularly (in mg) 0.1, 0.2, 0.3, 0.4, 0.5, 0.6, 0.7, 0.8, 1.0;

Vanilloid compound in an amount of between 0.1-4000 mg, particularly 0.5-3000 mg, more particularly (in mg) 500, 1000, 1500, 2000, 2500, 3000;

Amylase in an amount of between 0.1-100 mg, particularly 1-15 mg, more particularly 1.0, 2.0, 3.0, 4.0, 5.0, 7.5, 10.0, 15.0;

2-Deoxy-D-glucose in an amount of between 0.1-100 mg, particularly 1-15 mg, more particularly 1.0, 2.0, 3.0, 4.0, 5.0, 7.5, 10.0, 15.0.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Suitable dosage levels for the various components (if present) of an embodiment of the the pharmaceutical compositions as described herein, may comprise:

Chymotrypsinogen in an amount of at least 0.2 mg/kg, or in a range of 0.2-5 mg/kg, in a range of 0.5-2.0 mg/kg, or about 0.8 mg/kg;

Trypsinogen in an amount of less than 0.5 mg/kg, or in a range of 0.01-0.4 mg/kg, or in a range of 0.05-0.20 mg/kg, or about 0.1 mg/kg;

Methylselenocysteine in an amount of at least 0.0001 mg/kg, or in a range of 0.001-0.01 mg/kg, in a range of 0.002-0.005 mg/kg, or about 0.003 mg/kg;

Capsiate in an amount of at least 1 mg/kg, or in a range of 5-500 mg/kg, or in a range of 10-100 mg/kg, or about 30 mg/kg;

Amylase in an amount of at least 0.001 mg/kg, or in a range of 0.01-0.1 mg/kg, in a range of 0.02-0.05 mg/kg, or about 0.03 mg/kg;

2-Deoxy-D-glucose in an amount of at least 1 mg/kg, or in a range of 5-500 mg/kg, or in a range of 10-100 mg/kg, or about 30 mg/kg.

A suitable ratio by wt % for the various components (if present) of an embodiment of the pharmaceutical compositions as described herein, may comprise: Chymotrypsinogen:Trypsinogen:Amylase:2-Deoxyglucose:Capsiate:Methylselenocysteine in a ratio of 200-400:25-75:5-15:5,000-20,000:5,000-20,000:0.1-10, or about 300:50:10:10,000:10,000:1.

Suitable concentrations for the various components (if present) of the pharmaceutical compositions as described herein, which may be particularly effective if present at or near the surface of a tumour cell, may comprise:

Chymotrypsinogen in a concentration of at least 0.5 mg/ml, or in a range of 1-2 mg/ml;

Trypsinogen in a concentration of less than 0.25 mg/ml, or in a range of 0.1-0.2 mg/ml;

Amylase in a concentration of at least 0.01 mg/ml, or in a range of 0.02-0.1 mg/ml;

Vanilloid compound in a concentration of at least 5 mg/ml, or in a range of 10-20 mg/ml;

2-Deoxy-D-glucose in a concentration of at least 5 mg/ml, or in a range of 10-20 mg/ml;

Selenium compound in a concentration of less than 0.01 mg/ml, or in a range of 0.001-0.005 mg/ml.

Further enhanced activity may be provided for the pharmaceutical compositions if the concentration, or relative amount, of the selenium compound is kept within a specific range when present. The concentration of methylselenocysteine may be less than 0.01 mg/ml, less than 0.005 mg/ml, less than 0.001 mg/ml, or less than 0.0005 mg/ml, or in the range of 0.0005 to 0.01 mg/ml, or in the range of 0.001 to 0.005 mg/ml.

Chymotrypsinogen/Trypsinogen Proenzyme Formulation

A pharmaceutical composition is provided comprising a first and a second protease proenzyme capable of activation at or near a surface of a tumour cell to enhance cell-to-cell adhesion of tumour cells, effect proteolysis of tumour cells, or induce tumour cell apoptosis, differentiation or immunorecognition, wherein the first protease proenzyme is chymotrypsinogen and the second protease proenzyme is trypsinogen, and the weight ratio of chymotrypsinogen:trypsinogen is in the range of between 4:1 to 8:1. The pharmaceutical composition may further comprise one or more active agents according to any of the embodiments described above.

In one embodiment, the weight ratio of chymotrypsinogen:trypsinogen is in the range of between 5:1 to 7:1, preferably 6:1.

Active Agent Formulation

A pharmaceutical composition is provided comprising a first and second active agent each capable of inducing intracellular activity in tumour cells, wherein the first active agent is a selenium compound and the second active agent is a cytoplasmic glycolysis reduction agent.

In an embodiment, the intracellular activity is tumour cell apoptosis, immunorecognition or differentiation. The selenium compound and/or cytoplasmic glycolysis reduction agent mean a compound as described in the above embodiments. Preferably, the selenium compound is methylselenocysteine. Preferably, the cytoplasmic glycolysis reduction agent is 2-Deoxy-D-glucose.

The pharmaceutical composition may further comprise a protease proenzyme according to any one of the embodiments described above. The pharmaceutical composition may further comprise an active agent selected from a vanilloid compound and a glycoside hydrolase according to any one of the embodiments described above.

Screening and Identification Methods

A further embodiment provides a method of identifying an agent useful in the up-regulation of expression of cell-cell adhesion molecules of a cancer cell(s), the method comprising contacting a cancer cell or cell-cell adhesion molecules of the cancer cell with a composition as hereinbefore described, adding a test agent, monitoring or measuring the level of cell-cell adhesion or expression of cell-cell adhesion molecules and assessing the effect of the test agent. Small compound chemical library screening and antibody display panning are examples of available sources of test agents that may be readily assessed using this type of procedure. For instance, High Throughput Chemical Screening (HTS) may be readily utilised to screen many thousands of molecules such as chemicals or antibodies using robotics and microtitre plates. In order to develop such a screen it is necessary to provide a suitable screening assay to be performed during the screen. This screening assay would incorporate a cell-cell adhesion molecule or a cancer cell such as a metastatic cancer cell. The assay would include reference cells and optionally offer the comparison of the addition of test compounds, proenzymes and optional enzymes. Similarly, phage display techniques may readily be utilised to provide a high throughput method for assessment of potential agents useful in the up-regulation of expression of cell-cell adhesion molecules of cancer cells.

General Points

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

All publications mentioned in this specification are herein incorporated by reference.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

As used in the specification the singular forms "a" "an" and "the" include plural references unless the context clearly dictates otherwise. Thus, for example, reference to "a solvent" includes mixtures of solvents, reference to "an agent" includes mixtures of two or more such agents, and the like.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

Materials and Methods

In order that the nature of the present invention may be more clearly understood, preferred forms of the invention will now be described by reference to the following non-limiting experiments and examples.

Experiment 1: Identification of Mechanism of Action of Proenzymes

An investigation of the effects and mechanisms involved with treating cancer cell lines with pharmaceutical compositions comprising trypsinogen and chymotrypsinogen was conducted on three different types of cell lines. The cell lines used were Panc1: a human pancreatic ductal carcinoma cell line, Caco2: a human colon adenocarcinoma cell line, and OE33: an oesophageal adenocarcinoma cell line.

All cell lines were maintained in T 75 culture flasks at 37 C in a humidified atmosphere containing 5% $CO_2$. Media used to maintain the cells in culture were: Dulbecco's modified Eagle medium (DMEM) for PANC1; Eagle's Minimum Essential Medium (EMEM) for CaCO2 and RPMI Medium 1640 for OE33 (Invitrogen, Merelbeke, Belgium). All media was supplemented with 10% foetal bovine serum (FBS; Invitrogen), 100 IU/ml penicillin (Invitrogen), 100 µg/ml streptomycin (Invitrogen) and 2 mM L-Glutamine (Sigma).

Trypsinogen (Try) and α-chymotrypsinogen (Chy) can be purchased from Sigma-Aldrich (St. Louis, Mo.) and sourced from bovine pancreas origin. The formulations were provided in phosphate buffered saline (PBS, Sigma) and diluted where necessary with 10% foetal bovine serum.

A range of formulations were prepared and tested, and were coded according to Table 1 below.

TABLE 1

Formulation Codes

| Formulation Code | Combination |
| --- | --- |
| B: | Chymotrypsinogen; Trypsinogen and Elastase |
| C: | Placebo |
| J: | Chymotrypsinogen; Trypsinogen and α-Amylase |
| T: | Chymotrypsinogen and Trypsinogen |

Various concentrations were prepared to gain an understanding of the concentration of the formulation effecting cell viability. Based on an original starting concentration of each mixture nominated as 1×, six different dilutions of each of the formulations were coded and made up as shown in Table 2 below.

TABLE 2

| Dilution | Enzyme concentrations |
| --- | --- |
| 0.25x | Trypsinogen: 0.00325 mg/ml |
| | α-Chymotrypsinogen: 0.00325 mg/ml |
| | α-Amylase: 0.00075 mg/ml |
| | Elastase: 0.0005 mg/ml |

TABLE 2-continued

| Dilution | Enzyme concentrations |
| --- | --- |
| 0.5x | Trypsinogen: 0.0065 mg/ml |
| | α-Chymotrypsinogen: 0.0065 mg/ml |
| | α-Amylase: 0.015 mg/ml |
| | Elastase: 0.001 mg/ml |
| 1x | Trypsinogen: 0.013 mg/ml |
| | α-Chymotrypsinogen: 0.013 mg/ml |
| | α-Amylase: 0.003 mg/ml |
| | Elastase: 0.002 mg/ml |
| 1.25x | Trypsinogen: 0.0162 mg/ml |
| | α-Chymotrypsinogen: 0.0162 mg/ml |
| | α-Amylase: 0.00375 mg/ml |
| | Elastase: 0.0025 mg/ml |
| 2.5x | Trypsinogen: 0.0325 mg/ml |
| | α-Chymotrypsinogen: 0.0325 mg/ml |
| | α-Amylase: 0.0075 mg/ml |
| | Elastase: 0.005 mg/ml |
| 5x | Trypsinogen: 0.065 mg/ml |
| | α-Chymotrypsinogen: 0.065 mg/ml |
| | α-Amylase: 0.015 mg/ml |
| | Elastase: 0.01 mg/ml |

To obtain a correlation between the optical density and the cell number, a known cell number was seeded and after the cells were attached, the cells were stained with Sulforhodamine B (SRB). This method gave data of absorbance or optical density of the cells after the staining, and allowed the development of standard curves to convert absorbance into cell number for each cell type as is shown in FIG. 1.

Effect of Formulations on Test Cell Lines

To determine the cytotoxic effect of the formulations on the test cell lines, the cells were plated and treated with the formulations. The effect was assessed by protein assay and microscopy.

SRB protein staining was used to test the effect of different formulations on cell proliferation. The dye binds to basic amino acids of cellular proteins and through colourimetric evaluation provides an estimate of total protein mass, which is related to cell number. The half maximal inhibitory concentration ($IC_{50}$) values were determined from log-linear dose-response curves for each formulation.

Day 1: Cells were seeded in 24 well culture dishes at low density (1000-3000 cells per well depending on the cell type). The cell lines used were Panc1: Human pancreatic ductal carcinoma cell line, Caco2: Colorectal cancer cell line, OE33: Oesophageal cancer cell line and HEK293. HEK293 is a transformed cell line derived from human embryonic kidney. One 24 well culture plate of each cell line was used to test each of the different combination formulations. Each of the formulation dilutions was tested in four wells. One 24 well culture plate of each cell line was used as control, the same number of cells was seeded and the medium was change as the treated cells.

Day 2: The medium was removed and fresh medium containing the different dilutions of the formulations was added to the cells.

Day 5: The medium was again removed and fresh medium containing the different dilutions of the formulations was added to the cells.

Day 6 or 7: Cells were fixed with 10% cold (4° C.) trichloroacetic acid (TCA). Following gentle aspiration of the medium, TCA was added to the wells. The plates were left for 30 min at 4° C., washed 3 times with deionized water and left to dry at room temperature for at least 24 h.

Fixed cells were stained with SRB as follows. 1 ml of 0.4% SRB (w/v in 1% acetic acid solution) was added to each well and left at room temperature for 20 min. SRB was removed and the plates washed 3 times with 1% acetic acid before air drying. Bound SRB was solubilized with 500 ml of 10 mM Tris-base solution and plates were left on a plate shaker for at least 10 min. 100 ml of each well was transferred to a well of a 96-well plate, this was done 3 times per well of the 24-well plate. Absorbance was read in a 96-well plate reader at 492 nm.

Effect of the Formulations on Oesophageal Cancer Cell Line (OE33) Viability

OE33 cells were seeded at a density of 3000 cells/ml (Day 1). The cells were treated with 0.25×; 0.5×; 1×; 1.25×; 2.5× and 5× of the different formulations on Day 2 and Day 5. Cells were fixed at Day 7.

Microscopically, treatment with formulation B caused cells to display a rounded morphology, also causing cell shrinkage and increased detachment. Thus, after 48 hours incubation only a few cells remained attached and cell debris and floating cells were visible in the medium (FIG. 2).

Figure 3:
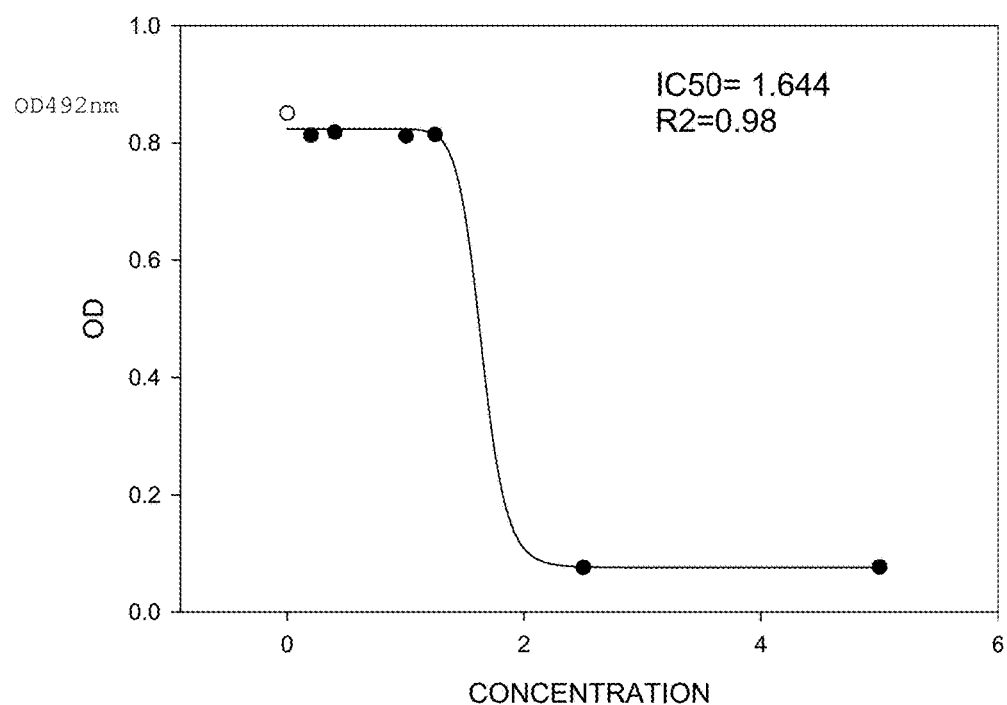
FIG. 3 shows a graph of OE33 cells treated with a range of concentrations of proenzyme reference formulation B.

The results observed by optical microscopy were corroborated by the SRB protein-staining assay. Table 3 shows the mean value for 4 replicate wells of each treatment, the effect on cell death of formulation B was dependent of the concentration; 2.5× and 5× kill all the cells in the wells. The $IC_{50}$ value was obtained by plotting the absorbance against the concentration, as is shown in FIG. 3.

The control, shown as the OD for concentration 0, was the mean of 24 replicate wells. At the time of the fixation all the 24 wells of the control plate were completely confluent.

TABLE 3

Effect of different concentrations of formulation B on OE33 cells

| CONC (1) | OE33 B (1) |
|---|---|
| 0 | 0.851 |
| 0.4 | 0.819 |
| 0.2 | 0.814 |
| 1 | 0.812 |
| 1.25 | 0.815 |
| 2.5 | 0.076 |
| 5 | 0.076 |

Effect of the Formulations on Human Pancreatic Ductal Carcinoma (Panc1) Cells

Panc1 cells were seeded at a density of 20,000 cells/ml (day 1). The cells were treated with 0.25×; 0.5×; 1×; 1.25×; 2.5× and 5× of the different formulations on day 2 and day 4. Cells were fixed at day 5. The control formulation C at the concentrations tested did not have any effect on Panc1 cell viability (data not shown). Microscopically, formulations B, J and T showed an effect on cell viability, cells treated with 2.5× and 5× of these formulations rounded up and died (data not shown).

Figure 4A:
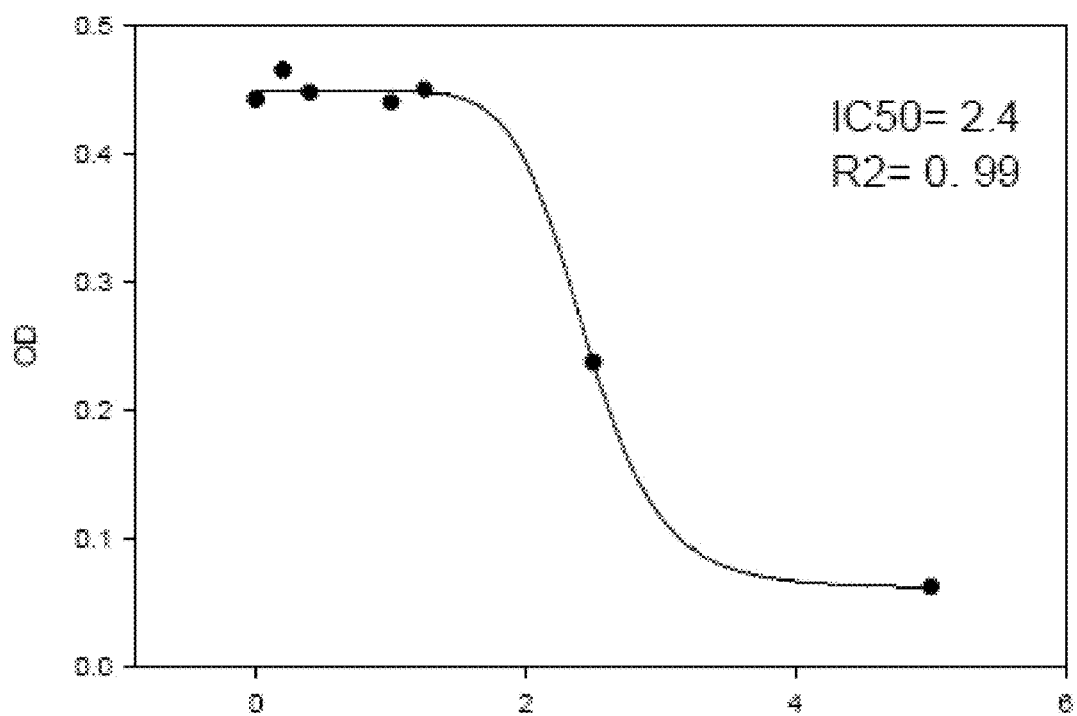
FIGS. 4A-C each show a graph of Panc1 cells treated with proenzyme reference formulations B, J and T, respectively.
Figure 4B:
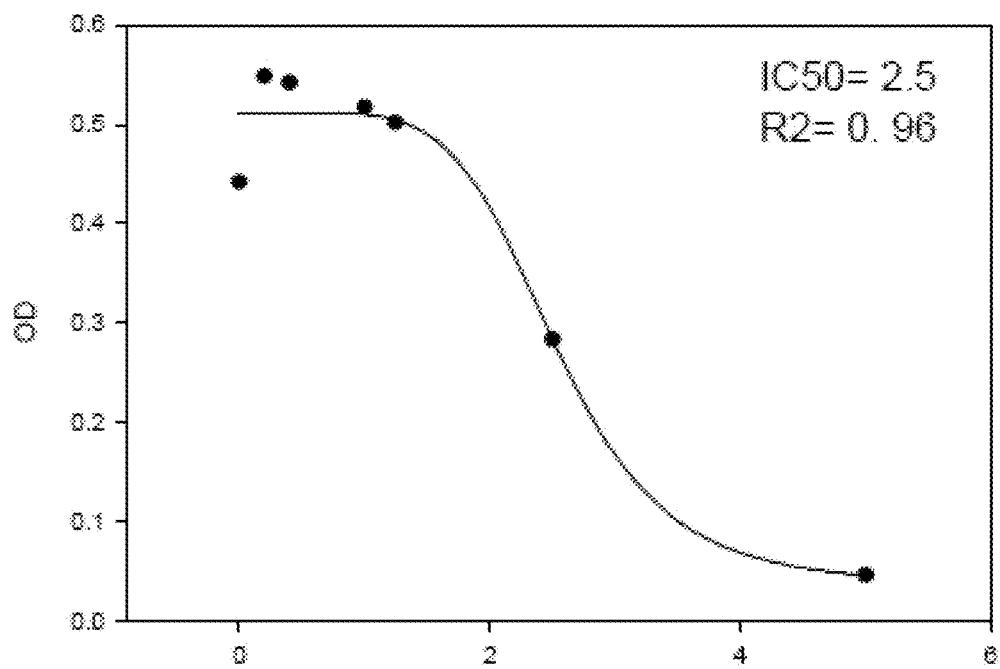
Figure 4C:
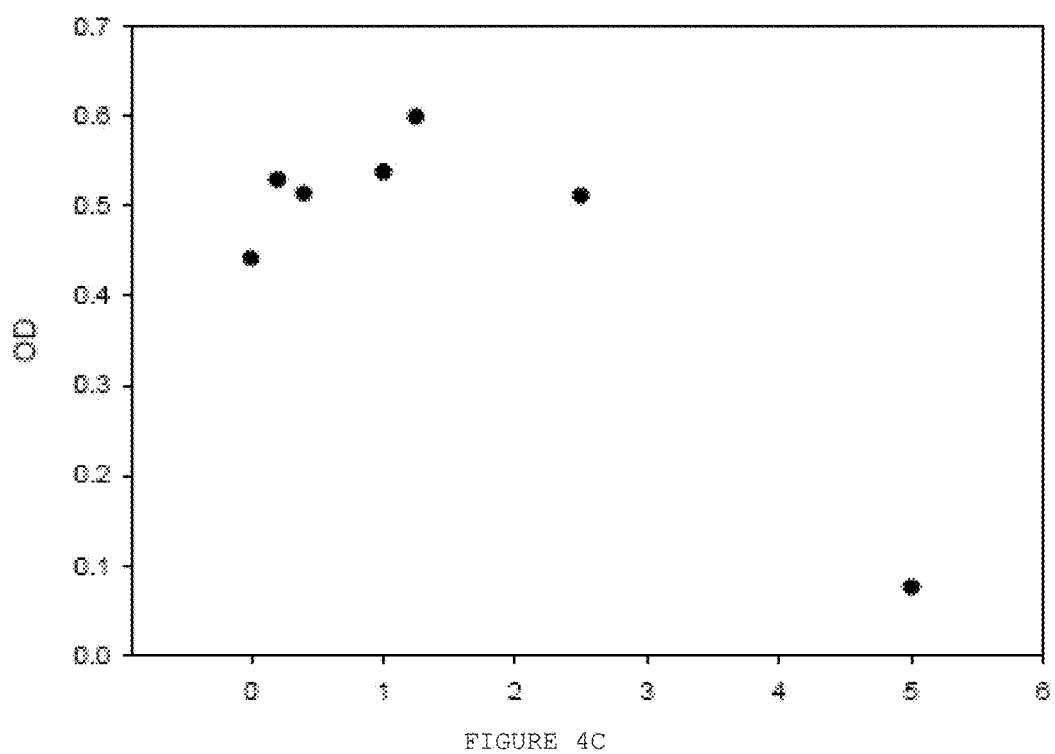
Figure 6A:
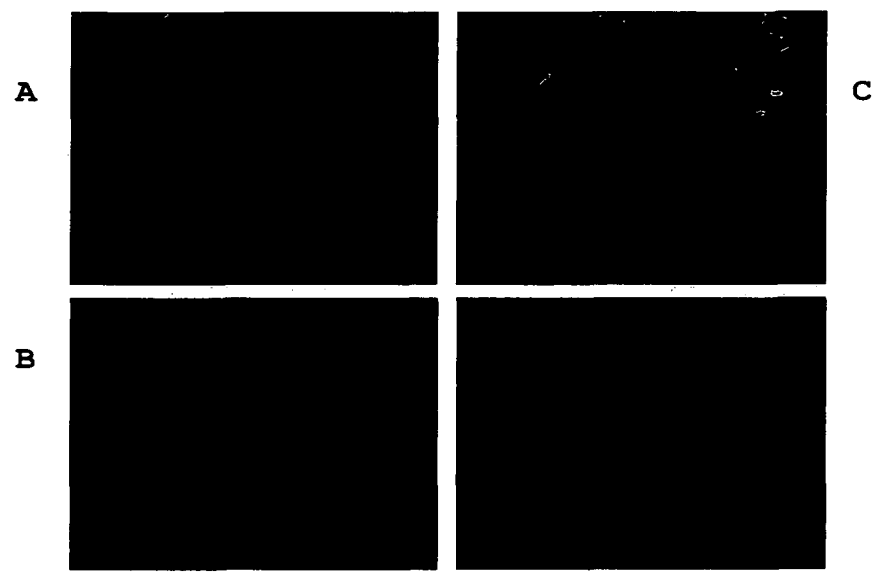
FIGS. 6A and 6B each provide photomicrographs showing the up-regulation of β-catenin in OE33 cells following treatment with proenzyme reference formulation J.
Figure 6B:
Figure 7A:
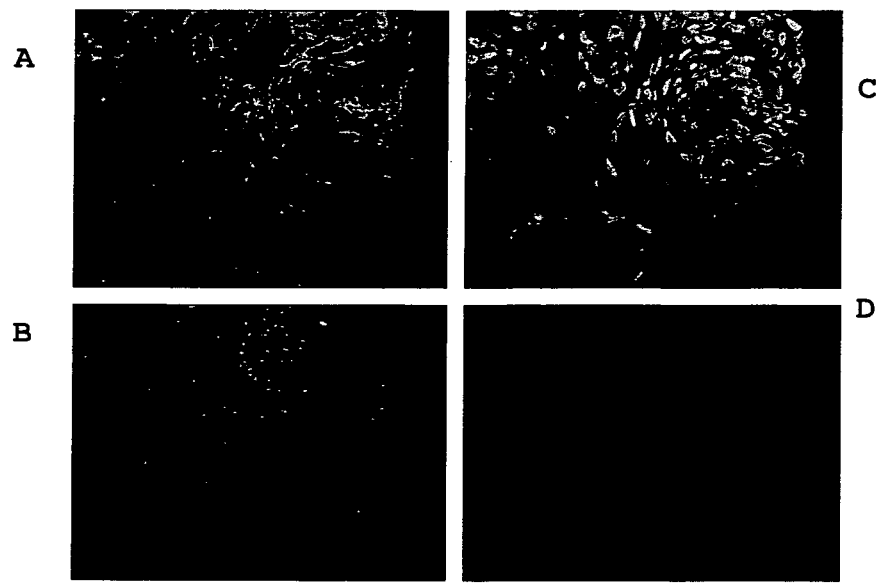
FIGS. 7A and 7B each provide photomicrographs showing the up-regulation of E-Cadherin in OE33 cells following treatment with proenzyme reference formulation J.
Figure 7B:
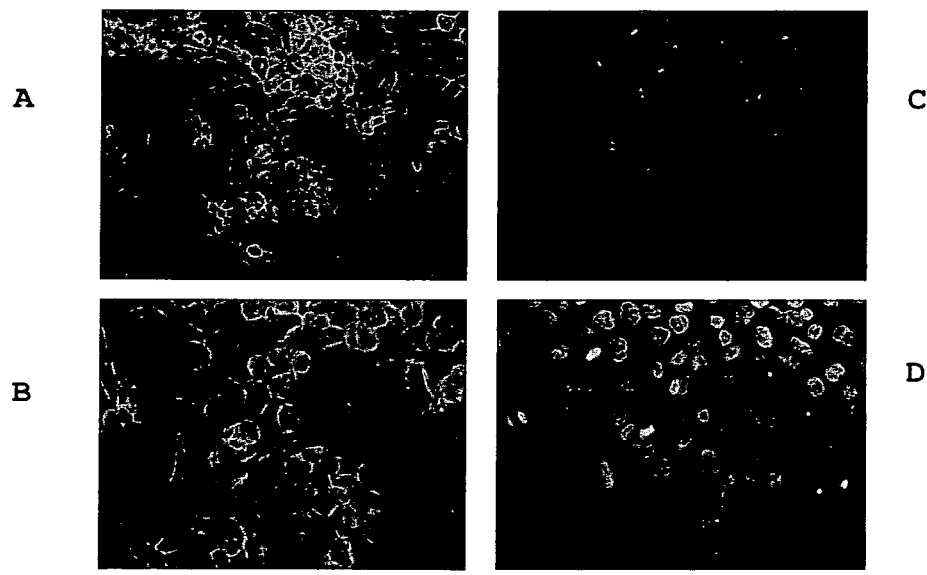
Figure 10A:
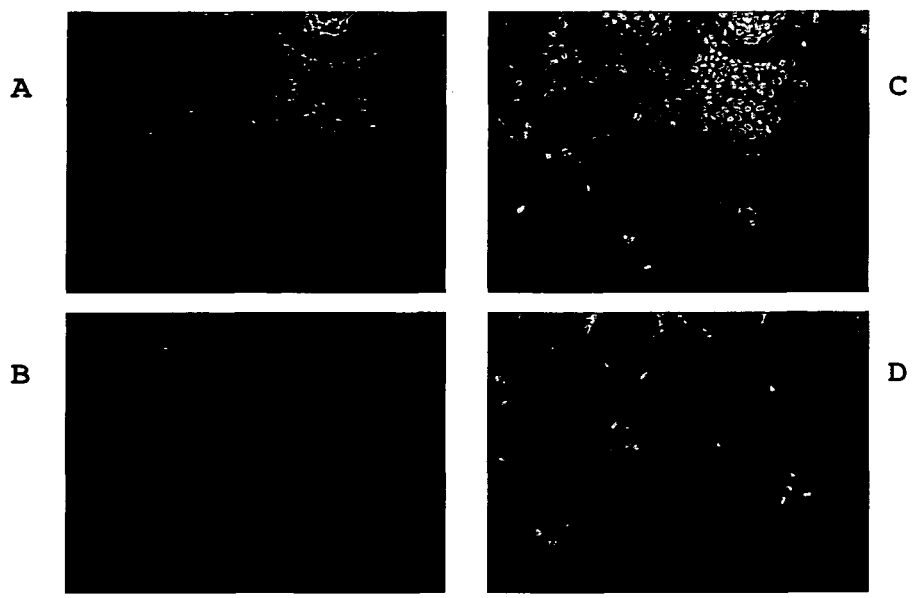
FIGS. 10A and 10B each provide photomicrographs showing the up-regulation of E-Cadherin in Caco2 cells following treatment with proenzyme reference formulation J.
Figure 10B:
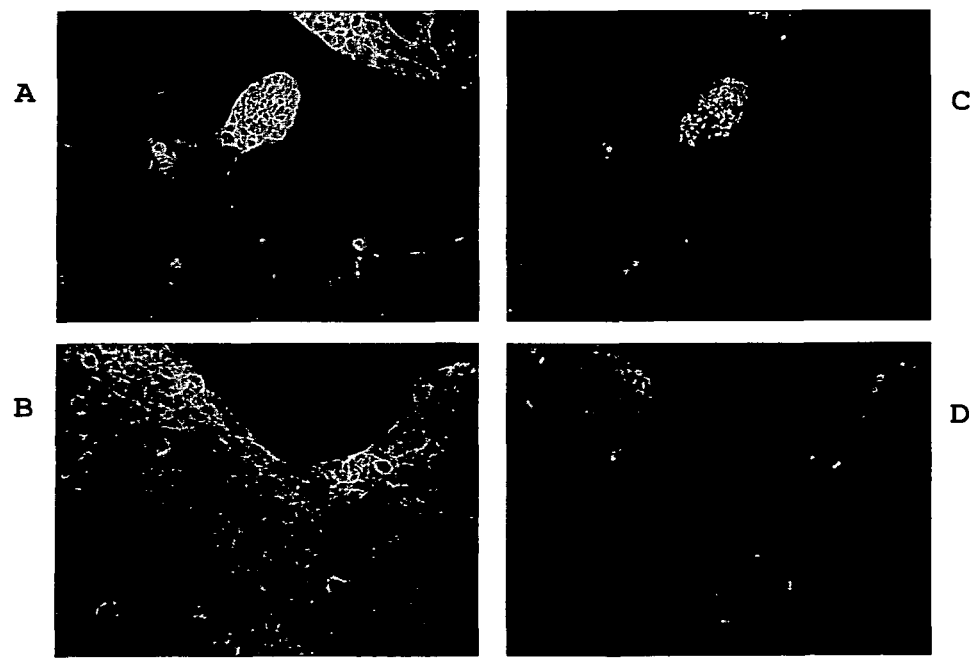
Figure 11A:
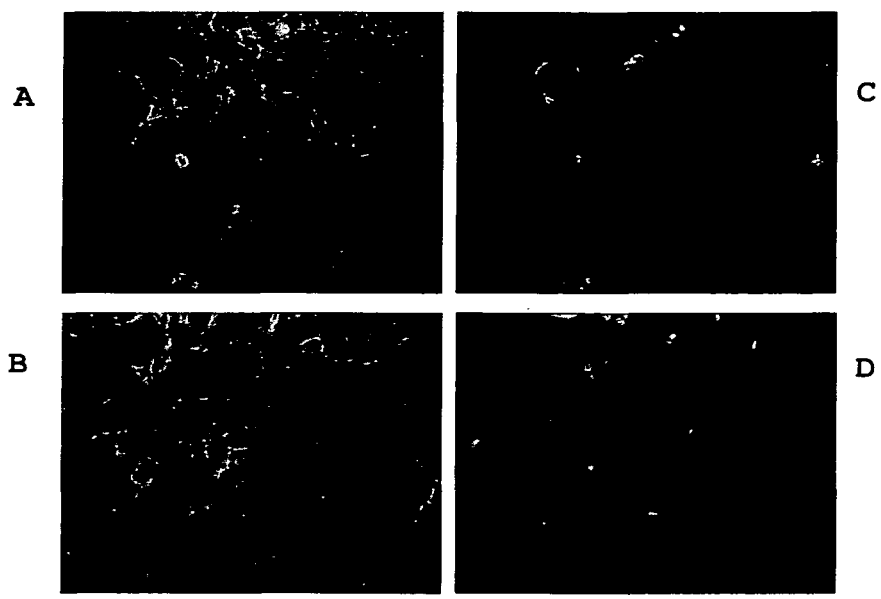
FIGS. 11A and 11B each provide photomicrographs showing the up-regulation of β-catenin in Caco2 cells following treatment with proenzyme reference formulation J.
Figure 11B:
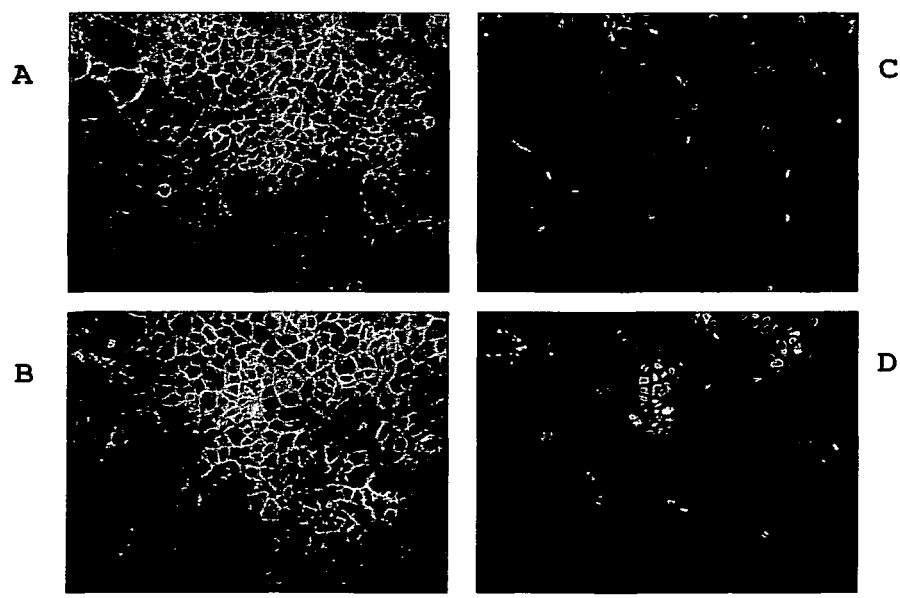
Figure 12:
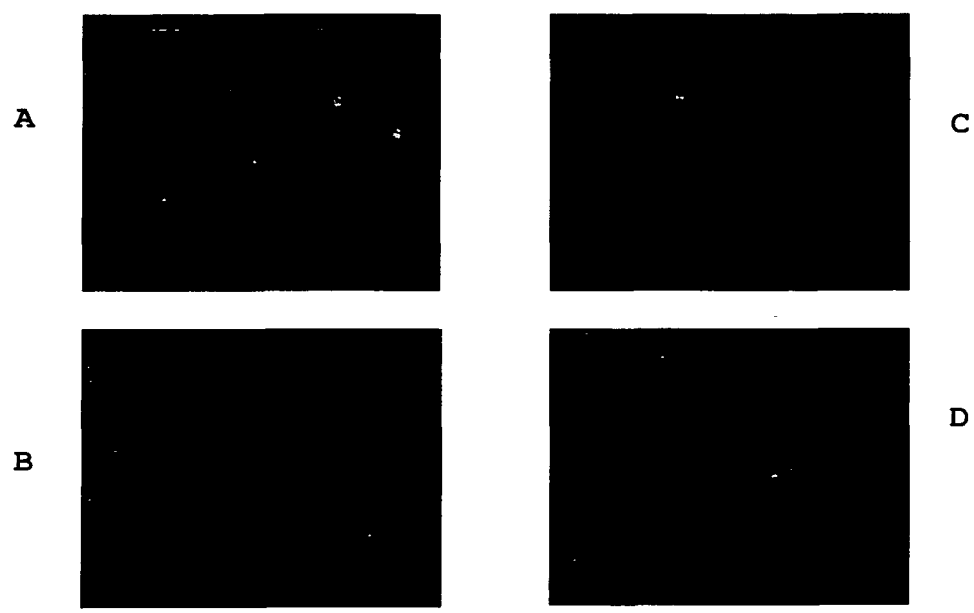
FIG. 12 provides photomicrographs showing the up-regulation of β-catenin and E-Cadherin in Panc1 cells following treatment with proenzyme reference formulation T.
Figure 13:
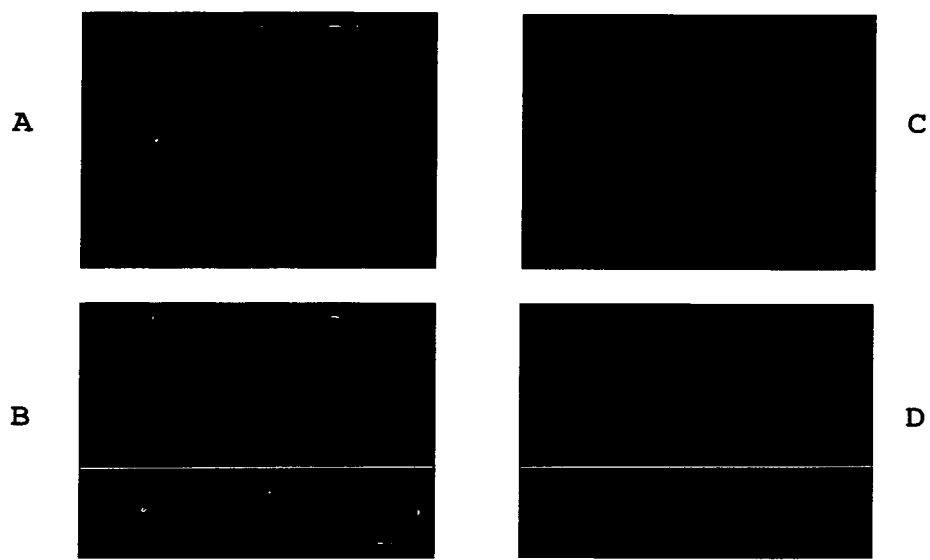
FIG. 13 provides photomicrographs showing the up-regulation of β-catenin and E-Cadherin in Caco2 cells following treatment with proenzyme reference formulation T.

The results observed by optical microscopy were corroborated by the SRB protein staining assay. Table 4 shows the mean value for 4 replicate wells of each concentration of the formulations used. The effect on cell death of the formulation B, J and T was dependent on the concentration; 2.5× and 5× killing all the cells in the wells as shown in FIG. 4. The value of $IC_{50}$ was obtained by plotting the absorbance against the concentration as is shown in FIG. 4. The control, shown as the OD for concentration 0, was the mean of 24 replicate wells.

TABLE 4

Effect of formulations B, J and T on Panc1 cells

| CONCENTRATION | B OD | J OD | T OD |
|---|---|---|---|
| 0 | 0.442 | 0.442 | 0.442 |
| 0.4 | 0.447 | 0.542 | 0.514 |
| 0.2 | 0.465 | 0.548 | 0.529 |
| 1 | 0.440 | 0.517 | 0.538 |
| 1.25 | 0.450 | 0.501 | 0.599 |
| 2.5 | 0.237 | 0.284 | 0.511 |
| 5 | 0.063 | 0.046 | 0.076 |

Effect of the Formulations on Colorectal Cancer Cells (Caco2)

Caco2 cells were seeded at a density of 20,000 cells/ml (day 1). The cells were treated with 0.25×; 0.5×; 1×; 1.25×; 2.5× and 5× of the different formulations, on day 2 and day 4. Cells were fixed at day 5. The formulation C at the concentrations tested did not have any effect on Caco2 cell viability, after the treatment on day 5 the cells showed a confluent and healthy monolayer (data not shown).

The SRB protein staining assay (Table 5) shows the mean value for 4 replicate wells of each concentration of the formulations used, the effect on cell death of the formulation B, J and T was dependent of the concentration: 2.5× and 5× killed all the cells in the wells as shown in FIG. 5. The lower concentration of these three formulations did not have effect on cell viability, as can be observed the optical densities (OD) recorded were not significant different from the control group. The control was the mean of 24 replicate wells, at the time of the fixation all the 24 wells of the control plate were completely confluent.

TABLE 5

Effect of formulations B, J and T on Caco2 cells

| CONC (1) | B (1) | J (1) | T (1) |
|---|---|---|---|
| 0 | 0.421 | 0.421 | 0.421 |
| 0.4 | 0.370 | 0.387 | 0.440 |
| 0.2 | 0.393 | 0.440 | 0.431 |
| 1 | 0.384 | 0.429 | 0.515 |
| 1.25 | 0.395 | 0.458 | 0.478 |
| 2.5 | 0.251 | 0.131 | 0.304 |
| 5 | 0.078 | 0.074 | 0.176 |

Treatments B, J and T have a toxic effect on all the cell types tested. The concentration of formulations B, J and T that display an effect on cell viability were 2.5× and 5×. After treatment cells display a rounded morphology, cell shrinkage and increased detachment.

Determination of $IC_{50}$ of Formulations

The $IC_{50}$ value for each formulation was obtained by plotting the absorbance against the concentration. The $IC_{50}$ of the different formulations was obtained for the cell lines: Caco2, Panc1 and OE33 when administered twice in a week. The final $IC_{50}$ values (with corresponding actual mg/ml concentrations) were used in the subsequent cell assays.

TABLE 6A $IC_{50}$ of formulations on Panc1

|  | B (2.4x) | J (2.5x) | T (2.5x) |
|---|---|---|---|
| Trypsinogen (mg/ml) | 0.031 | 0.0032 | 0.0032 |
| Chymotrypsinogen (mg/ml) | 0.031 | 0.0032 | 0.0032 |
| Elastase (mg/ml) | 0.0048 | 0.0075 | — |

TABLE 6B $IC_{50}$ of formulations on OE33 cells

|  | B (2.4x) | J (2.5x) | T (2.5x) |
|---|---|---|---|
| Trypsinogen (mg/ml) | 0.031 | 0.0032 | 0.0032 |
| Chymotrypsinogen (mg/ml) | 0.031 | 0.0032 | 0.0032 |
| Elastase (mg/ml) | 0.0048 | 0.0075 | — |

TABLE 6C $IC_{50}$ of formulations on Caco2 cells

|  | B (2.5x) | J (2.4x) | T (2.5x) |
|---|---|---|---|
| Trypsinogen (mg/ml) | 0.032 | 0.0031 | 0.0032 |
| Chymotrypsinogen (mg/ml) | 0.032 | 0.0031 | 0.0032 |
| Elastase (mg/ml) | 0.005 | 0.0072 | — |

Expression of Cell-Cell Adhesion Markers

Changes in expression of cell-cell adhesion markers β-catenin and E-cadherin were investigated in Panc1, OE33 and Caco2 cells following treatment with the $IC_{50}$ concentration of formulations J and T.

Cells were treated with the $IC_{50}$ concentration of the formulations. Cells were harvested, washed three times with phosphate buffered saline PBS and fixed with 4% paraformaldehyde in PBS for 30 minutes. Cells were washed three times with PBS and post fixed with ice cold acetone/methanol (1:1) for 5 minutes at −20° C. The cell were washed three times in PBS and blocked in 2% blocking buffer solution for 1 hour at room temperature. Cells were then incubated overnight in primary antibody diluted in blocking buffer solution at 4° C. Cells were washed three times in PBS and then incubated for 2 hours with secondary antibodies in blocking buffer solution. Cells were washed three times in PBS and incubated 15 minutes in 1:1000 DAPI/PBS (to demonstrate nuclear staining) at room temperature. Coverslips were mounted on slides with mounting media. Controls were performed with non-treated cells. The indirect immunofluorescence staining was performed using monoclonal antibodies raised to E-cadherin (Transduction Labs BD Biosciences Clone 36) and β-catenin (Transduction Labs BD Biosciences Clone 14). The secondary antibody used is horse anti-mouse fluorescein (Vector Labs F12000).

The increment of β-catenin and E-cadherin expression after treatment with the formulations tested was quantified by measuring the fluorescence intensity of the samples under the fluorescence microscopy, different fields of a same sample were measured and the mean of the intensity collections is shown in Table 7.

TABLE 7

Mean of fluorescence intensity of cells treated with formulations J and T

|  | Panc1 | | Caco2 | | OE33 | |
|---|---|---|---|---|---|---|
|  | J | T | J | T | J | T |
| E-cadherin | 21.99 | 33.59 | 78.03 | 73.13 | 47.27 | — |
| Control | 12.92 | 10.02 | 10.59 | 12.43 | 6.06 | — |
| β-catenin | 32.92 | 42.92 | 64.20 | 67.05 | 34.62 | — |
| Control | 10.58 | 9.32 | 11.92 | 5.92 | 16.22 | — |

Summary

Panc1, Caco2 and OE33 cells when treated with $IC_{50}$ concentration of formulations J and T showed an increase in the intensity of the immunofluorescence when compared with non treated cells. This correlates to an increase in β-catenin and E-cadherin expression on cancer cells compared with control cells, as shown in FIGS. 6 to 13. β-catenin and E-cadherin are shown in green and nuclei are shown in blue.

Example 1

Enhanced Proenzyme Formulations

A study was undertaken to determine the effect of the proenzyme formulation comprising trypsinogen (pT), chymotrypsinogen (pC) and α-amylase (A) (formulation referred to as JBp1) on the growth of 24 cancer cell lines. Based on the IC50 and maximal inhibition values generated in this initial study, three cell lines were to be selected for further understanding the effects of the three individual components in JBp1 on cancer cell growth. The study applied the isobolographic method to understand the interaction between the three components of JBp1: α-amylase, trypsinogen and chymotrypsinogen. Based on the results obtained, an enhanced formulation (JBp1vP) was proposed and tested in isobolographic studies with a second formulation comprising 2-deoxy-D-glucose (D), capsiate (C) and methylselenocysteine (M).

Summary

The cell growth inhibitory properties of the proenzyme formulation JBp1 was studied in a panel of 24 human cancer cell lines. IC50 values for the majority of the cell lines in this panel were obtained. Based on the IC50 values and maximum growth inhibition, three cell lines, A-549, HCT-15 and MIAPaCa-2 were selected for further combination studies using the isobolographic method. The use of isobolograms allowed the study of the level of interaction between the three individual components of JBp1: α-amylase, trypsinogen and chymotrypsinogen. By studying the growth inhibition activity of the individual components in combination with each other and mixtures of two components, an enhanced composition of the JBp1 formulation was identified and has been referred to as "JBp1vP". This enhanced formulation was tested in combination assays against a second formulation comprising 2-deoxy-D-glucose (D), capsiate (C) and methylselenocysteine (M), wherein the second formulation being referred to as DCM and the combination of the first and second formulation being referred to as JBp1vP-DCM. The isobolographic analysis of the interaction between JBp1vP and DCM showed the potential to act synergistically, especially at low concentrations of DCM (see results for MIAPaCa-2 cell line in FIG. 14 and Table 8).

TABLE 8

Summary of the Isobolographic analysis for Chymotrypsinogen, Trypsinogen, α-amylase and dual combinations in A-549, HCT-15 and MIAPaCa-2 cells

| | T | C | A | TC | TA | CA | JBp1vP | DCM |
|---|---|---|---|---|---|---|---|---|
| A-549 ||||||||||
| T | | WR | NR | | | — | | |
| C | WR | | N | | NR | | | |
| A | NR | N | | N | | | | |
| TC | | | | | N | | | |
| TA | | NR | | | | | | |
| CA | — | | | | | | | |
| JBp1vP | | | | | | | | N |
| DCM | | | | | | | N | |
| HCT-15 ||||||||||
| T | | N | N | | | NR | | |
| C | N | | N | | N | | | |
| A | N | N | | N | | | | |
| TC | | | | | N | | | |
| TA | | N | | | | | | |
| CA | NR | | | | | | | |
| JBp1vP | | | | | | | | N |
| DCM | | | | | | | N | |
| MIAPaCa-2 ||||||||||
| T | | WR | WR | | | WR | | |
| C | WR | | WR | | NR | | | |
| A | WR | WR | | NR | | | | |
| TC | | | NR | | | | | |
| TA | | NR | | | | | | |
| CA | WR | | | | | | | |
| JBp1vP | | | | | | | | NR |
| DCM | | | | | | | NR | |

Legend:
T: Trypsinogen
C: Chymotrypsinogen
A: α-amylase
TC: Chymotrypsinogen:Trypsinogen (6:1)
CA: Chymotrypsinogen:α-amylase (1:0.25)
TA: Trypsinogen:α-amylase (1:0.25)
WR: Wide-range synergistic interaction (more than 7 g values below 1.0)
NR: Narrow-range synergistic interaction (3 to 7 g values below 1.0)
N: Non-synergistic interaction (less than 3 g values below 1.0)

Isobolographic Method

The dose-response relations of agents can be used to construct a model giving the expected effect of a combination. The combination of drugs A and B shall be termed (da,db) where da and db are doses of A and B. Effect is treated as a mathematical function, $E(d_a, d_b)$. E is sometimes expressed as a fractional effect, then the survival fraction is S: S=1−E. Finally, Da and Db are doses of drugs A and B given separately, which produce an isoeffective response with the combination. Isoboles (iso-effect curves) can be constructed based on the assumption that there is no interaction between the drugs used in combination. The combination $(d_a, d_b)$ is represented by a point on a graph that has axes representing doses of the individual drugs. It is expected that if the drugs do not interact, this point shall fall on a straight line (isobole) connecting the two axes between the values representing doses ($D_a$ and $D_b$) isoeffective with the combination (da, db). The equation for the zero interaction isobole for two compounds is $$\frac{d_a}{D_a} + \frac{d_b}{D_b} = 1 \qquad (1)$$

Where the number of compounds in combination is n, the equation is $$\sum_{i=1}^{n} \frac{d_i}{D_i} = 1 \; (i = 1, 2 \ldots, n) \qquad (2)$$

When the drugs in the combination are isoeffective with the individual doses, the isobole is a straight line. However, if the effect of the combination is larger than expected from the individual dose-response curves, then smaller amounts of $d_a$ and/or $d_b$ are needed to produce an equipotent effect to $D_a$ and $D_b$ (both unchanged), thus $$\frac{d_a}{D_a} + \frac{d_b}{D_b} < 1 \qquad (3)$$

This ratio is also called g value and it used to determine the type of interaction. In this case the calculated isobole is concave. Antagonism would produce effects to the opposite direction; therefore the isobole representing this type of interaction would be convex.

In summary, g values can be:

$$\frac{d_a}{D_a} + \frac{d_b}{D_b} \quad \begin{array}{ll} < 1 & \text{superadditive (synergistic)} \\ = 1 & \text{additive (zero interaction)} \\ > 1 & \text{subadditive (antagonistic)} \end{array}$$

The interaction between the three components of the novel formulation JBp1 (α-amylase, trypsinogen and chymotrypsinogen) was studied. Furthermore, the isobolographic method was employed to determine an enhanced ratio of the three components in the formulation. The enhanced JBp1 formulation was then studied in combination with a second formulation DCM.

Materials and Methods

Sterile flat-bottom 96-well cell culture plates were obtained from Becton-Dickinson (North Ryde, NSW, Australia); RPMI 1640 and DMEM cell culture medium, FBS, GlutaMax, Penicillin-streptomycin, sodium pyruvate, HEPES, HAM's, FCS and DPBS were obtained from Invitrogen Australia (Mt Waverley, VIC, Australia); Trypan Blue was obtained from Sigma-Aldrich (Castle Hill, NSW, Australia); CellTiter-Blue® Cell Viability Assay was obtained from Promega (Madison, Wis., USA); SpectraMax Gemini XPS Fluorometer was obtained from Molecular Devices (Sunnyvale, Calif., USA).

All the cell lines used in these studies were of human origin and were sourced from the American Type Culture Collection (ATCC) (Rockville, Md., USA).

The following Table 9 shows the growth conditions and initial cell seeding densities in cells per well used in all IC50 determination and combination assays. The cells were cultured at 37° C. in a humidified cell culture incubator supplied with 95% air/5% $CO_2$.

TABLE 9

Growth conditions and seeding densities for IC50 study and combination assays

| Cell line | Tumour Type | Cell culture medium | Seeding density |
|---|---|---|---|
| COLO-205 | Carcinoma, colorectal | RPMI + 10% FCS + 1% GlutaMax + 1% Pen/Strep | 2000 |
| COLO-201 | Carcinoma, colorectal | RPMI + 10% FCS + 1% GlutaMax + 1% Pen/Strep | 2500 |
| HCT-116 | Carcinoma, colorectal | RPMI + 10% FCS + 1% GlutaMax + 1% Pen/Strep | 2000 |
| HCT-15 | Carcinoma, colorectal | RPMI + 10% FCS + 1% GlutaMax + 1% Pen/Strep | 2000 |
| HT-29 | Adenocarcinoma, colorectal | RPMI + 10% FCS + 1% GlutaMax + 1% Pen/Strep | 4000 |
| BxPC-3 | Adenocarcinoma | RPMI + 10% FCS + 1% GlutaMax + 1% Pen/Strep | 4000 |
| MIAPaCa-2 | Carcinoma | DMEM + 10% FCS + 1% GlutaMax + 1% Pen/Strep + 1% HEPES + 1% NaPy | 4000 |
| PANC-1 | Epithelioid carcinoma | DMEM + 10% FCS + 1% GlutaMax + 1% Pen/Strep | 3000 |
| A2780 | Ovary, adenocarcinoma | RPMI + 10% FCS + 1% GlutaMax + 1% Pen/Strep | 4000 |
| OVCAR-3 | Ovary, adenocarcinoma | RPMI + 10% FCS + 1% GlutaMax + 1% Pen/Strep | 3000 |
| SK-OV-3 | Adenocarcinoma, ovary, Malignant Ascites | RPMI + 10% FCS + 1% GlutaMax + 1% Pen/Strep | 4000 |
| BT-474 | Breast carcinoma | RPMI + 10% FCS + 1% GlutaMax + 1% Pen/Strep | 5000 |
| MDA-MB-231 | Breast adenocarcinoma | DMEM + 10% FCS + 1% GlutaMax + 1% Pen/Strep | 5000 |
| MDA-MB-453 | Breast carcinoma | RPMI + 10% FCS + 1% GlutaMax + 1% Pen/Strep | 5000 |
| MDA-MB-468 | Breast adenocarcinoma | RPMI + 10% FCS + 1% GlutaMax + 1% Pen/Strep | 4000 |
| A549 | NSCLC | RPMI + 10% FCS + 1% GlutaMax + 1% Pen/Strep | 3000 |
| HOP-92 | NSCLC, pleural effusion | RPMI + 10% FCS + 1% GlutaMax + 1% Pen/Strep | 4000 |
| NCI-H460 | NSCLC, pleural effusion | RPMI + 10% FCS + 1% GlutaMax + 1% Pen/Strep | 3000 |
| NCI-H520 | NSCLC, squamous cell carcinoma | RPMI + 10% FCS + 1% GlutaMax + 1% Pen/Strep | 4000 |
| NCI-H596 | NSCLC, adenosquamous carcinoma | RPMI + 10% FCS + 1% GlutaMax + 1% Pen/Strep | 3000 |
| NCI-H82 | NSCLC | RPMI + 10% FCS + 1% GlutaMax + 1% Pen/Strep | 5000 |
| OE-21 | Oesophagaeal squamous | RPMI + 10% FCS + 1% GlutaMax + 1% Pen/Strep | 5000 |
| OE-33 | Oesophagaeal carcinoma | RPMI + 10% FCS + 1% GlutaMax + 1% Pen/Strep | 5000 |
| KYSE-30 | Squamous cell carcinoma | RPMI + HAM's F12 (1:1) + 2% FCS + % GlutaMax + 1% Pen/Strep | 4000 |

Test Articles and Formulation

Test Article 1 was trypsinogen, which was supplied by Applichem (Darmstadt, Germany). Test Article 2 was chymotrypsinogen, which was supplied by BBI Enzymes (Gwent, UK). Test Article 3 was α-amylase, which was supplied by Annecis Ltd (Lancaster, UK). Test Article 4 was 2-deoxyglucose, which was supplied by Sigma-Aldrich (Castle Hill, NSW, Australia). Test Article 5 was capsiate, which was supplied by Propanc Pty Ltd. Test Article 6 was methylselenocysteine, which was supplied by Sigma-Aldrich (Castle Hill, NSW, Australia)

α-Amylase, trypsinogen and chymotrypsinogen were dissolved in phosphate buffered saline (PBS) and used immediately or stored at 4° C. for further use. The Test Article DCM is composed of 2-deoxyglucose, capsiate and methylselenocysteine in a ratio of 1:1:0.0001. These three components were mixed together at these ratios, resuspended in PBS and used immediately after preparation.

Cell Growth Assays

For 1050 analyses, Test Articles were added to cells 24 hours post-seeding. Test Article concentrations were tested in triplicates for each cell line. The CellTiter-Blue® Assay was carried out on all plates 72 hours post addition of Test Articles.

For combination assays, two 96 well plates were seeded for each cell line and Test Article combination, to allow for replication of each experiment. Test Articles were added to cells 24 hours post-seeding according to the following pipetting scheme (cells within the range A3:G11 contain the combination of both drugs at the concentrations given in column 2 and row H.

The initial concentrations for each compound in each cell line were decided based on the calculated IC50 in a way that the IC50 for each drug fell within the concentration in the dilution series. The CellTiter-Blue® Assay was carried out on all plates 72 hours post-addition of Test Articles.

Following incubation of cells in Test Article-containing media, 10 µL of CellTiter-Blue® was added to each well and incubated with cells for up to 4 hours. Fluorescence was measured using a Spectramax Gemini XPS Fluorometer. All data were recorded and entered into Microsoft® Excel spreadsheets for interpretation.

Data collected from CellTiter-Blue® assays were plotted as dose response curves for IC50 determination, and as isobolograms to assess the type of interaction between Test Article combinations. For IC50 determinations, growth inhibition was calculated and plotted against compound concentration. In these plots, the X-axis (compound concentration) was represented in a logarithmic scale. IC50 concentration was calculated as the half maximal (50%) inhibitory concentration (IC) for each compound using GraphPad Prism version 5.0 for Mac OSX (GraphPad Software, San Diego Calif., USA).

For combination studies, isobolographic analysis was performed using vivoPharm's proprietary analysis template. The isobolographic analysis provides a measure of the type of interaction (i.e synergistic, additive or antagonistic) occurring between two compounds. One parameter that defines the type of interaction is the g value. As described above, g values of over 1.0 indicate an antagonistic interaction and g values below 1.0 indicate a synergistic interaction. Each isobolographic assay results in 9 g values, one for each concentration of the second compound in the combination (compound B in the analysis template). For this study, the interactions between two compounds were categorized in three groups: wide-range synergistic interactions which showed more than 7 g values below 1.0, narrow-range synergistic interactions which resulted in 3 to 7 g values below 1.0 and non-synergistic interactions which yielded less than 3 g values below 1.0. Table 5 shows the summary of all the interactions analyzed in this study.

All procedures used in the performance of this study were carried out in accordance with standard operating procedures.

Results

IC50 determination assays were performed for JBp1 in 24 cancer cell lines. As seen in Table 10, IC50 values were obtained for 15 of the cell lines (A2780, HOP-92, BxPc-3, HT-29, KYSE-30, MIAPaCa-2, OE-33, A549, HCT-15, OE-21, NCI-H82, HCT-116, MDA-MB468, NCI-H460 and BT474). The remaining cell lines showed maximum inhibition values or dose-response curves that did not allow for the determination of IC50 values within the range of concentrations of JBp1 tested in this study. Table 10 shows the 1050 and maximum growth inhibition values for all 24 cell lines in decreasing order of maximum growth inhibition.

Based on the 1050 and maximum inhibition values obtained for the 24 cell lines and the suitability of each cell line for follow up animal studies, three cell lines were selected for isobolographic studies. These cell lines, A-549, HCT-15 and MIAPaCa-2, are highlighted in bold characters in Table 10.

TABLE 10

Summary of IC50 values for JBp1 in 24 cell lines

| Cell Line | IC50 JBp1(mg/mL) | Maximum Inhibition % |
|---|---|---|
| A2780 | 0.09 | 93.4 |
| HOP-92 | 0.13 | 91.1 |
| BxPc-3 | 0.16 | 90.7 |
| HT-29 | 0.04 | 87.6 |
| KYSE-30 | 0.03 | 86.2 |
| MIAPaCa-2 | 0.08 | 85.0 |
| OE-33 | 0.15 | 84.1 |

TABLE 10-continued

Summary of IC50 values for JBp1 in 24 cell lines

| Cell Line | IC50 JBp1(mg/mL) | Maximum Inhibition % |
|---|---|---|
| A549 | 0.15 | 83.9 |
| HCT-15 | 0.08 | 82.3 |
| OE-21 | 0.42 | 68.2 |
| NCI-H82 | 0.06 | 66.9 |
| HCT-116 | 0.14 | 62.4 |
| MDA-MB468 | 0.10 | 62.3 |
| COLO-205 | — | 61.7 |
| NCI-H460 | 0.07 | 58.9 |
| BT474 | 0.01 | 55.3 |
| SK-OV-3 | — | 54.5 |
| PANC-1 | — | 52.8 |
| NCI-596 | — | 51.4 |
| MDA-MB-231 | — | 47.5 |
| COLO-201 | — | 36.3 |
| NCI-H520 | — | 34.0 |
| MDA-MB-453 | — | 16.2 |
| OVCAR-3 | — | 9.3 |

The isobolographic method for studying the interaction between compounds requires the determination of the IC50 values for those components prior to running the combination assays. Therefore, IC50 determination assays were performed for the three individual components of JBp1, namely trypsinogen, chymotrypsinogen and α-amylase, in the three selected cell lines A-549, HCT-15 and MIAPaCa-2. As seen in Table 11, trypsinogen showed IC50 values ranging from 0.23 to 0.41 mg/mL in all three cell lines. α-amylase and chymotrypsinogen did not present IC50 values within the range of concentrations tested.

TABLE 11

Summary of IC50 values and maximum growth inhibition for trypsinogen, chymotrypsinogen and α-amylase in A-549, HCT-15 and MIAPaCa-2 cells.

| | A-549 | HCT-15 | MIAPaCa-2 |
|---|---|---|---|
| | IC50 values (mg/mL) | | |
| Trysinogen | 0.23 | 0.41 | 0.28 |
| Chymotrypsinogen | — | — | — |
| α-amylase | — | — | — |
| | Maximum Inhibition (%) | | |
| Trysinogen | 75.7 | 77.2 | 82.3 |
| Chymotrypsinogen | 26.5 | 16.6 | 28.9 |
| α-amylase | 2.6 | 16.0 | 13.8 |

The isobolographic analysis provides a measure of the type of interaction (i.e synergistic, additive or antagonistic) occurring between two compounds. One parameter that defines the type of interaction is the g value. As described above, g values of over 1.0 indicate an antagonistic interaction and g values below 1.0 indicate a synergistic interaction. Each isobolographic assay results in 9 g values, one for each concentration of the second compound in the combination (compound B in the analysis template). For this study, the interactions between two compounds were categorized in three groups: wide-range synergistic interactions which showed more than 7 g values below 1.0, narrow-range synergistic interactions which resulted in 3 to 7 g values below 1.0 and non-synergistic interactions which yielded less than 3 g values below 1.0. Table 8 shows the summary of all the interactions analyzed in this study.

Figure 15:
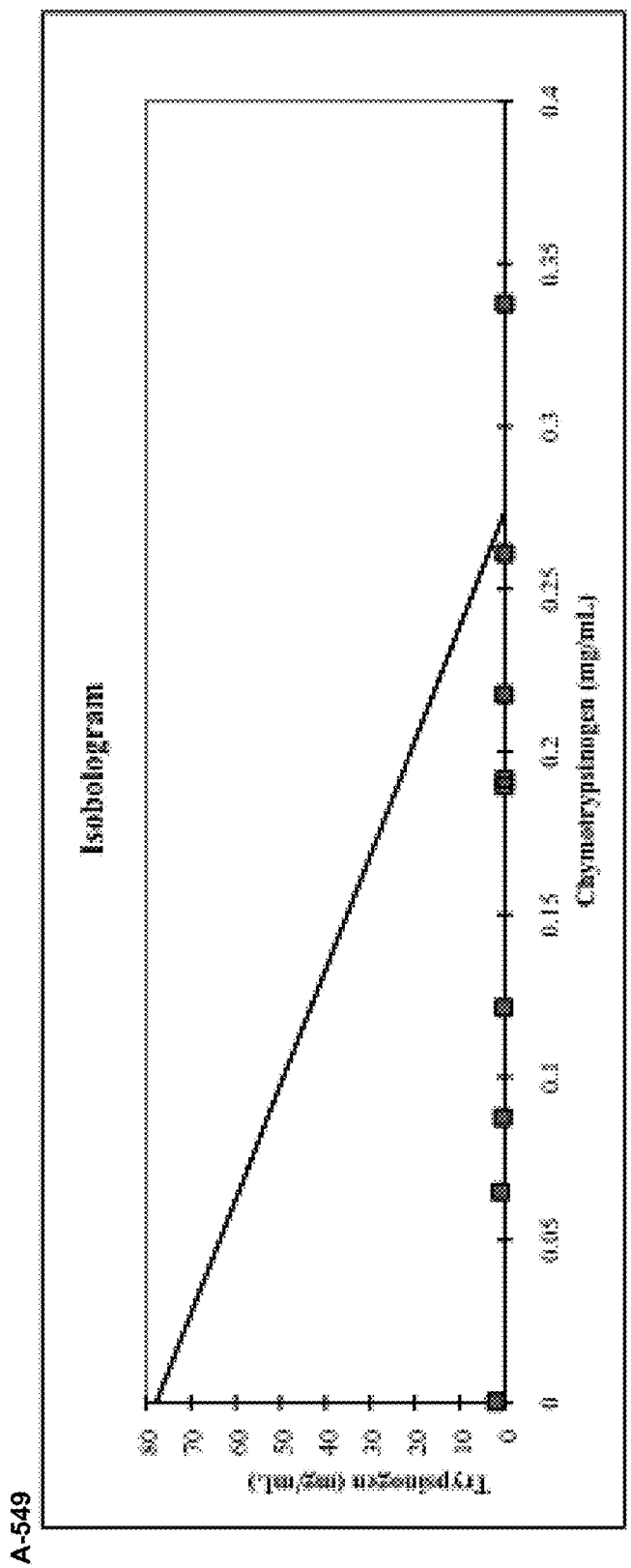
FIG. 15 provides an isobolographic analysis for trypsinogen and chymotrypsinogen in A-549, HCT-15 and MIAPaCa-2 cells.
Figure 15:
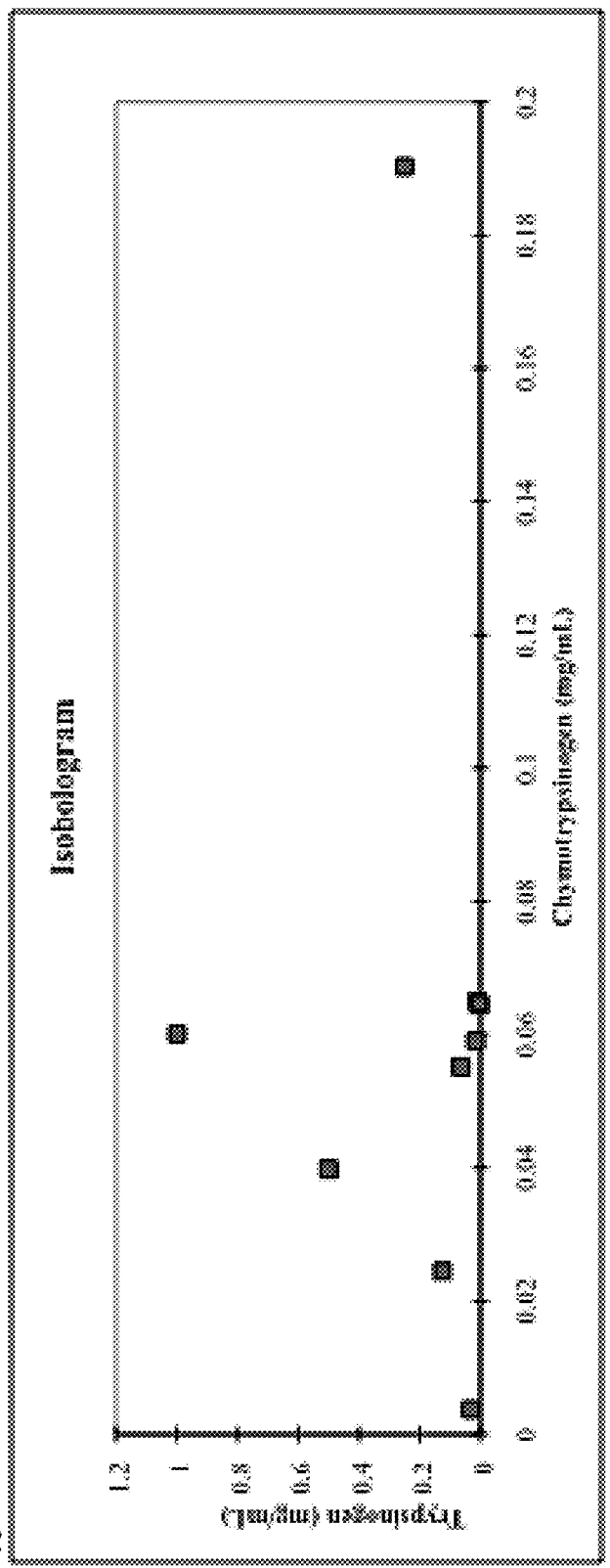
Figure 15:
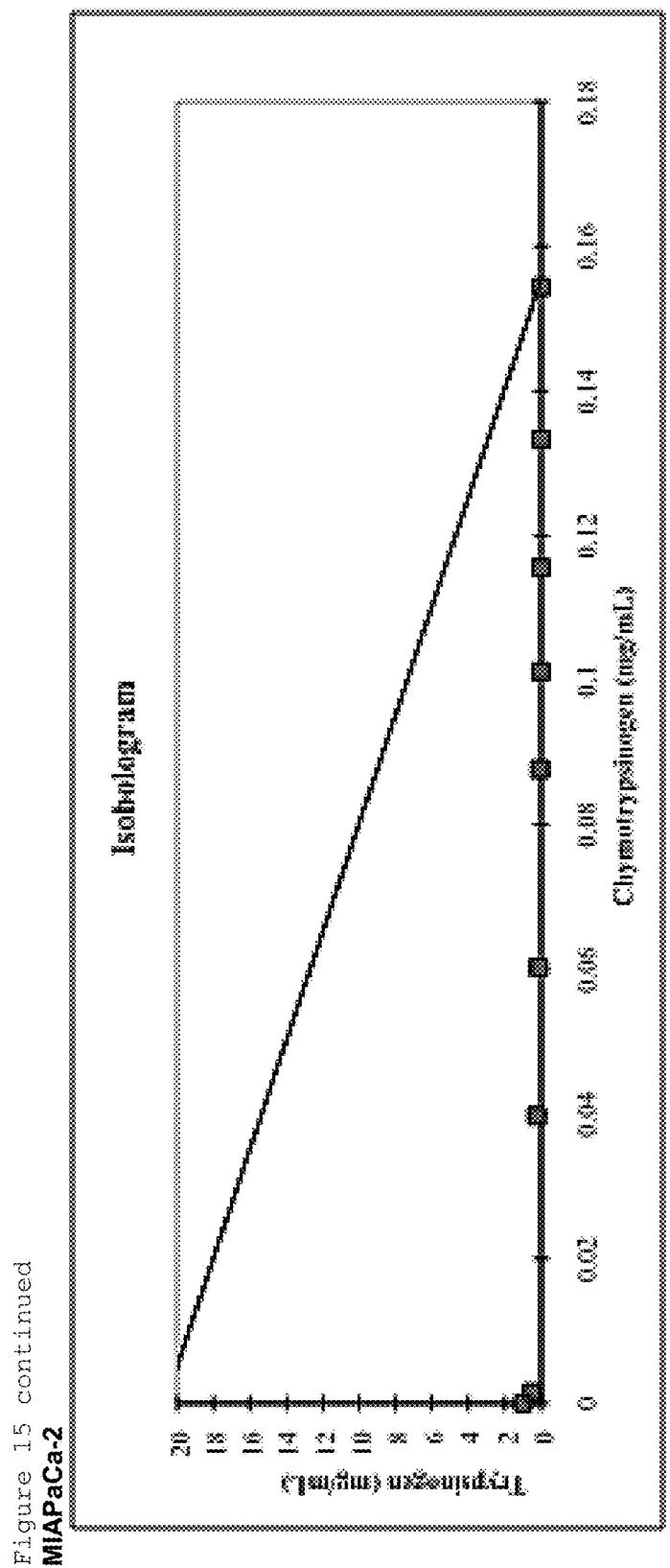
Figure 16:
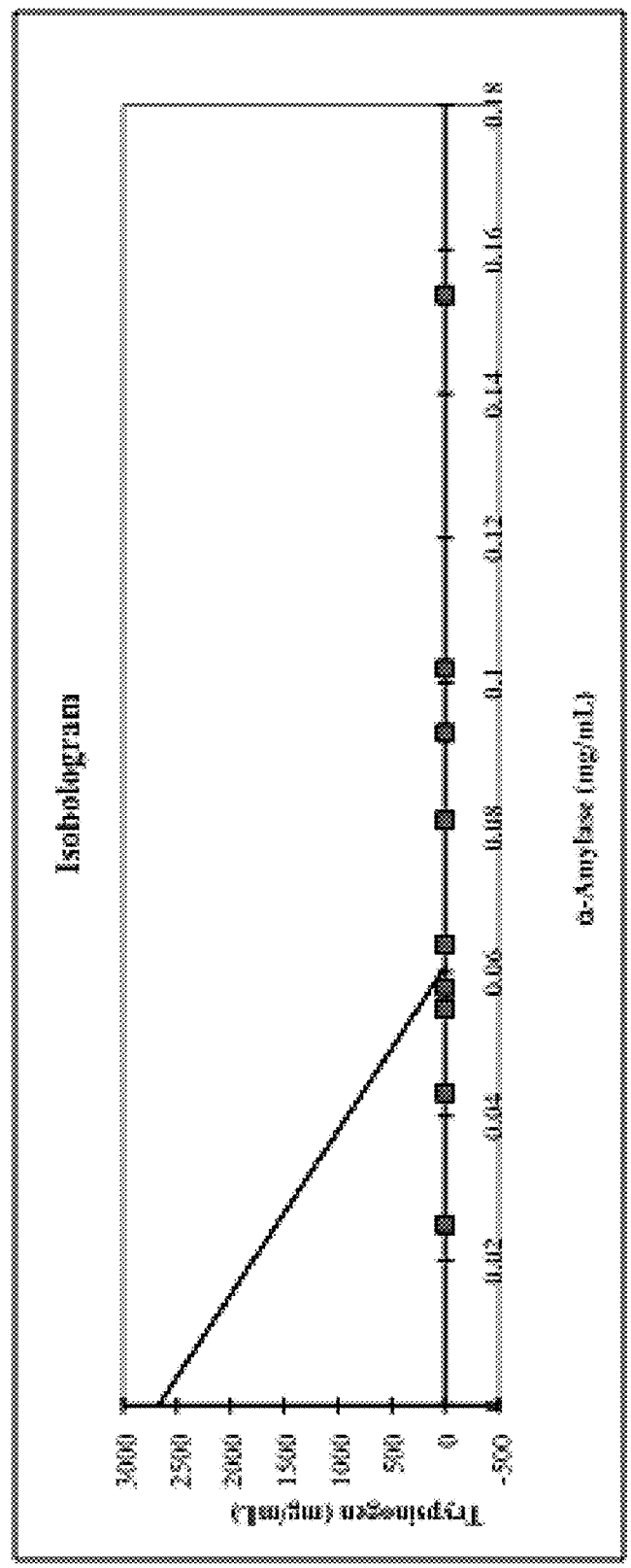
FIG. 16 provides an isobolographic analysis for trypsinogen and α-amylase in A-549, HCT-15 and MIAPaCa-2 cells.
Figure 16:
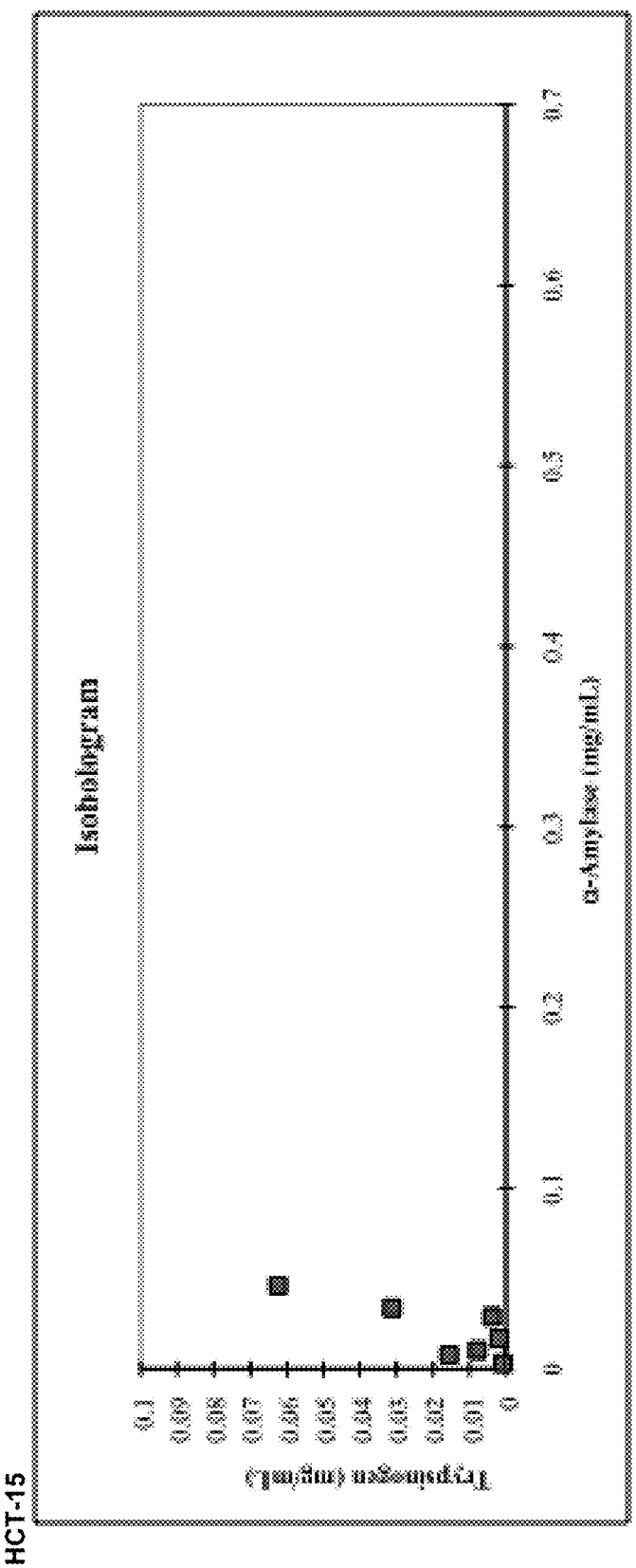
Figure 16:
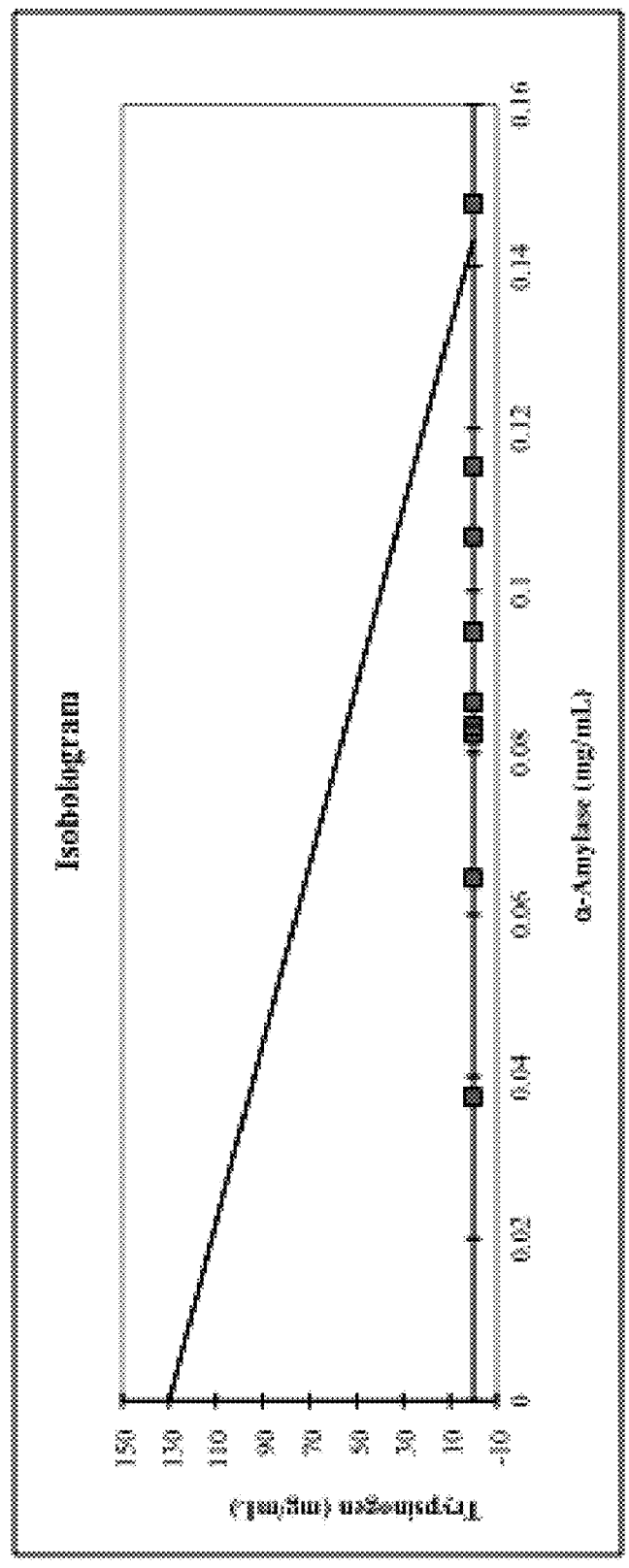
Figure 17:
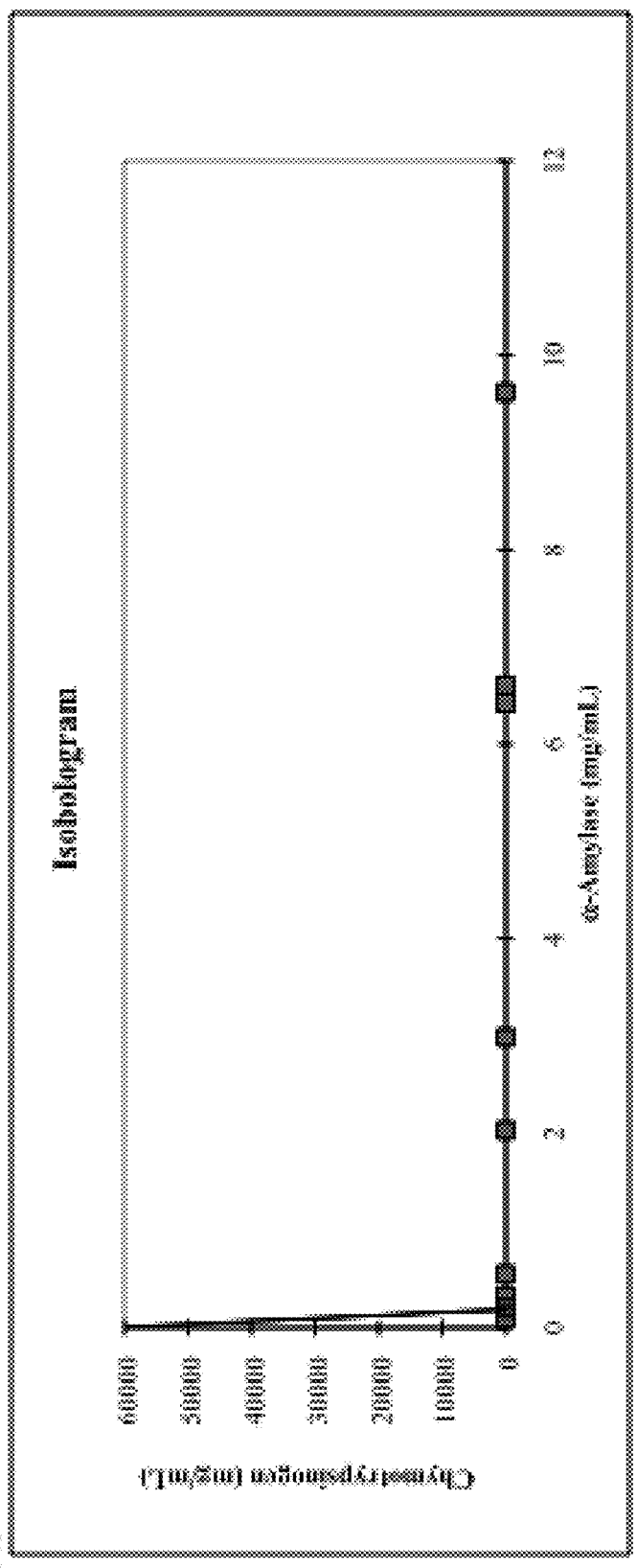
FIG. 17 provides an isobolographic analysis for chymotrypsinogen and α-amylase in A-549, HCT-15 and MIAPaCa-2 cells.
Figure 17:
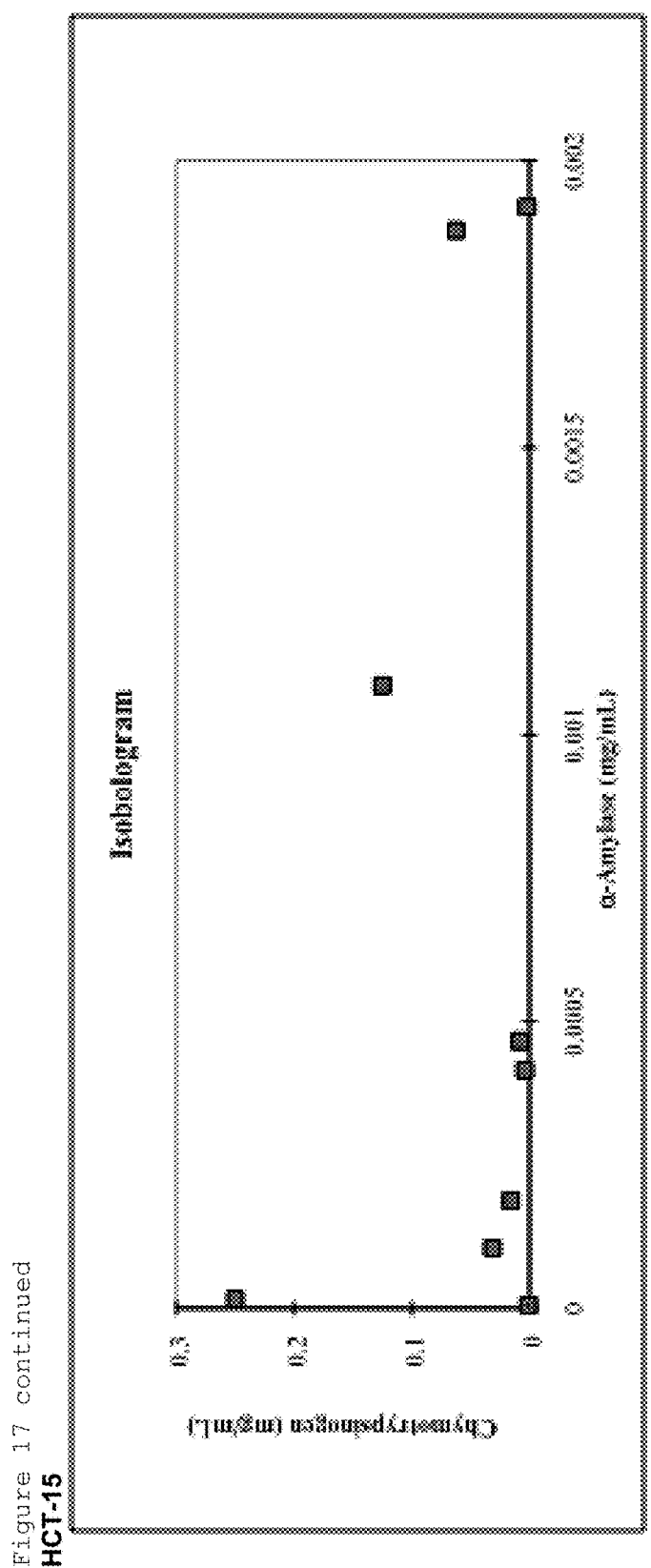
Figure 17:
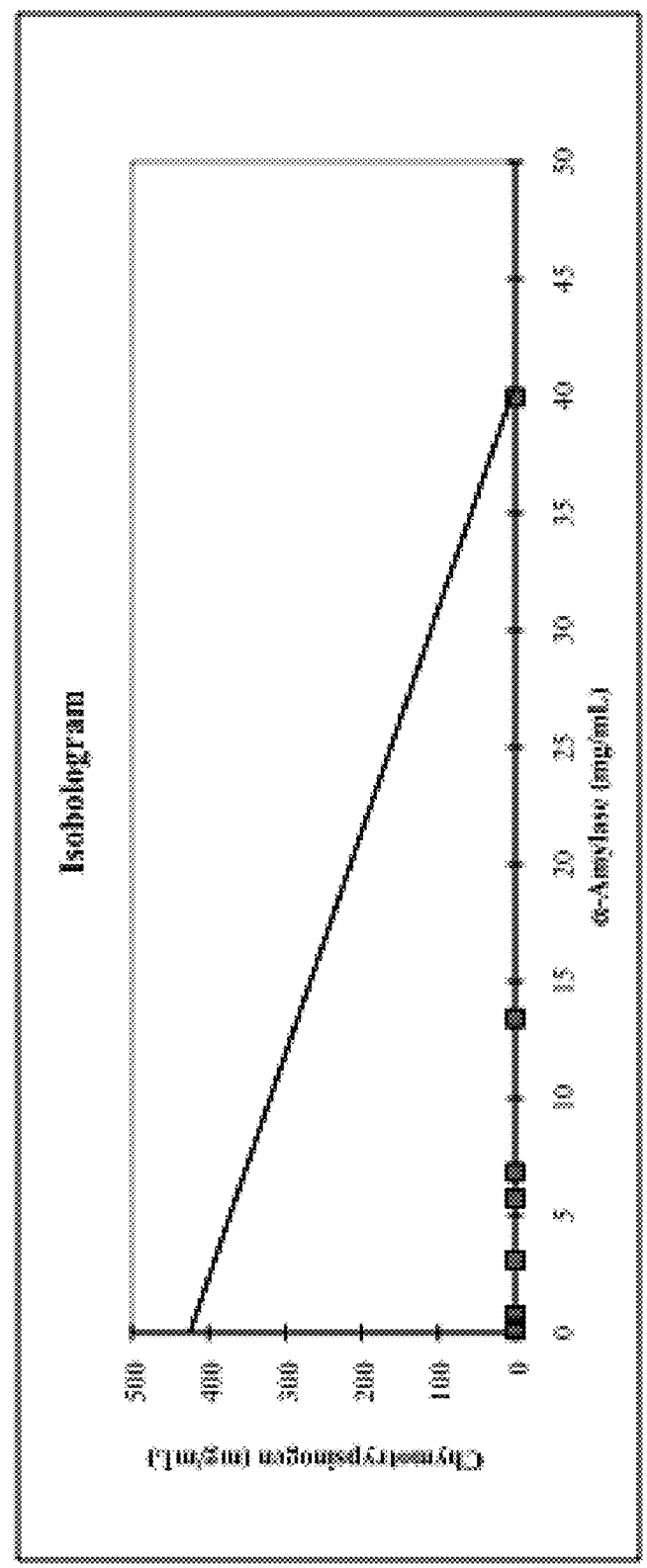

Despite the fact that no IC50 values were obtained for α-amylase, and chymotrypsinogen, the interaction between each other and with trypsinogen was studied in combination assays, since it is understood that these components still interact when in combination with a second compound. FIGS. 15-17 show the isobolograms resulting from the combination assays between α-amylase, trypsinogen and chymotrypsinogen in A-549, HCT-15 and MIAPaCa-2 cells.

As seen in FIG. 15 and Table 8, trypsinogen and chymotrypsinogen showed isobolographic results consistent with a wide-range of synergistic interaction in A-549 and MIAPaCa-2 cells. In HCT-15 cells, the isobolographic profile was consistent with a non-antagonistic interaction (the isobolographic line is located almost superimposed on the X-axis and might not be clearly distinguishable in the figure). Based on the overall results of the combination assays in the three selected cell lines, it was defined that the enhanced ratio of trypsinogen and chymotrypsinogen in the formulation should be set to 6:1 (chymotrypsinogen:trypsinogen). This ratio is supported by: 1) higher concentrations of chymotrypsinogen significantly improved the growth inhibitory effect, as reflected by very low g values at 1 and 2 mg/mL of chymotrypsinogen in A-549 and MIAPaCa-2 cells; and 2) concentrations of trypsinogen above 0.25 mg/mL did not add additional inhibitory effects. Therefore, the average of the top two concentrations of chymotrypsinogen (1.5 mg/mL) was divided by the top concentration of trypsinogen (0.25 mg/mL) to obtain a ratio of 1.5 to 0.25 or 6:1.

FIG. 16 shows the isobolograms for the interaction between trypsinogen and α-amylase in A-549, HCT-15 and MIAPaCa-2 cells. The combination of these two compounds resulted in synergistic interactions in A-549 and MIAPaCa-2 cells and a non-synergistic interaction in HCT-15 cells (Table 8). The positive interaction was of the wide-range type in MIAPaCa-2 cells and of the narrow-range type in A-549 cells. Given the range of responses observed for this interaction in the three tested cell lines, these data were not used to determine the ratio between these two components in the JBp1 formulation.

FIG. 17 shows the isobolograms for the interaction between chymotrypsinogen and α-amylase in A-549, HCT-15 and MIAPaCa-2 cells. The combination of these two compounds resulted in a synergistic interaction in MIAPaCa-2 cells and non-synergistic interactions in A-549 and HCT-15 cells. Given the negative effect of α-amylase on the cell growth inhibitory effects of chymotrypsinogen, it was decided to leave the ratio of this component to the other two components of JBp1 at the original concentration (1:0.25, chymotrypsinogen:α-amylase).

In summary, after the first round of combination assays, it was determined that the ratio chymotrypsinogen:trypsinogen would be set at 6:1 and the ratios of chymotrypsinogen:α-amylase and trypsinogen:α-amylase would be used at the original concentrations of 1:0.25.

For the second round of combination studies, the pair of compounds and the ratio defined above were re-defined as the new test compounds as follows:

Chymotrypsinogen:Trypsinogen (6:1)=TC
Chymotrypsinogen:α-Amylase (1:0.25)=CA
Trypsinogen:α-Amylase (1:0.25)=TA IC50 determination assays were performed for these re-defined compounds in A-549, HCT-15 and MIAPaCa-2 cells. Table 12 presents the dose-response curves and the calculated IC50 values and maximum growth inhibition for the three compounds in the three selected cell lines. IC50 values were obtained for TC and TA in all three cell lines. However, IC50 values could not be found for CA within the range of concentrations tested.

TABLE 12

Summary of IC50 values and maximum growth inhibition for TC, TA and CA in A-549, HCT-15 and MIAPaCa-2 cells.

|  | A-549 | HCT-15 | MIAPaCa-2 |
|---|---|---|---|
| | IC50 values (mg/mL) | | |
| TC | 0.61 | 0.28 | 0.33 |
| TA | 0.59 | 0.37 | 0.61 |
| CA | — | — | — |
| | Maximum Inhibition (%) | | |
| TC | 88.3 | 87.1 | 88.9 |
| TA | 86.7 | 84.8 | 83.1 |
| CA | 51.3 | 31.3 | 33.9 |

Following the determination of IC50 values for TC, CA and TA, combination assays were performed between these three components and the corresponding third component in the JBp1 formulation (i.e. TA versus chymotrypsinogen, CA versus trypsinogen and TC versus α-amylase).

Figure 18:
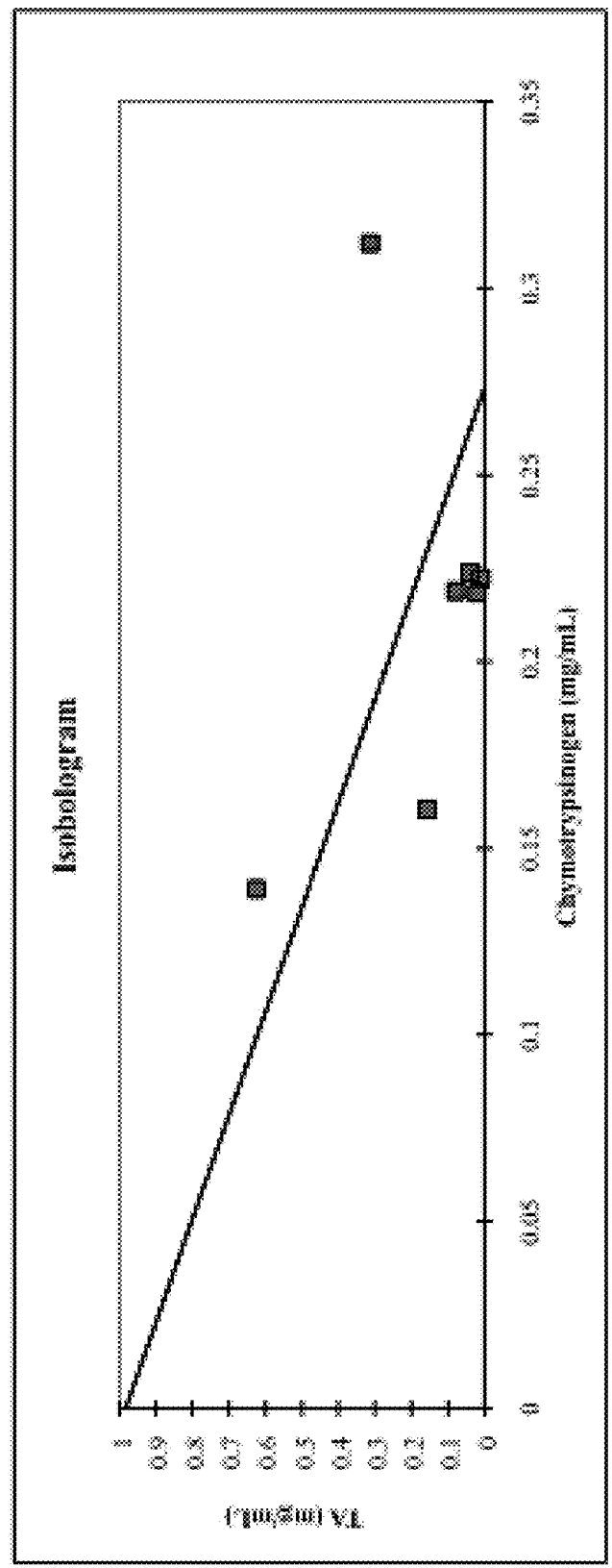
FIG. 18 provides an isobolographic analysis for TA and chymotrypsinogen in A-549, HCT-15 and MIAPaCa-2 cells.
Figure 18:
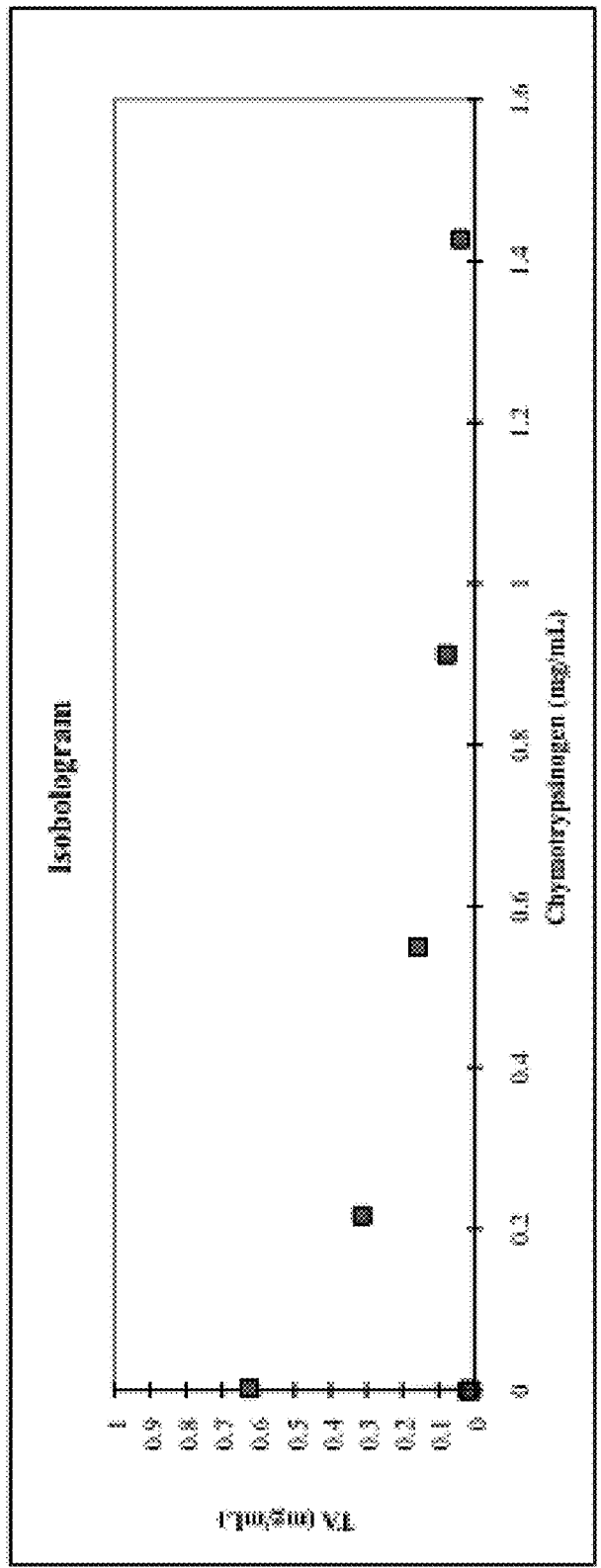
Figure 18:
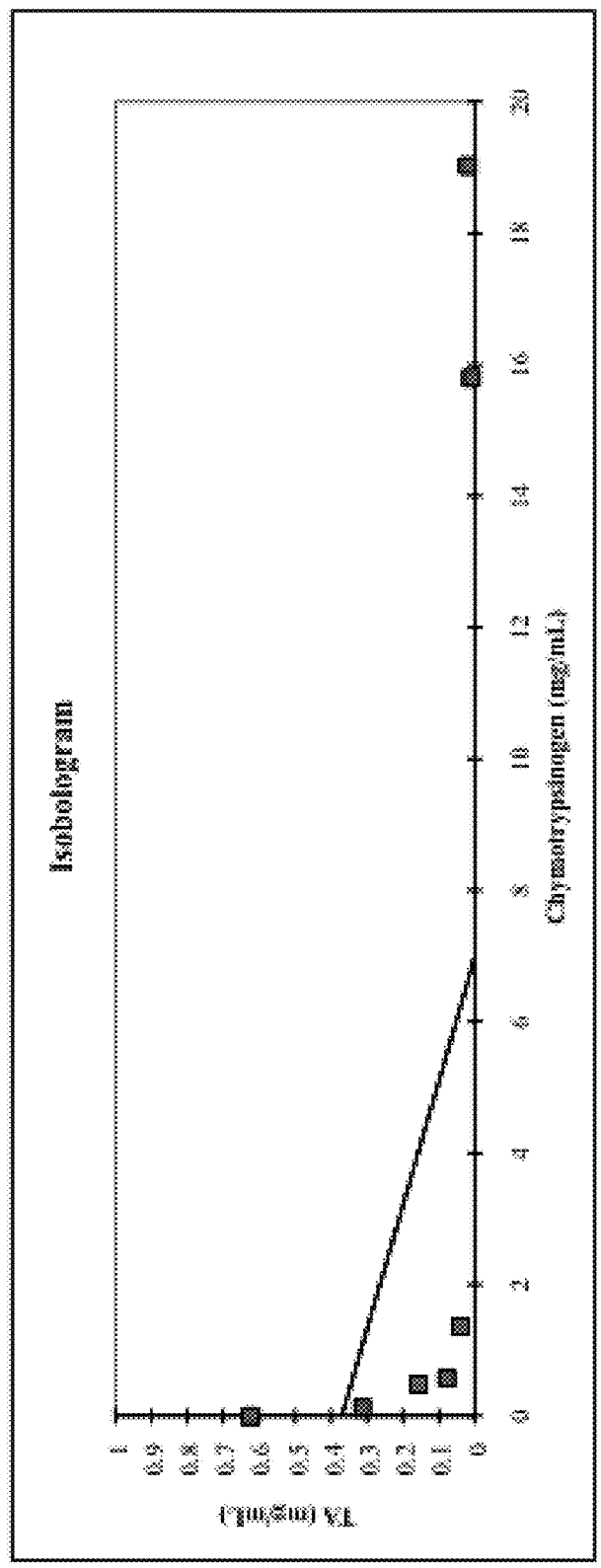

FIG. 18 presents the isobolograms for the combination between TA and chymotrypsinogen. The combination of these two compound resulted in synergistic interactions in A-549 and MIAPaCa-2 cells and a non-synergistic interaction in HCT-15 cells.

Figure 19:
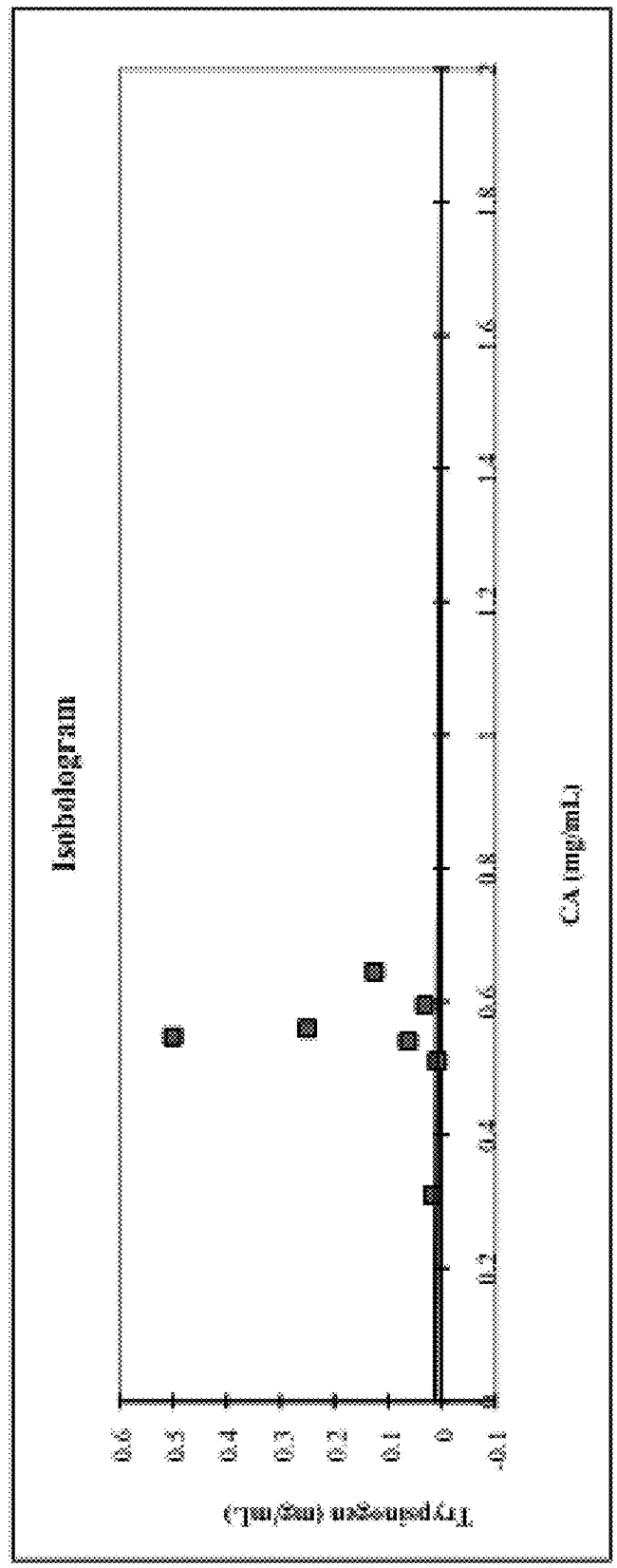
FIG. 19 provides an isobolographic analysis for CA and trypsinogen in A-549, HCT-15 and MIAPaCa-2 cells.
Figure 19:
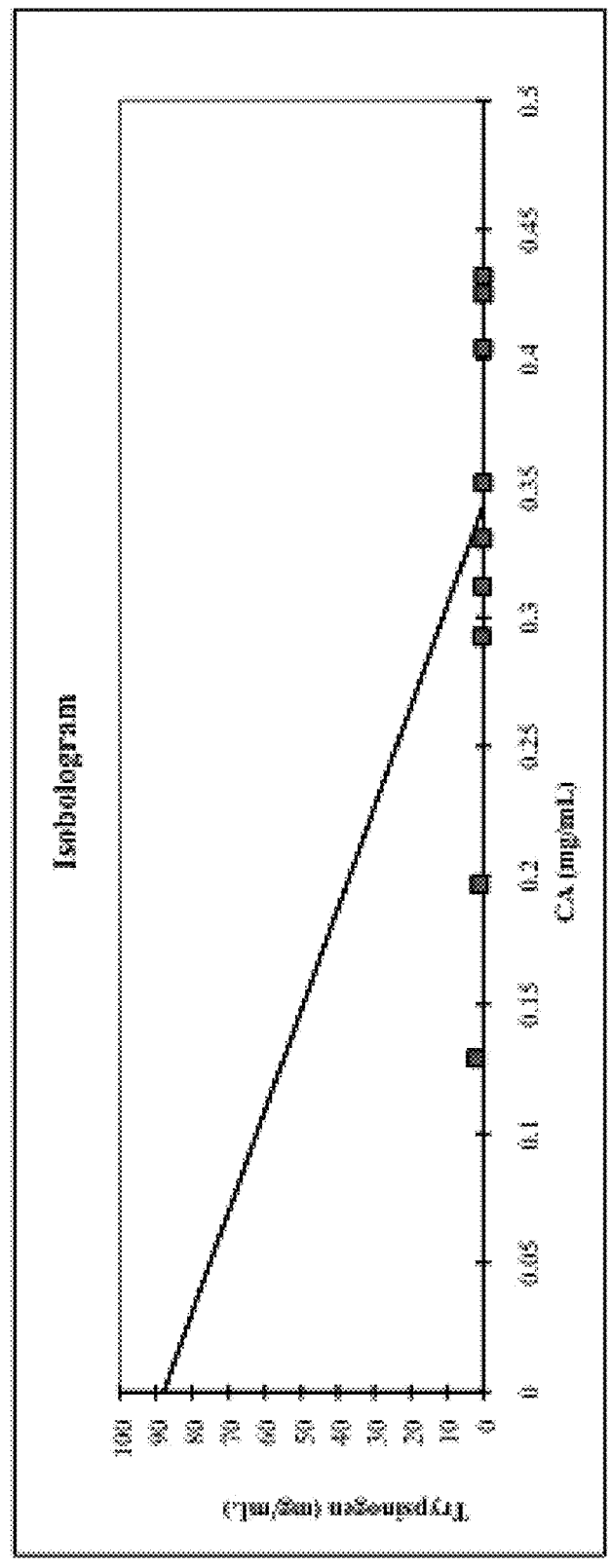
Figure 19:
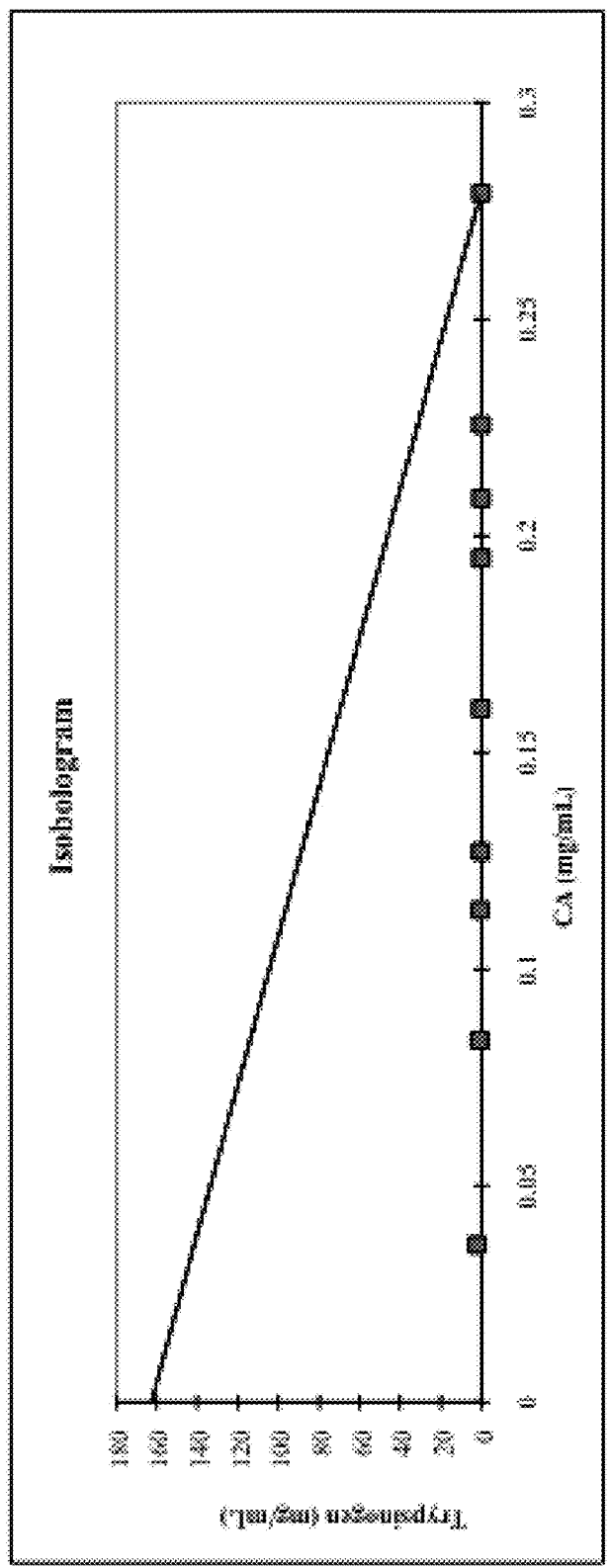

FIG. 19 presents the isobolograms for the combination between CA and trypsinogen. The combination of these two compounds resulted in synergistic interactions in HCT-15 and MIAPaCa-2 cells and a non-synergistic interaction in A-549 cells. Overall, the observed trend pointed towards a positive interaction for these two components, consistent with the synergistic interaction observed between chymotrypsinogen and trypsinogen. These results further justify the 6:1 (chymotrypsinogen:trypsinogen) ratio selected based on previous results discussed.

Figure 20:
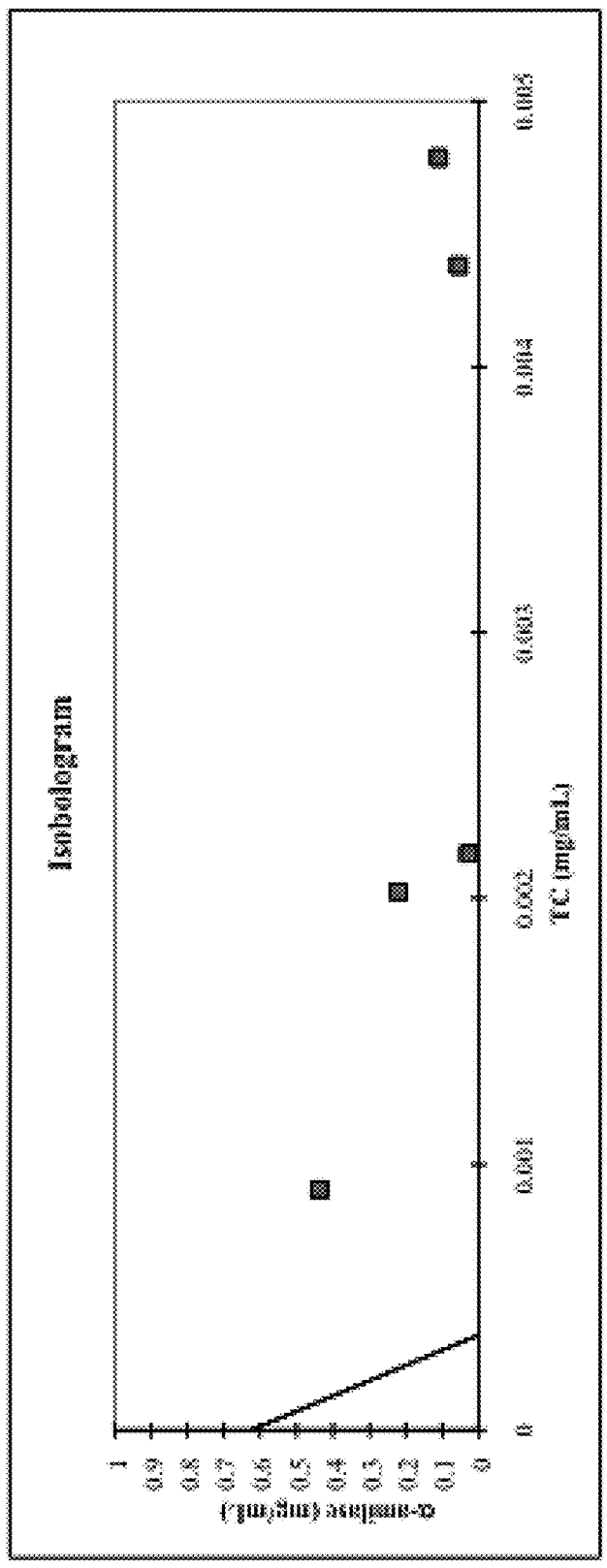
FIG. 20 provides an isobolographic analysis for TC and α-amylase in A-549, HCT-15 and MIAPaCa-2 cells.
Figure 20:
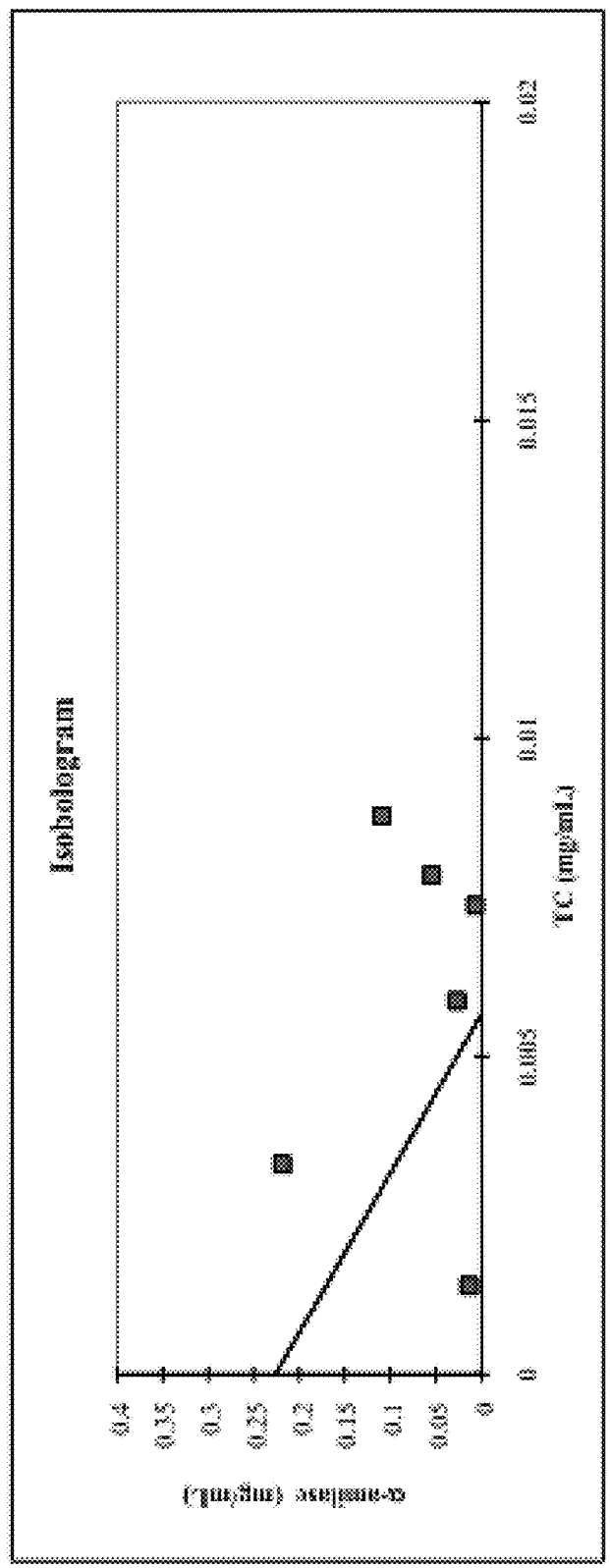
Figure 20:
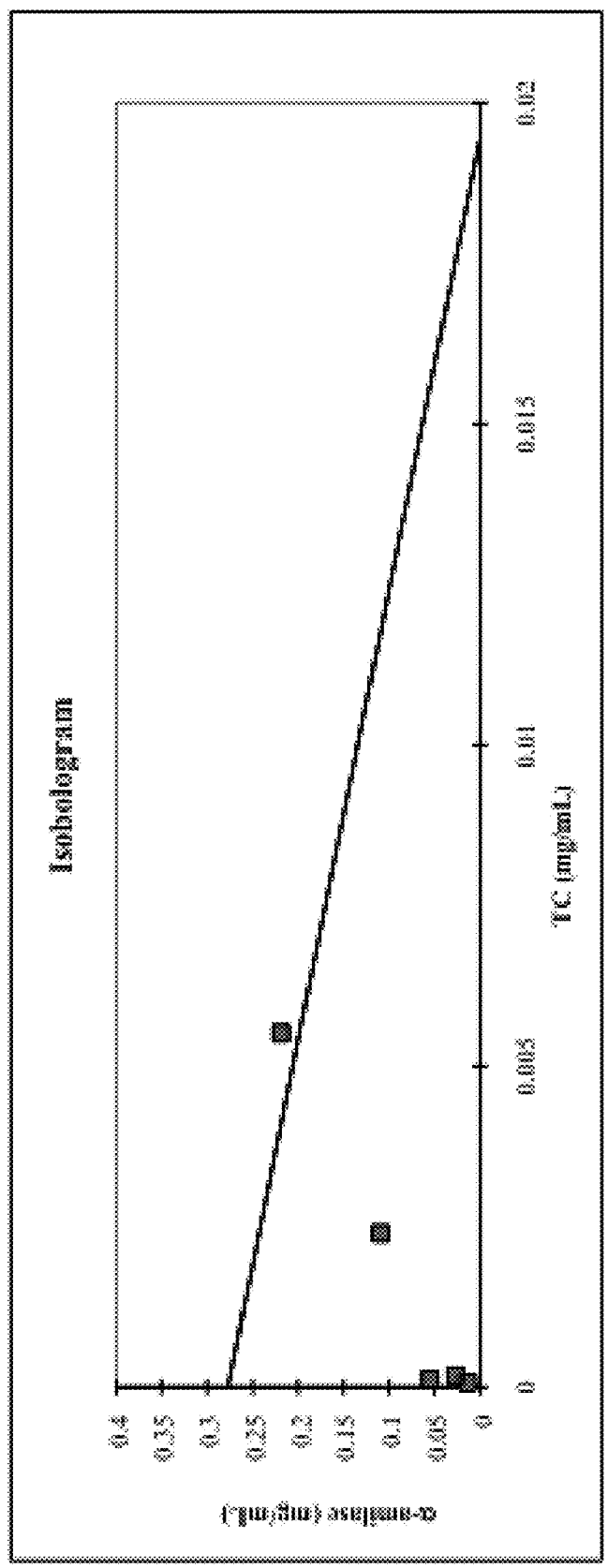

FIG. 20 presents the isobolograms for the interaction between TC and α-amylase. The overall trend observed for this combination was consistent with non-synergistic interactions. To further dissect this negative effect of α-amylase on the growth-inhibitory effects of TC, the IC50 values for TC were extracted from the isobolographic analysis template and plotted against the corresponding concentration of α-amylase. Values increased proportional to the concentration of α-amylase for all three cell lines. These results suggest that the levels of α-amylase in the JBp1 formulation should be kept low in order to avoid potential antagonistic effects with chymotrypsinogen and trypsinogen.

Table 8 above summarises all of the combination results for the individual and dual components against each other.

Based on the combination studies described above, the ratios of chymotrypsinogen, trypsinogen and α-amylase in the JBp1 formulation were defined as 6:1:0.25 (chymotrypsinogen:trypsinogen:α-amylase). This enhanced JBp1 formulation was identified by the suffix "vP" to differentiate it from the original JBp1 formulation.

IC50 values were determined for the enhanced formulation JBp1vP and compared with the values obtained for the original formulation JBp1. Table 13 presents the dose-response curves, IC50 values and maximum growth inhibition for these two formulations in A-549, HCT-15 and MIAPaCa-2 cells. As these results show, the enhanced JBp1vP formulation presented lower IC50 values than JBp1 in A-549 and HCT-15 cells and a similar IC50 value in MIAPaCa-2 cells. Importantly, JBp1vP showed higher maximum growth inhibition values than JBp1 in all three cell lines.

TABLE 13

Summary of IC50 values and maximum growth inhibition for JBp1, JBp vP and DCM in A-549, HCT-15 and MIAPaCa-2 cells.

|  | A-549 | HCT-15 | MIAPaCa-2 |
|---|---|---|---|
| IC50 values (mg/mL) | | | |
| JBp1 | 0.51 | — | 0.30 |
| JBp1vP | 0.33 | 0.36 | 0.37 |
| DCM | 1.5 | 0.4 | 0.15 |
| Maximum Inhibition (%) | | | |
| JBp1 | 65.4 | 35.2 | 81.0 |
| JBp1vP | 82.5 | 75.1 | 90.2 |
| DCM | 92.8 | 92.9 | 94.2 |

JBp1vP was examined for its ability to inhibit cell growth in combination with the test compound DCM. Prior to the combination assays, the IC50 of DCM was determined in A-549, HCT-15 and MIAPaCa-2 cells. As seen in Tables 8 and 13, DCM showed IC50 values in the range of 0.15 to 1.5 mg/mL and maximum growth inhibition values of over 92% for all three cell lines.

Figure 14:
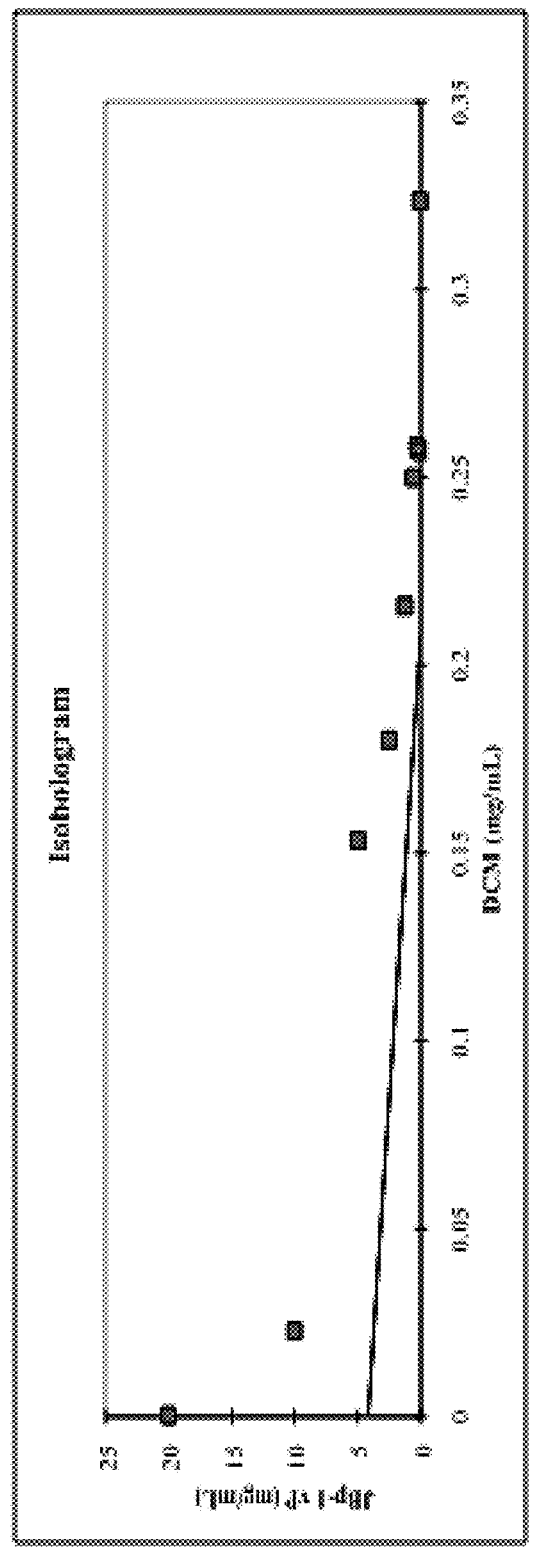
FIG. 14 provides an isobolographic analysis for JBp1vP and DCM in A-549, HCT-15 and MIAPaCa-2 cells.
Figure 14:
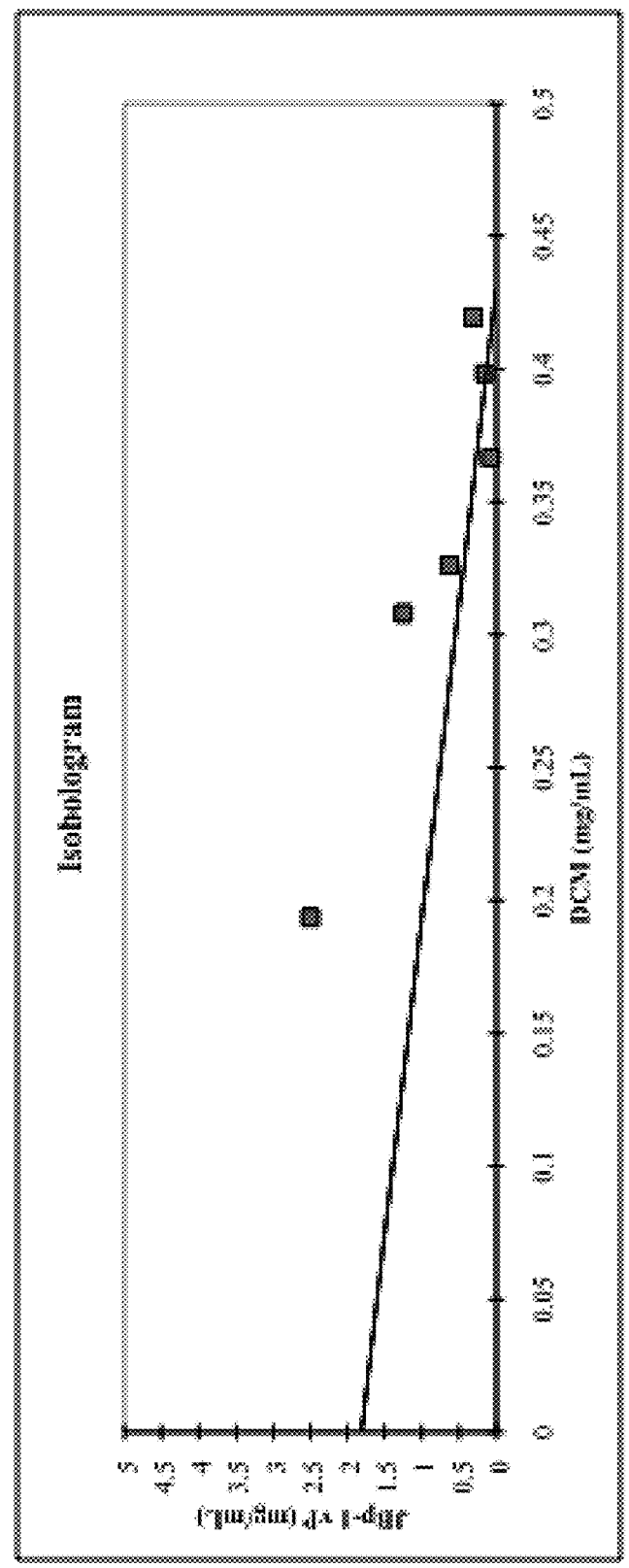
Figure 14:
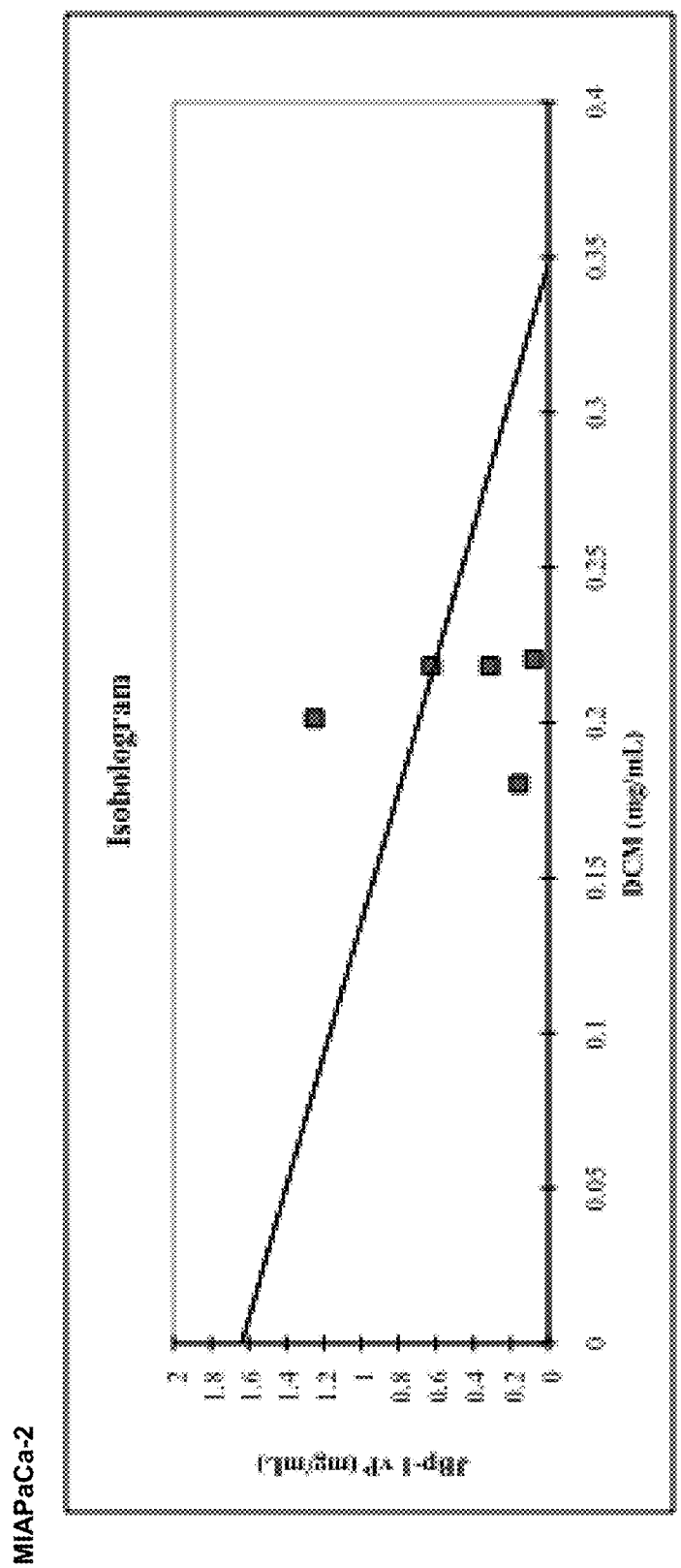

FIG. 14 shows the isobolograms for the combination between JBp1vP and DCM. The isobolographic analysis showed that the interaction between these two components in A-549 and HCT-15 cells was non-synergistic. In MIAPaCa-2 cells, the combination of JBp1vP and DCM resulted in a narrow-range synergistic interaction, specifically at lower concentrations of DCM. The g values for this combination study were well below 1.0 for the lowest two concentrations of DCM.

In view that it was understood that M may provide an atagonistic effect on JBp1, these results unexpectedly showed that DCM is effective in combination with JBp1.

In summary, JBp1vP and DCM interacted synergistically at low concentrations of DCM, JBp1vP also shows enhanced cancer cell growth inhibitory effects over JBp1 formulation in vitro, and JBp1vP and DCM synergise in order to inhibit cancer cell growth in vitro.

Example 2

In Vivo Study of Enhanced Proenzyme Formulations

A study was undertaken to determine the in vivo anti-angiogenic efficacy of JBp1 (trypsinogen, chymotrypsinogen and α-amylase), administered at 0.13 mg/kg, 0.78 mg/kg and 0.03 mg/kg, respectively), alone and in combination with an adjuvant, DCM (2-Deoxyglucose, Capsiate and Methylselenocysteine at 30.55 mg/kg, 29.12 mg/kg, 0.003 mg/kg, respectively), was investigated using vivoPharm's AngioChamber™ assay. The AngioChamber™ assay utilises the normal physiological process of wound healing, to promote fibrous capsule formation around an implanted chamber (Wood, J. M., Bold, G., Buchdunger, E., Cozens, R., et al. PTK787/ZK 222584, a Novel and Potent Inhibitor of Vascular Endothelial Growth Factor Tyrosine Kinases, Impairs Vascular Endothelial Growth Factor-Induced Responses and Tumour Growth After Oral Administration. Cancer Research, 60 (8):2178-2189 (2000)). The inclusion of Basic Fibroblast Growth Factor (bFGF) in the chamber supports the fibrouse capsule formation while inducing blood vessel development. Thus, this system is used to assess the efficacy of anti-angiogenic treatments by measuring fibrous capsule formation (wet weight of capsule at termination).

Summary

Fifty female FvB mice each received a subcutaneously implanted AngioChamber™, with or without bFGF. Ten mice were randomly selected and implanted with Chambers without bFGF. Forty mice which were implanted with Chambers containing bFGF were randomised by body weight into four treatment groups of 10 mice on Day 0 of the study.

JpB1 consisted of trypsinogen, chymotrypsinogen and α-Amylase, administered at 0.13 mg/kg, 0.78 mg/kg and 0.03 mg/kg, respectively. DCM consisted of 2-Deoxyglucose, Capsiate and Methylselenocysteine at 30.55 mg/kg, 29.12 mg/kg, 0.003 mg/kg, respectively.

The mice in each group received daily treatment (Day 0 to 4) with either Vehicle Control (NMP:PEG300 (1:9, v/v), p.o., 5 mL/kg), JBp1 (i.p., in a dosing volume of 10 mL/kg), JBp1-DCM (i.p., in a dosing volume of 10 mL/kg) or Sorafenib (60 mg/kg, p.o., in a dosing volume of 5 mL/kg). Vehicle Control was administered to two groups, one of which was implanted with AngioChambers™ loaded without bFGF (Baseline Control), the other implanted with AngioChambers™ with bFGF (Induction Control). The compound treatment groups were implanted with AngioChambers™ loaded with bFGF.

Body weight measurements were recorded for all animals on the first treatment day (Day 0) and then daily until the termination day of the study (Day 5).

Mice in all groups lost body weight immediately following the onset of treatment, an expected result of the surgical procedure. Mice treated with Vehicle Control (with bFGF) JBp1 and JBp1-DCM recovered body weight over the remaining duration of the study, with no significant loss of mean body weight on the termination day. Body weight did not recover in mice treated with Vehicle Control (without bFGF) and Sorafenib, with both groups having significant body weight loss at termination of the study, which is common in mice treated with NMP: PEG300.

AngioChambers™ were excised from each mouse 24 hours following final treatment (Day 5). The fibrous capsule around the chamber was removed and the wet weight recorded.

All treatments resulted in significant inhibition of bFGF-induced angiogenesis compared with the Induction Control, as indicated by the capsule wet weights on the termination day of the study. Treatment with JBp1-DCM and Sorafenib, which is an effective angiogenic drug comparator, significantly reduced angiogenesis compared with JBp1 monotherapy. There was no significant difference in anti-angiogenic activity between JBp1-DCM and Sorafenib. Therefore, in this model, both JBp1 and JBp1-DCM were efficacious in inhibition of fibrous capsule formation. The addition of DCM to the JBp1 formulation resulted in an enhanced inhibition compared to JBp1 alone. The treatment of JBp1-DCM was as effective as Sorafenib in this model.

Materials and Methods

Heparin, NMP, PBS and PEG300 were obtained from Sigma-Aldrich (Castle Hill, NSW, Australia). 0.22 µM Acrodisc filters were obtained from Pall Corporation (Sydney, NSW, Australia). Recombinant human bFGF was obtained from Shenandoah Biotechnology (Warwick, Pa., USA). AngioChambers™ were supplied by Angst+Pfister AG (Stuttgart, Germany). Agarose was supplied by Omnigel Lo. M (Edwards Instruments Co., NSW, Australia).

The test system involved 50 female FvB mice, with 5 study groups of 10 mice per group (2 control and 3 treatment groups). Standard conditions and regimes were used for animal management.

Porous tissue chambers (AngioChambers™) made of perfluoro-alkoxy-Teflon (Teflon®-PFA, 21 mm×8 mm diameter, 5500, volume), perforated with 80 regularly spaced 0.8 mm holes were used. Both ends were sealed with removable caps of the same material. Chambers were filled under sterile conditions with 0.8% agarose containing 20 IU/mL heparin, with or without 4 μg/mL bFGF. The agarose solution was maintained at 37° C. before filling the chambers.

For chamber implantation, mice were anaesthetised by isofluorane inhalation. A small incision was made in the centre dorsal skin of each mouse and the chamber was inserted subcutaneously and placed between the shoulder blades. The wound was closed with two 1.4 mm wound clips (Michel Clip).

Test Compounds and Formulations

The vehicle control was NMP:PEG300 (1:9 v/v). JpB1 was test article 1 and consisted of trypsinogen, chymotrypsinogen and α-Amylase, administered at 0.13 mg/kg, 0.78 mg/kg and 0.03 mg/kg, respectively. DCM was test article 2 and consisted of 2-Deoxyglucose, Capsiate and Methylselenocysteine at 30.55 mg/kg, 29.12 mg/kg, 0.003 mg/kg, respectively. Each compound was dissolved separately in PBS. Stock solutions were sterilised by filtration (0.22 μM). On each day of dosing, stocks were mixed into the appropriate combinations.

Sorafenib was the reference compound and was supplied as 315 mg tablets containing 200 mg active Sorafenib. Tablets were crushed and dissolved in NMP to formulate stock solution of active Sorafenib, which was diluted with PEG300 to achieve the required dose concentration with a final NMP:PEG300 ratio of 1:9.

Ten mice were randomly selected and implanted with Chambers without bFGF. Forty mice which were implanted with Chambers containing bFGF were randomised by body weight into four treatment groups of 10 mice on Day 0 of the study. Treatments began on Day 0 (2 hours after the mice had recovered from surgery) and were continued for five consecutive days (Day 0 to 4).

The Vehicle Control (NMP:PEG300 (1:9 v/v)) (Groups 1 and 2) and Sorafenib (60 mg/kg; Group 5) were administered orally (p.o.) in a dosing volume of 5 mg/kg. JBp1 (trypsinogen, chymotrypsinogen and α-Amylase at 0.13 mg/kg, 0.78 mg/kg and 0.03 mg/kg, respectively) was administered alone (Group 3) and in combination with DCM (2-Deoxyglucose, Capsiate and Methylselenocysteine at 30.55 mg/kg, 29.12 mg/kg, 0.003 mg/kg, respectively) (Group 4). Both were administered by intraperitoneal injection (i.p.) in a dosing volume of 10 mL/kg. When JBp1 and DCM were administered in combination all six compounds were formulated and administered together in the one injection.

Each animal's body weight was measured immediately prior to dosing. The volume of dosing solution administered to each animal was calculated and adjusted based on individual body weight.

Animals were treated according to the above schedule, beginning 2 hours after the mice recovered from surgery to implant the AngioChamber™ on Study Day 0. AngioChambers™ were excised from all mice post-mortem on the termination day (Day 5). The vascularised fibrous capsule that had formed around each chamber was carefully removed and the wet weight recorded immediately.

Treatment of any animal would cease if its body weight dropped to below 85% of that on entry into the study. If this occurred, body weight measurements would continue for a short period. If no gain in body weight was measured, the animal would be culled. Animals would also be culled if severe adverse reaction to the treatment was observed. The extent of the adverse reaction was assessed using a proforma clinical score sheet listing symptoms and an accompanying score (guide given in Appendix 2). The combination of symptoms observed and resultant summed score determined the course of action to be taken with regard to the animal's welfare.

Angiogenesis inhibition by Test Articles (%) was calculated using the following formula:

$$\% \text{ Inhibition} = [(A-B)/(A-C) \times 100]$$

where A is the mean capsule weight from mice with implanted AngioChambers™ containing growth factor and treated with Vehicle Control (Group 2),
B is the mean capsule weight from mice with implanted AngioChambers™ containing growth factor and treated with Test Article (Groups 3-5),
and C is the mean capsule weight from mice with implanted AngioChambers™ without growth factor and treated with Vehicle Control (Group 1).

All statistical calculations were performed using SigmaStat 3.0 (SPSS Australasia, North Sydney, NSW, Australia). A paired t-test was used to determine the significance in body weight change within a treatment group between Day 0 and the termination day of the study. Where the data did not pass the Normality Test, the Wilcoxon Signed Rank Sum Test was performed. The goal of the remaining statistical analyses was to show that the reference compound, Sorafenib and the Test Articles inhibited the induction of the fibrous capsule by bFGF significantly. Significant induction of the fibrous capsule formation by bFGF is considered to be essential to accept the study results. A One-Way Analysis of Variance (ANOVA) was performed on the capsule weight data at the end of the study. Where significant differences were found, All Pairwise Multiple Comparison and Multiple Comparison versus Control Group Procedures (Holm-Sidak Method) were performed. A p value of less than 0.05 was considered significant.

All procedures used in the performance of this study were carried out in accordance with vivoPharm's Standard Operating Procedures, with particular reference to SOP # vP_EF0317 "General Procedures for Angiogenesis Studies". The Standard Operating Procedures are maintained on-file at vivoPharm's secure facilities.

Results and Observations

All mice in all groups presented with piloerection for the duration of the study. One mouse treated with Vehicle Control (with bFGF; Group 2) was found dead on Day 1 of the study, likely due to complications of surgery. One mouse treated with Vehicle Control (without bFGF; Group 1) had the hind right leg adhered to abdominal fur on Day 4. This was separated under inhalation anaesthetic.

Mice in all groups lost body weight immediately following the onset of treatment, likely due to the surgical procedure. Mice treated with Vehicle Control (with bFGF; Group 2) JBp1 (Group 3) and JBp1-DCM (Group 4) steadily recovered body weight over the remaining duration of the study, with no significant loss of mean body weight on the termination day.

Body weight did not recover in mice treated with Vehicle Control (without bFGF; Group 1) and Sorafenib (Group 5), with both groups having significant body weight loss (5.5% and 5.6%, respectively) at termination of the study.

The wet weight of the fibrous capsule is primarily driven by the extent of angiogenesis induced by the bFGF captured in the AngioChambers™ and subsequently by stimulation of endogenous VEGF. A small or light fibrous capsule correlates with a small degree of blood vessel formation within, and hence higher inhibition of angiogenesis by a particular treatment.

In this study, fibrous capsule formation of the excised capsules was significantly greater in the Vehicle Control group with bFGF loaded in the chamber (Group 2, Induction Control) than in the Vehicle Control group without bFGF loaded into the chamber (Group 1, Baseline Control) (FIG. 21) indicating that bFGF adequately and significantly stimulated capsule formation.

As all treatment groups had bFGF loaded into the chamber, all comparisons to the Vehicle Control group discussed hereafter refer to the Induction Control, Group 2 (with bFGF loaded in the chamber).

Figure 21:
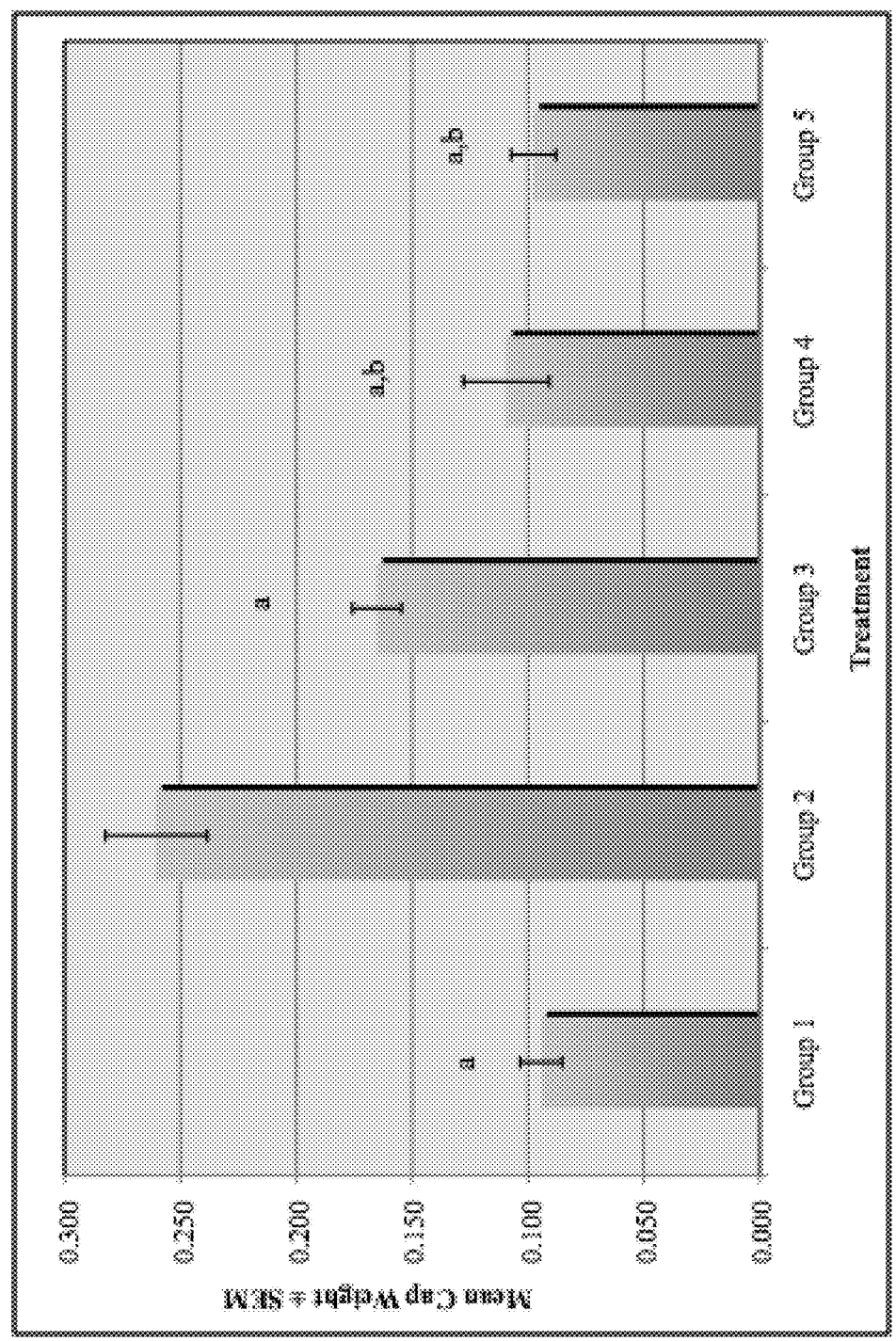
FIG. 21 provides a bar graph showing mean capsule weights for various formulations of Groups 1 to 5 in a comparison in vivo anti-angiogenic study of mice fitted with fibrous capsules.

FIG. 21 shows results of testing for Groups 1-5. Group 1 is Vehicle Control (NMP:PEG300 (1:9, v/v)) without bFGF. Group 2 is Vehicle Control (NMP:PEG300 (1:9, v/v)), with bFGF. Group 3 is JBp1*, with bFGF. Group 4 is JBp1-DCM*, with bFGF. Group 5 is Sorafenib, 60 mg/kg, with bFGF. Reference symbol "a" means significantly different to Induction Control (Vehicle Control with bFGF (Group 2)) ($p<0.05$: One Way ANOVA). Reference symbol "b" means significantly different to JBp1 monotherapy (with bFGF) (Group 3) ($p<0.05$: One Way ANOVA). All treatments were administered once daily for 5 days (Day 0-4).

Treatment with JBp1, JBp1-DCM and Sorafenib (Groups 3, 4 and 5, respectively) resulted in a significant reduction in angiogenesis compared to the Induction Control (Group 2)), as indicated by the difference in capsule weight (FIG. 21). Treatment with JBp1-DCM and Sorafenib (Groups 4 and 5, respectively) significantly reduced angiogenesis compared with JBp1 monotherapy (Group 3).

Chambers harvested from mice treated with JBp1 alone (Group 3) had more free blood in the space between the fibrous capsule and the chamber than those treated with JBp1-DCM (Group 4). The fibrous capsule around the Chambers harvested from mice treated with JBp1-DCM (Group 4) were more rigid than treated with Vehicle Control (without and with bFGF; Group 1 and 2, respectively).

CONCLUSION

The in vivo anti-angiogenic efficacy of intraperitoneal treatment with JBp1 (trypsinogen (0.13 mg/kg), chymotrypsinogen (0.78 mg/kg) and α-Amylase (0.03 mg/kg)), administered alone and in combination with DCM (2-Deoxyglucose (30.55 mg/kg), Capsiate (29.12 mg/kg) and Methylselenocysteine (0.003 mg/kg)) was investigated in female FvB mice using vivoPharm's AngioChamber™ assay. The effect of the Test Articles was compared with that of a reference compound, Sorafenib (60 mg/kg, p.o.).

In this Study all treatments resulted in significant inhibition of bFGF-induced angiogenesis compared with the Induction Control, as indicated by the capsule wet weights on the termination day of the study. Both the reference compound, Sorafenib, and the combination of JBp1-DCM significantly reduced angiogenesis compared with JBp1 monotherapy. JBp1-DCM has therefore been shown to be efficacious in reducing angiogenesis.

Example 3

In Vitro Study of Proenzyme Formulations

A study was undertaken to determine the effect of the proenzyme formulation comprising trypsinogen (pT), chymotrypsinogen (pC) and α-amylase (A) (formulation referred to as JBp1vP) with active agents of methylselenocysteine (M), capsiate (C) or 2-deoxyglucose (D). The study applied the isobolographic method to understand the interaction between these components.

SUMMARY

Figure 22A:
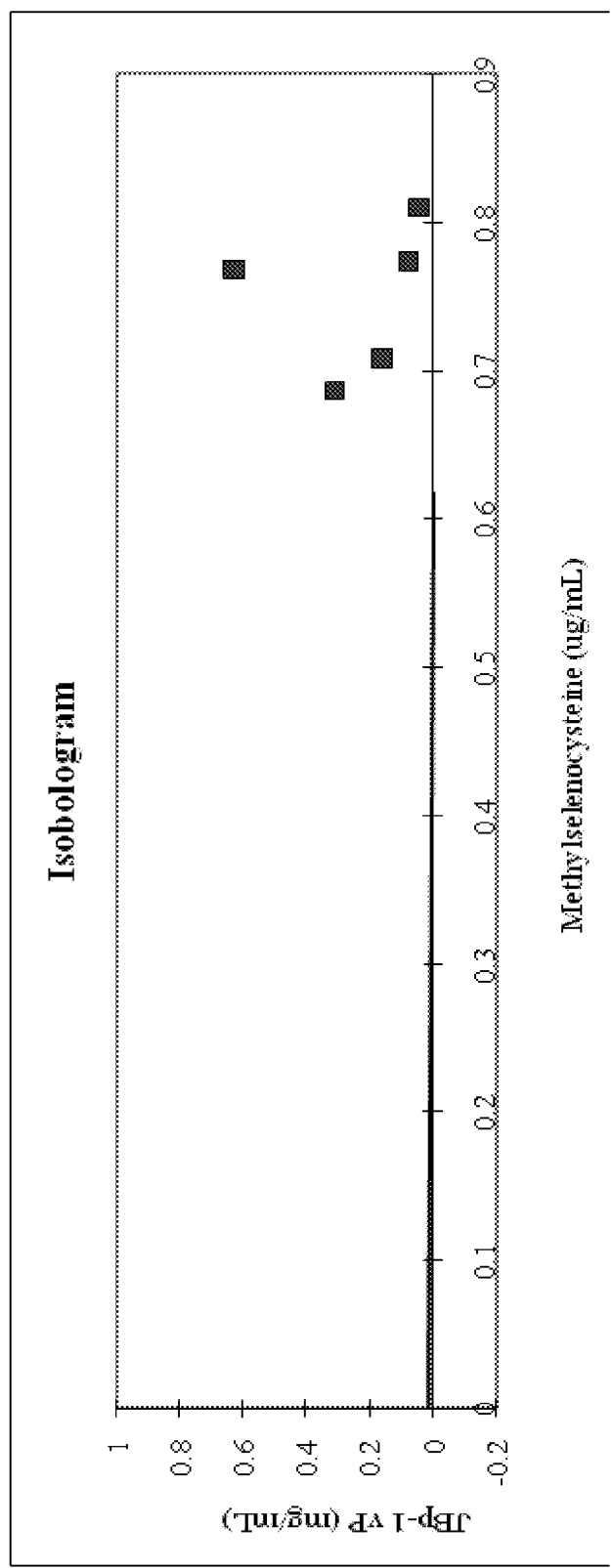
FIGS. 22A and 22B provide an isobolographic analysis for JBp1vP and methylselenocysteine in HCT-15 cells.
Figure 22B:
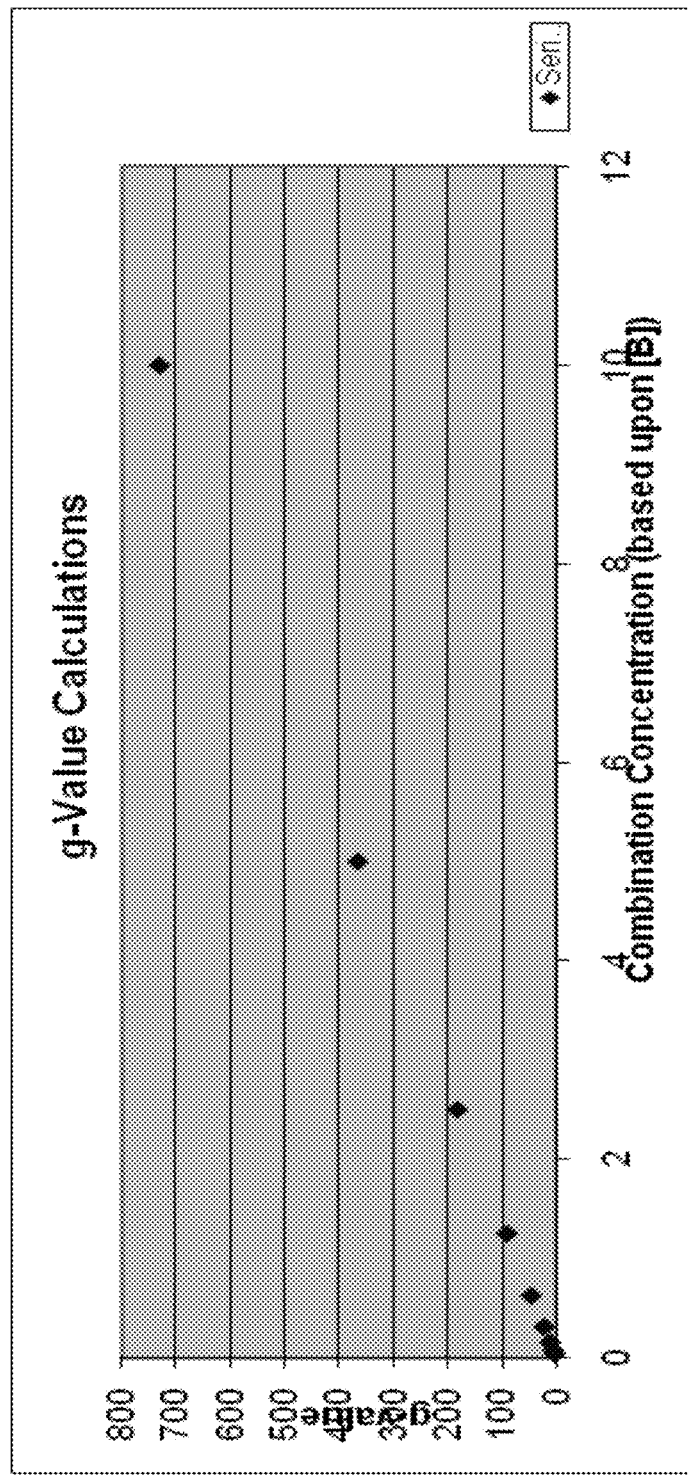
Figure 23A:
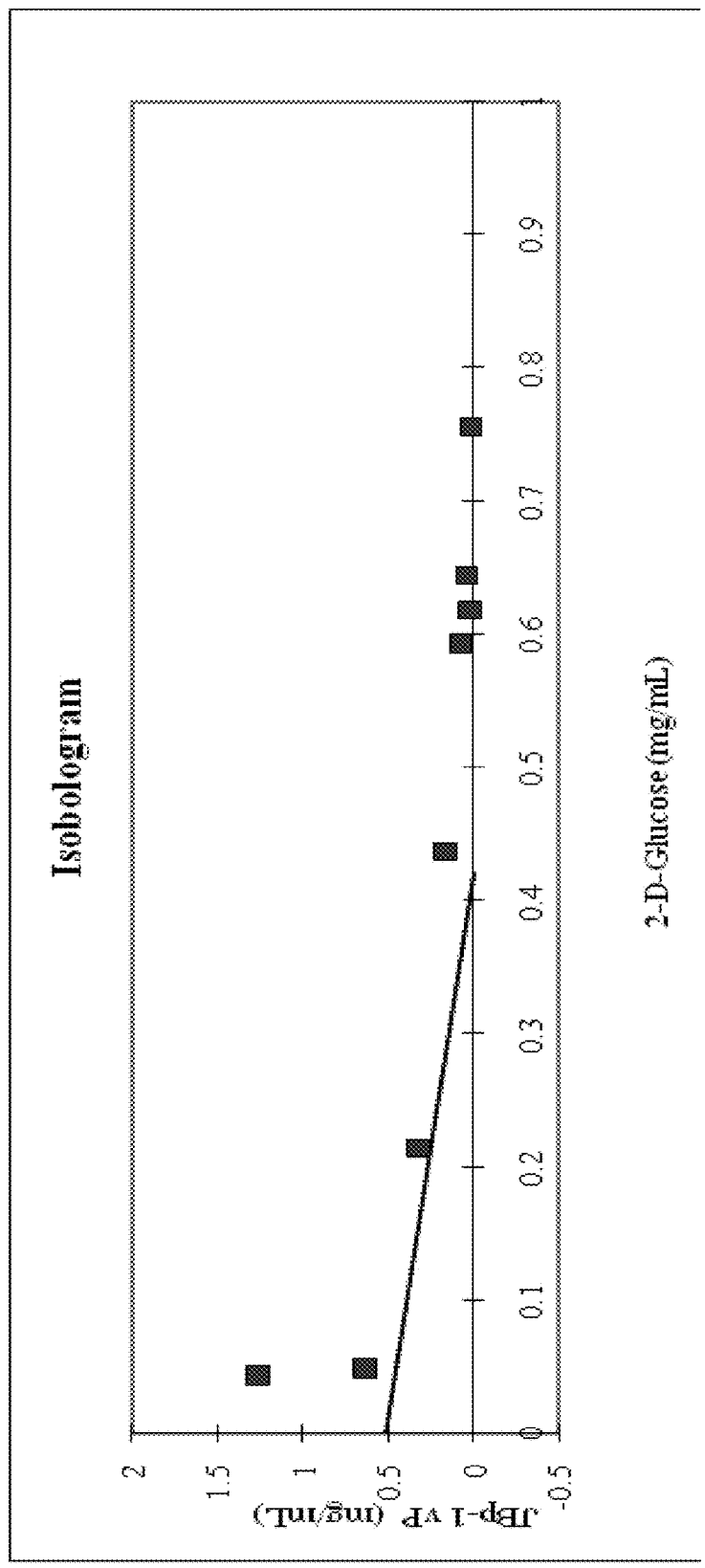
FIGS. 23A and 23B provide an isobolographic analysis for JBp1vP and 2-deoxyglucose in HCT-15 cells.
Figure 23B:
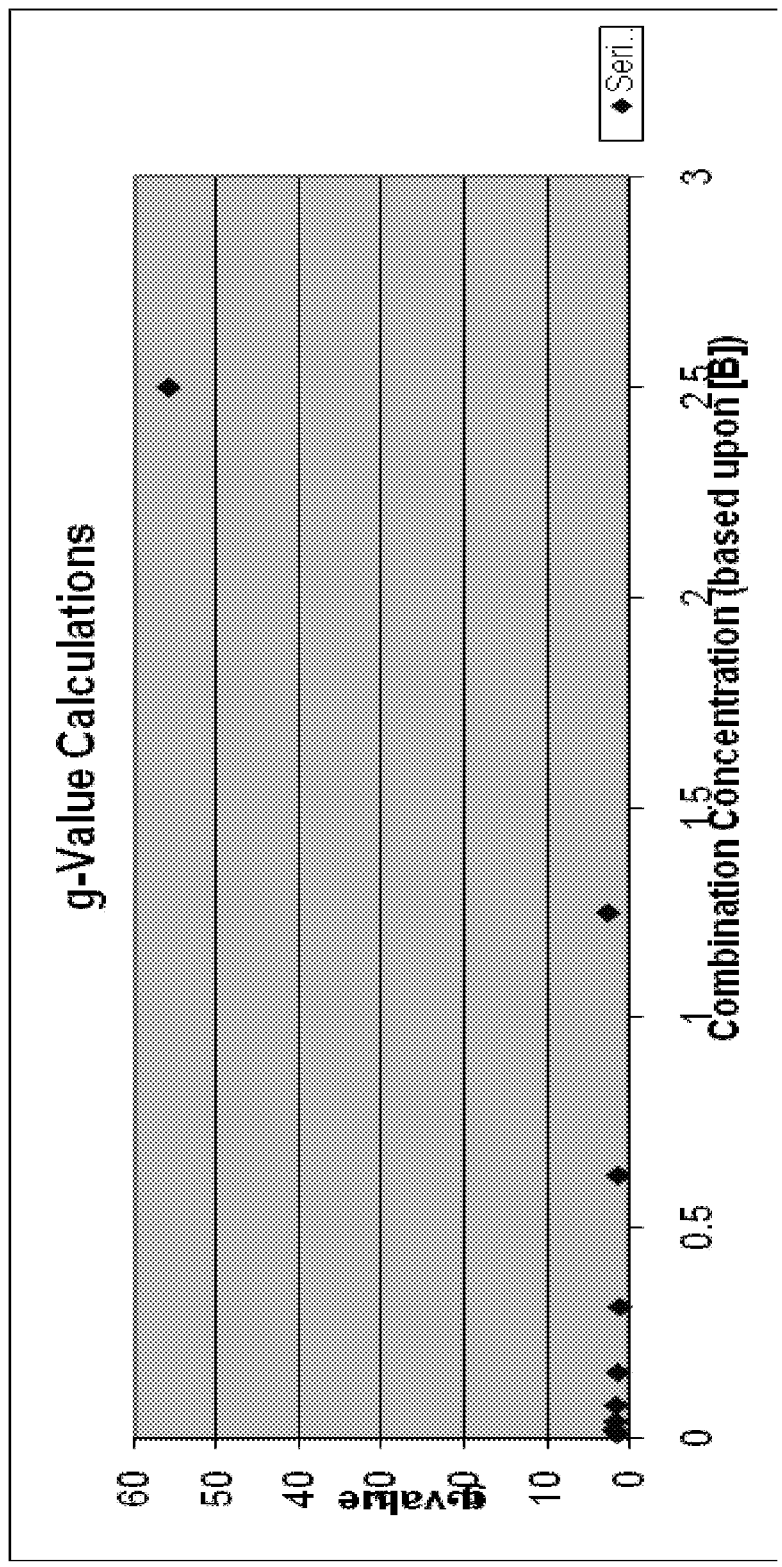
Figure 24A:
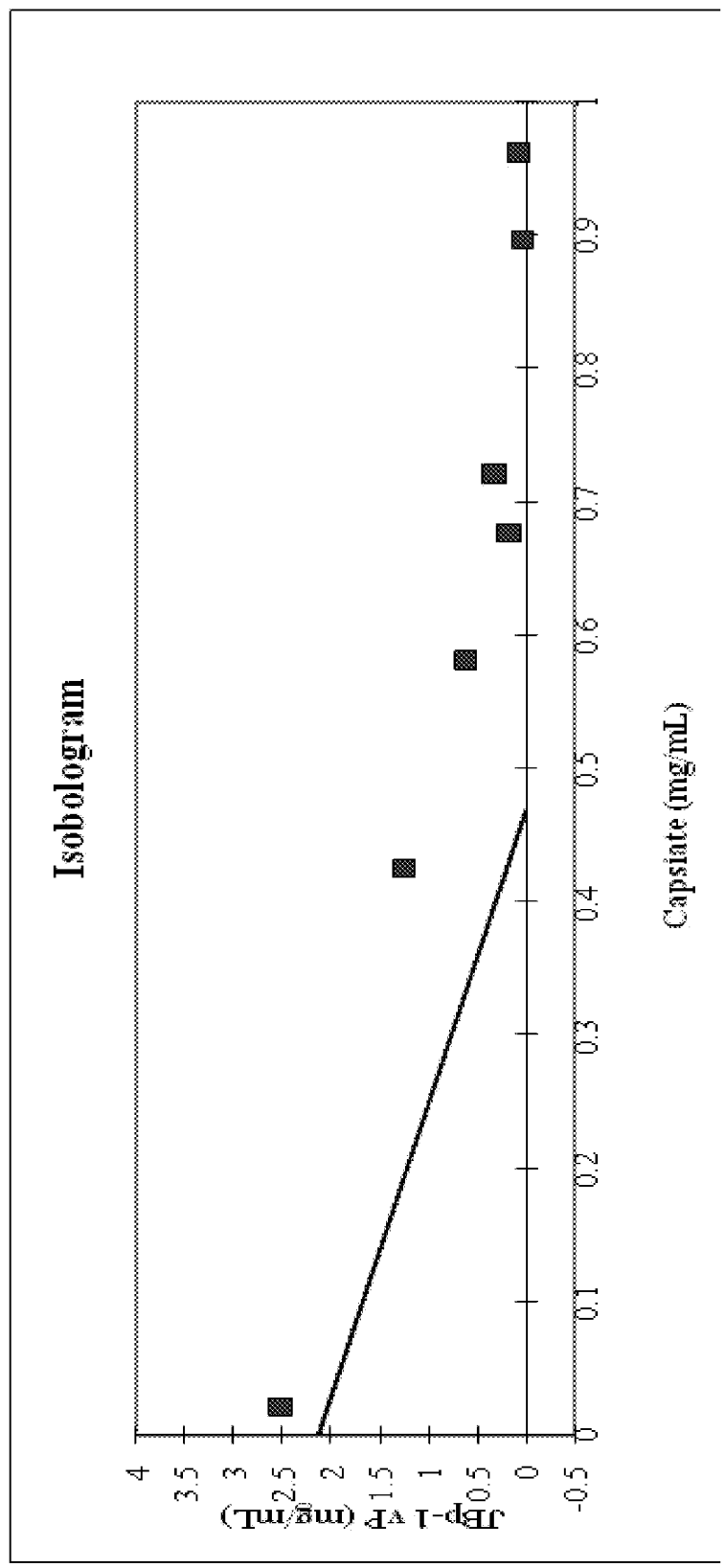
FIGS. 24A and 24B provide an isobolographic analysis for JBp1vP and capsiate in HCT-15 cells.
Figure 24B:
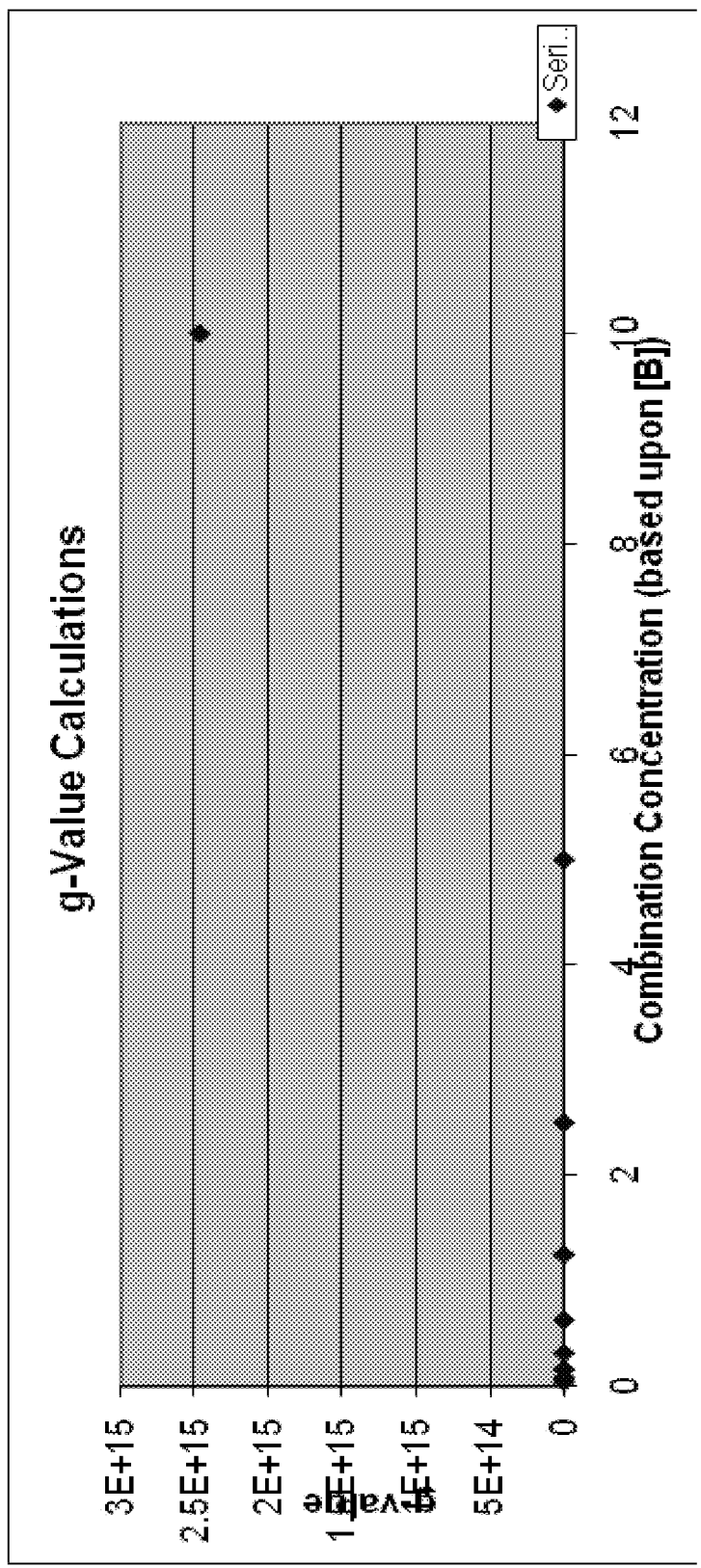

The cell growth inhibitory properties of these proenzyme formulations were studied. Based on the IC50 values and maximum growth inhibition, three cell lines, A-549, HCT-15 and MIAPaCa-2 were selected for the combination studies using the isobolographic method. The use of isobolograms allowed the study of the level of interaction between the three individual components and JBp1vP. By studying the growth inhibition activity of the individual components in combination with each other and as mixtures with JBp1vP, enhanced formulations were identified. The results of these enhanced formulations are shown in FIGS. 22-24, which provide an isobolographic analysis for JBp1vP and individually M, C and D, respectively, in HCT-15 cells.

Example 4

In Vitro Study of Formulations Containing 2-Deoxyglucose and Methylselenocysteine A study was undertaken to determine the effect of a formulation comprising methylselenocysteine (M) and 2-deoxyglucose (D). The study applied the isobolographic method to understand the interaction between these components.

SUMMARY

Figure 25A:
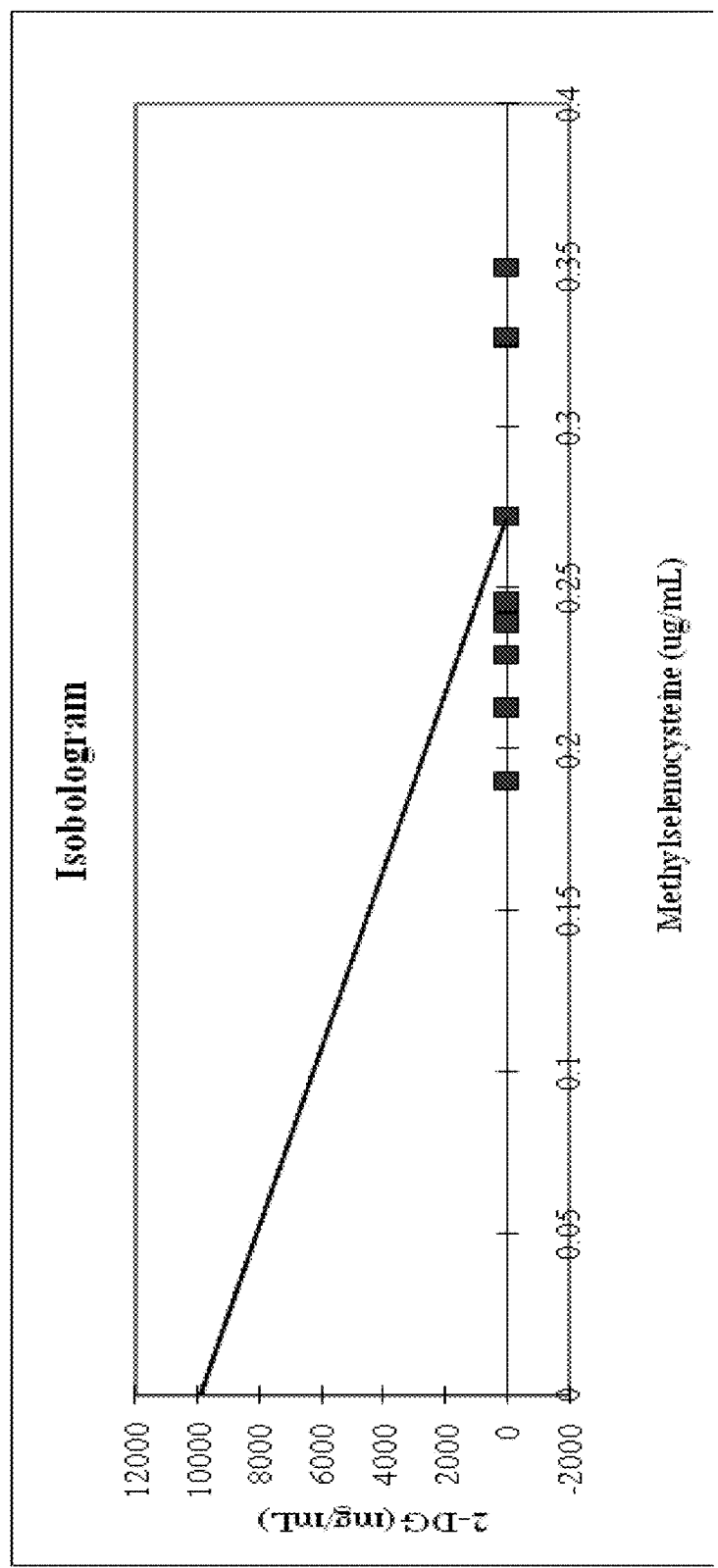
FIGS. 25A and 25B provide an isobolographic analysis for 2-deoxyglucose and methylselenocysteine in HCT-15 cells.
Figure 25B:
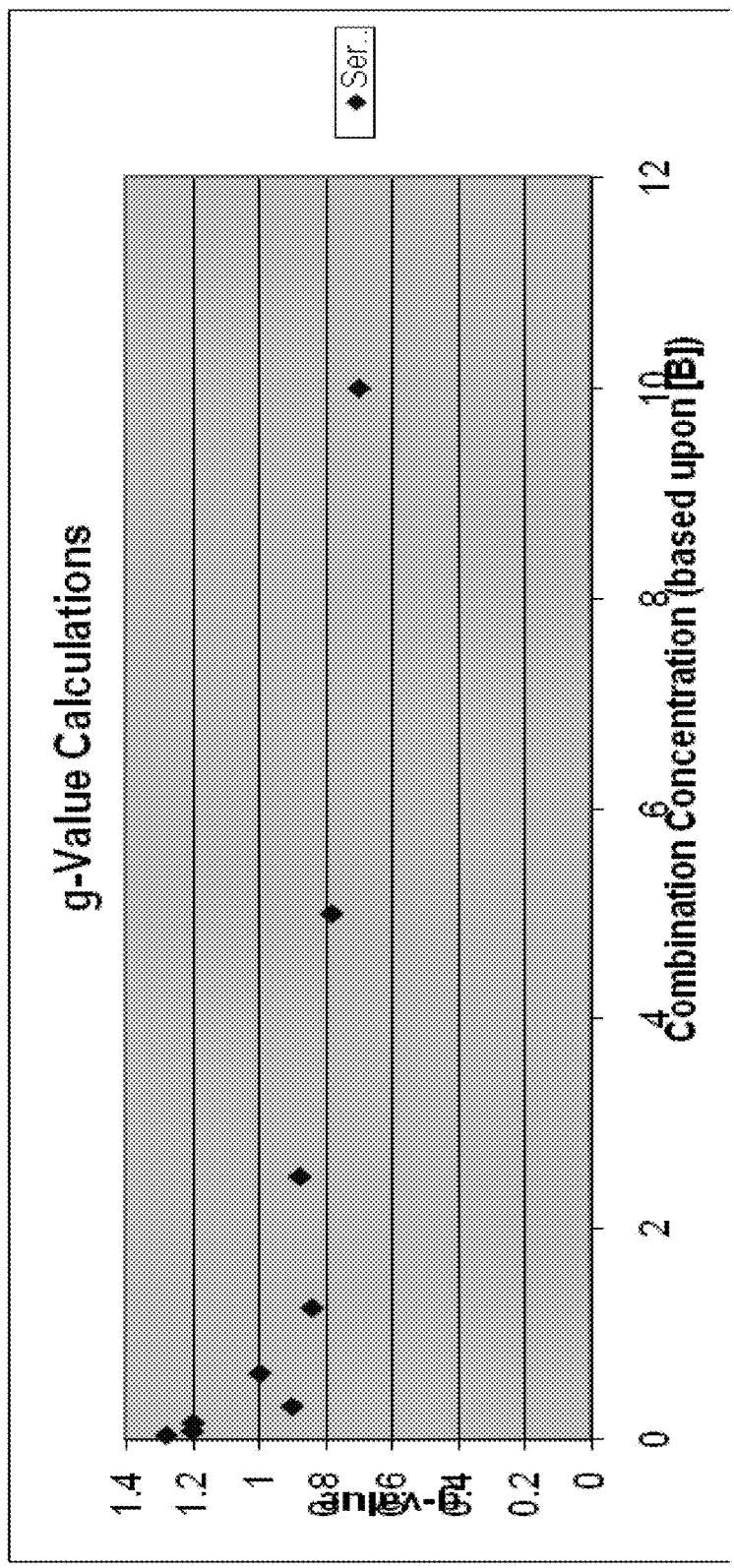

The cell growth inhibitory properties of these proenzyme formulations were studied. Based on the 1050 values and maximum growth inhibition, three cell lines, A-549, HCT-15 and MIAPaCa-2 were selected for the combination study using the isobolographic method. The use of isobolograms allowed the study of the level of interaction between these two components. By studying the growth inhibition activity of the individual components and in combination with each other, an enhanced formulation was identified. The results of the enhanced formulation is shown in FIG. 25, which provides an isobolographic analysis for the M and D combination in HCT-15 cells.

The invention claimed is:

1. A method of treating a solid tumor comprising administering to a subject a pharmaceutical composition comprising a therapeutically effective amount of trypsinogen and chymotrypsinogen, wherein the composition does not contain amylase, and wherein the weight ratio of chymotrypsinogen:trypsinogen is in the range of between 4:1 to 8:1.

2. The method of claim 1, wherein the weight ratio of chymotrypsinogen:trypsinogen is in the range of between 5:1 to 7:1.

3. The method of claim 1, wherein the weight ratio of chymotrypsinogen:trypsinogen is 6:1.

4. A method of treating a solid tumor comprising administering to a subject a pharmaceutical composition consisting essentially of a therapeutically effective amount of trypsinogen and chymotrypsinogen, wherein the weight ratio of chymotrypsinogen:trypsinogen is in the range of between 4:1 to 8:1.

5. The method of claim 4, wherein the weight ratio of chymotrypsinogen:trypsinogen is in the range of between 5:1 to 7:1.

6. The method of claim 4, wherein the weight ratio of chymotrypsinogen:trypsinogen is 6:1.

7. A method of treating a solid tumor comprising administering to a subject a pharmaceutical composition comprising
- a pharmaceutically acceptable carrier, vehicle or diluent; and
- a protease proenzyme composition consisting of trypsinogen and chymotrypsinogen, wherein the weight ratio of chymotrypsinogen:trypsinogen is in the range of between 4:1 to 8:1.

8. The method of claim 7, wherein the weight ratio of chymotrypsinogen:trypsinogen is in the range of between 5:1 to 7:1.

9. The method of claim 7, wherein the weight ratio of chymotrypsinogen:trypsinogen is 6:1.

10. The method of claim 1, wherein the solid tumor is colorectal cancer.

11. The method of claim 1, wherein the solid tumor is pancreatic cancer.

12. The method of claim 1, wherein the solid tumor is brain cancer.

13. The method of claim 1, wherein the solid tumor is liver cancer.

14. The method of claim 4, wherein the solid tumor is colorectal cancer.

15. The method of claim 4, wherein the solid tumor is pancreatic cancer.

16. The method of claim 4, wherein the solid tumor is brain cancer.

17. The method of claim 4, wherein the solid tumor is liver cancer.

18. The method of claim 7, wherein the solid tumor is colorectal cancer.

19. The method of claim 7, wherein the solid tumor is pancreatic cancer.

20. The method of claim 7, wherein the solid tumor is brain cancer.

21. The method of claim 7, wherein the solid tumor is liver cancer.

* * * * *

UNITED STATES PATENT AND TRADEMARK OFFICE
CERTIFICATE OF CORRECTION

| | |
|---|---|
| PATENT NO. | : 9,636,359 B2 |
| APPLICATION NO. | : 13/502917 |
| DATED | : May 2, 2017 |
| INVENTOR(S) | : Julian Norman Kenyon et al. |

It is certified that error appears in the above-identified patent and that said Letters Patent is hereby corrected as shown below:

On the Title Page

(73) Assignee: replace "The University of Sydney, New South Wales (AU)" with -- Propanc Pty Ltd, Richmond (AU) --

Signed and Sealed this
Eighth Day of August, 2017

Joseph Matal
*Performing the Functions and Duties of the*
*Under Secretary of Commerce for Intellectual Property and*
*Director of the United States Patent and Trademark Office*